(12) United States Patent
Lowe, III

(10) Patent No.: US 7,012,078 B2
(45) Date of Patent: Mar. 14, 2006

(54) 2-AMINOPYRIDINES CONTAINING FUSED RING SUBSTITUENTS

(75) Inventor: John Adams Lowe, III, Stonington, CT (US)

(73) Assignee: Pfizer Inc., New York, NY (US)

( * ) Notice: Subject to any disclaimer, the term of this patent is extended or adjusted under 35 U.S.C. 154(b) by 140 days.

(21) Appl. No.: 10/313,446

(22) Filed: Dec. 6, 2002

(65) Prior Publication Data

US 2003/0149017 A1 Aug. 7, 2003

Related U.S. Application Data

(63) Continuation of application No. 09/740,385, filed on Dec. 20, 2000, now abandoned, which is a continuation of application No. 09/381,447, filed as application No. PCT/IB98/01229 on Aug. 11, 1998, now abandoned.

(60) Provisional application No. 60/057,094, filed on Aug. 27, 1997.

(51) Int. Cl.
*C07D 471/10* (2006.01)
*C07D 401/10* (2006.01)
*C07D 401/14* (2006.01)
*A61K 31/438* (2006.01)
*A61K 31/4427* (2006.01)

(52) U.S. Cl. ............... 514/278; 514/299; 514/307; 514/318; 514/339; 514/340; 514/352; 546/20; 546/112; 546/148; 546/311; 544/360

(58) Field of Classification Search ............ 546/311, 546/20, 148, 112, 276.7, 276.4; 544/360; 514/318, 352, 278, 307, 299, 339, 340
See application file for complete search history.

(56) References Cited

U.S. PATENT DOCUMENTS

| 5,972,975 A | 10/1999 | Esser et al. ............... 514/352 |
| 6,211,208 B1 | 4/2001 | Lowe, III ............... 514/352 |

FOREIGN PATENT DOCUMENTS

| EP | 0657459 | 6/1995 |
| WO | WO9414780 | 7/1994 |
| WO | WO9511231 | 4/1995 |
| WO | WO9736871 | 10/1997 |
| WO | WO9618616 | 6/1998 |
| WO | WO9824766 | 6/1998 |
| WO | WO9834919 | 8/1998 |
| WO | WO9910339 | 3/1999 |
| WO | WO9911620 | 3/1999 |
| WO | WO0009130 | 2/2000 |

OTHER PUBLICATIONS

Patent Abstracts of Japan, vol. 97, No. 9, Sep. 97 & JP 09 132529 A (ONO Pharmaceutical Co: Ltd.) 5/2 see abstract & Database WPI Week 9730 Derwent Publications Ltd., AN 328451.
Patent Abstracts of Japan, vol. 97, No. 3, Mar. 31, 1997 & JP 08 311028 A (Japan Tobacco Inc).
Bennett et al., Cecil Textbook of Medicine, 1992, 20$^{th}$ Edition.
Hobb et al., Inhibition of nitric oxicide synthase as a potential therapeutic target. Annu Rev. Pharmacol, Toxicol 39: 191–220.
Stavenuiter et al., Synthesis of 5–phenyl–2–pyridinamine, Carcinogenesis, 6(1): 13–19.
Hussaini, et al., Synthesis of substituted 2–aminopyridines, J. Chem. Research, 3:86.

*Primary Examiner*—Mark L. Berch
*Assistant Examiner*—Kahsay Habte
(74) *Attorney, Agent, or Firm*—P. C. Richardson; L. B. Ling; J. A. Jubinsky

(57) ABSTRACT

The present invention relates to 2-aminopyridine derivatives of the formula

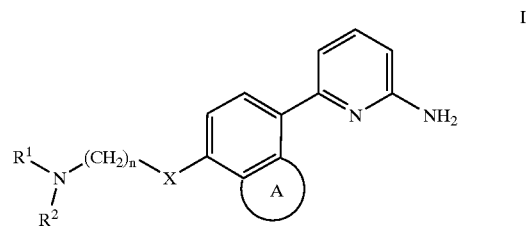

wherein G, $R^1$ and $R^2$ are defined as in the specification, that exhibit activity as nitric oxide synthase (NOS) inhibitors, to pharmaceutical compositions containing them and to their use in the treatment and prevention of central nervous system and other disorders.

4 Claims, No Drawings

2-AMINOPYRIDINES CONTAINING FUSED RING SUBSTITUENTS

The present application is a continuation of U.S. application Ser. No. 09/740,385, filed Dec. 20, 2000 and now abandoned, which is a continuation of U.S. application Ser. No. 09/381,447, filed Sep. 20, 1999 and now abandoned, itself representing the International stage (35 USC section 371) of International Application PCT/IB98/01229, internationally filed on Aug. 11, 1998. The present application and said international applicaton also claim priority to U.S. provisional application No. 60/057,094, filed Aug. 27, 1997.

The present invention relates to certain 2-aminopyridines containing fused ring substituents that exhibit activity as nitric oxide synthase (NOS) inhibitors, to pharmaceutical compositions containing them and to their use in the treatment and prevention of central nervous system disorders, inflammatory disorders, septic shock and other disorders.

There are three known isoforms of NOS—an inducible form (I-NOS) and two constitutive forms referred to as, respectively, neuronal NOS (N-NOS) and endothelial NOS (E-NOS). Each of these enzymes carries out the conversion of arginine to citrulline while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, i.e., inducible NOS (I-NOS), see *Chemical & Engineering News*, Dec. 20, p. 33, (1993). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats, see *Am. J. Physiol.*, 268, p. R286 (1995)). Suppression of adjuvant induced arthritis by selective inhibition of I-NOS is reported in *Eur. J. Pharmacol.*, 273, p. 15–24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat, see *J. Cerebr. Blood Flow Metab.*, 14, p. 924–929 (1994). N-NOS inhibition has also been shown to be effective in antinociception, as evidenced by activity in the late phase of the formalin-induced hindpaw licking and acetic acid-induced abdominal constriction assays, see *Br. J. Pharmacol.*, 110, p. 219–224 (1993). In addition, subcutaneous injection of Freund's adjuvant in the rat induces an increase in NOS-positive neurons in the spinal cord that is manifested in increased sensitivity to pain, which can be treated with NOS inhibitors, see *Japanese Journal of Pharmacology*, 75, p. 327–335 (1997). Finally, opioid withdrawal in rodents has been reported to be reduced by N-NOS inhibition, see *Neuropsychopharmacol.*, 13, p. 269–293 (1995).

SUMMARY OF THE INVENTION

This invention relates to compounds of the formula

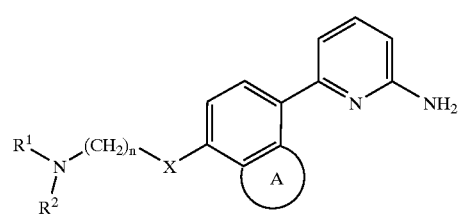

wherein ring A is a fused 5–7 membered saturated or unsaturated ring wherein from zero to two of the ring members are heteroatoms selected, independently, from nitrogen, oxygen and sulfur, with the proviso that no two adjacent ring members can both be heteroatoms;

X is oxygen or a bond;

n is an integer from two to six; and $R^1$ and $R^2$ are selected, independently, from ($C_1$–$C_6$) alkyl, aryl, tetrahydronaphthalene and aralkyl, wherein said aryl and the aryl moiety of said aralkyl is phenyl or naphthyl and the alkyl moiety is straight or branched and contains from 1 to 6 carbon atoms, and wherein said ($C_1$–$C_6$) alkyl, said aryl, said tetrahydronaphthalene and the aryl moiety of said aralkyl may optionally be substituted with from one to three substituents, preferably from zero to two substituents, that are selected, independently, from halo (e.g., chloro, fluoro, bromo, iodo), nitro, hydroxy, cyano, amino, ($C_1$–$C_4$) alkoxy, and ($C_1$–$C_4$) alkylamino;

or $R^1$ and $R^2$ form, together with the nitrogen to which they are attached, a piperazine, azetidine, piperidine or pyrrolidine ring or an azabicyclic ring containing from 6 to 14 ring members, from 1 to 3 of which are nitrogen and the rest of which are carbon, wherein examples of said azabicyclic rings are the following

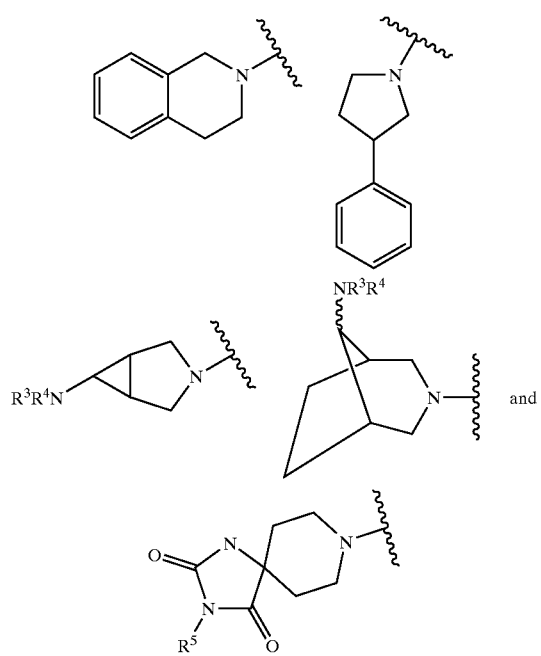

also $R^1$ or $R^2$ may be connected onto the $(CH_2)_n$ group to form a ring of from 4 to 7 members;

wherein $R^3$ and $R^4$ are selected from hydrogen, $(C_1-C_6)$ alkyl, phenyl, naphthyl, $(C_1-C_6)$alkyl-C(=O)—, HC(=O)—, $(C_1-C_6)$alkoxy-C(=O)—, naphthyl-C(=O)—, and $R^6R^7NC(=O)$— wherein $R^6$ and $R^7$ are selected, independently, from hydrogen and $(C_1-C_6)$ alkyl;

$R^5$ is selected from hydrogen, $(C_1-C_6)$alkyl, phenyl, naphthyl, phenyl-$(C_1-C_6)$alkyl- and naphthyl$(C_1-C_6)$alkyl-;

and wherein said piperazine, azetidine, piperidine and pyrrolidine rings may optionally be substituted with one or more substituents, preferably with from zero to two substituents that are selected, independently, from $(C_1-C_6)$ alkyl, amino, $(C_1-C_6)$ alkylamino, [di-$(C_1-C_6)$alkyl]amino, phenyl substituted 5 to 6 membered heterocyclic rings containing from 1 to 4 rings nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents, preferably with from zero to two substituents, that are selected, independently, from halo, $(C_1-C_3)$alkyl, $(C_1-C_3)$alkoxy, nitro, amino, cyano, $CF_3$ and $OCF_3$;

and the pharmaceutically acceptable salts of such compounds.

The following compounds are preferred compounds of the invention:

6-[4-(2-Dimethylamino-ethoxy)-naphthalen-1-yl]-pyridin-2-ylamine;
6-[4-(2-Pyrrolidin-1-yl-ethoxy)-naphthalen-1-yl]-pyridin-2-ylamine;
6-(4-{2-[(Benzo[1,3]dioxol-5-ylmethyl)-amino]-ethoxy}-naphthalen-1-yl)-pyridin-2-ylamine;
6-{4-[2-(6,7-Dimethoxy-3,4-dihydro-1H-isoquinolin-2-yl)-ethoxy]-naphthalen-1-yl}-pyridin-2-ylamine;
3-{2-[4-(6-Amino-pyridin-2-yl)-naphthalen-1-yloxy]-ethyl}-3-aza-bicyclo[3.1.0]hex-6-ylamine;
6-{4-[2-(4-Phenethyl-piperazin-1-yl)-ethoxy]-naphthalen-1-yl}-pyridin-2-ylamine;
6-{4-[2-(3-Amino-pyrrolidin-1-yl)-ethoxy]-naphthalen-1-yl}-pyridin-2-ylamine;
6-[4-(1-Benzyl-piperidin-4-yloxy)-naphthalen-1-yl]-pyridin-2-ylamine;
6-[4-(1-Benzyl-pyrrolidin-3-yloxy)-naphthalen-1-yl]-pyridin-2-ylamine;
6-[4-(Piperidin-4-yloxy)-naphthalen-1-yl]-pyridin-2-ylamine;
6-[4-(Pyrrolidin-3-yloxy)-naphthalen-1-yl]-pyridin-2-ylamine;
6-[4-(1-Isobutyl-piperidin-4-yloxy)-naphthalen-1-yl]-pyridin-2-ylamine;
6-[4-(1-Furan-2-ylmethyl-piperidin-4-yloxy)-naphthalen-1-yl]-pyridin-2-ylamine;
6-[4-(1-Isobutyl-pyrrolidin-3-yloxy)-naphthalen-1-yl]-pyridin-2-ylamine;
6-[4-(1-Furan-2-ylmethyl-pyrrolidin-3-yloxy)-naphthalen-1-yl]-pyridin-2-ylamine;
6-[4-(2-Morpholin-4-yl-ethoxy)-naphthalen-1-yl]-pyridin-2-ylamine;
6-[4-(2-Diisopropylamino-ethoxy)-naphthalen-1-yl]-pyridin-2-ylamine;
6-[4-(1-Methyl-piperidin-4-yloxy)-naphthalen-1-yl]-pyridin-2-ylamine;
6-[4-(1-Methyl-pyrrolidin-3-yloxy)-naphthalen-1-yl]-pyridin-2-ylamine;
6-[4-(3-Dimethylamino-propoxy)-naphthalen-1-yl]-pyridin-2-ylamine;
6-[4-(1-Aza-bicyclo[2.2.2]oct-3-yloxy)-naphthalen-1-yl]-pyridin-2-ylamine;
6-[4-(2-Piperidin-1-yl-ethoxy)-naphthalen-1-yl]-pyridin-2-ylamine
6-{4-[2-(3,4-Dihydro-1H-isoquinolin-2-yl)-ethoxy]-naphthalen-1-yl}-pyridin-2-ylamine;
6-{4-[2-(4-Dimethylamino-piperidin-1-yl)-ethoxy]-naphthalen-1-yl}-pyridin-2-ylamine;
6-{4-[2-(tert-Butyl-methyl-amino)-ethoxy]-naphthalen-1-yl}-pyridin-2-ylamine;
6-{4-[2-(4-Methyl-piperazin-1-yl)-ethoxy]-naphthalen-1-yl}-pyridin-2-ylamine;
6-{4-[2-(4-Phenyl-piperidin-1-yl)-ethoxy]-naphthalen-1-yl}-pyridin-2-ylamine;
6-{4-[2-(7,8-Dihydro-5H-[1,3]dioxolo[4,5-g]isoquinolin-6-yl)-ethoxy]-naphthalen-1-yl}-pyridin-2-ylamine;
6-[4-(Piperidin-2-ylmethoxy)-naphthalen-1-yl]-pyridin-2-ylamine;
6-[4-(1-Methyl-piperidin-2-ylmethoxy)-naphthalen-1-yl]-pyridin-2-ylamine;
6-[4-(1-Methyl-piperidin-3-ylmethoxy)-naphthalen-1-yl]-pyridin-2-ylamine;
6-[4-(2-Amino-cyclohexyloxy)-naphthalen-1-yl]-pyridin-2-ylamine;
6-[4-(Piperidin-3-ylmethoxy)-naphthalen-1-yl]-pyridin-2-ylamine;
6-[4-(1-Isobutyl-azetidin-3-yloxy)-naphthalen-1-yl]-pyridin-2-ylamine;
6-[4-(1-Furan-2-ylmethyl-azetidin-3-yloxy)-naphthalen-1-yl]-pyridin-2-ylamine;
6-[4-(8-Methyl-8-aza-bicyclo[3.2.1]oct-3-yloxy)-naphthalen-1-yl]-pyridin-2-ylamine;
6-[4-(Azetidin-3-yloxy)-naphthalen-1-yl]-pyridin-2-ylamine;
6-[4-(1-Methyl-pyrrolidin-2-ylmethoxy)-naphthalen-1-yl]-pyridin-2-ylamine;
6-[4-(Azetidin-2-ylmethoxy)-naphthalen-1-yl]-pyridin-2-ylamine;
6-[7-(2-Dimethylamino-ethoxy)-indan-4-yl]-pyridin-2-ylamine;
6-[7-(2-Pyrrolidin-1-yl-ethoxy)-indan-4-yl]-pyridin-2-ylamine;
6-{7-[2-(Benzyl-methyl-amino)-ethoxy]-indan-4-yl}-pyridin-2-ylamine;
6-{7-[2-(4-Phenethyl-piperazin-1-yl)-ethoxy]-indan-4-yl}-pyridin-2-ylamine;
6-{7-[2-(4-Isobutyl-piperazin-1-yl)-ethoxy]-indan-4-yl}-pyridin-2-ylamine;
6-[7-(2-Morpholin-4-yl-ethoxy)-indan-4-yl]-pyridin-2-ylamine;
6-[7-(2-Diisopropylamino-ethoxy)-indan-4-yl]-pyridin-2-ylamine;
6-{7-[2-(7,8-Dihydro-5H-[1,3]dioxolo[4,5-g]isoquinolin-6-yl)-ethoxy]-indan-4-yl}-pyridin-2-amine;
6-{7-[2-(4-Methyl-piperazin-1-yl)-ethoxy]-indan-4-yl}-pyridin-2-ylamine;
6-{7-[2-(tert-Butyl-methyl-amino)-ethoxy]-indan-4-yl}-pyridin-2-ylamine;
6-{7-[2-(4-Dimethylamino-piperidin-1-yl)-ethoxy]-indan-4-yl}-pyridin-2-ylamine;
6-[8-(2-Dimethylamino-ethoxy)-1,2,3,4-tetrahydro-1,4-methano-naphthalen-5-y]-pyridin-2-ylamine;
6-[8-(2-Pyrrolidin-1-yl-ethoxy)-1,2,3,4-tetrahydro-1,4-methano-naphthalen-5-yl]-pyridin-2-ylamine;
6-[4-(2-Dimethylamino-ethoxy)-5,6,7,8-tetrahydro-naphthalen-1-yl]-pyridin-2-ylamine;
6-[4-(2-Pyrrolidin-1-yl-ethoxy)-5,6,7,8-tetrahydro-naphthalen-1-yl]-pyridin-2-ylamine;
6-{4-[2-(tert-Butyl-methyl-amino)-ethoxy]-5,6,7,8-tetrahydro-naphthalen-1-yl}-pyridin-2-ylamine;

6-[4-(2-Diisopropylamino-ethoxy)-5,6,7,8-tetrahydro-naphthalen-1-yl]-pyridin-2-ylamine;
6-[4-(2-Diethylamino-ethoxy)-5,6,7,8-tetrahydro-naphthalen-1-yl]-pyridin-2-ylamine;
6-{4-[2-(3,4-Dihydro-1H-isoquinolin-2-yl)-ethoxy]-5,6,7,8-tetrahydro-naphthalen-1-yl}-pyridin-2-ylamine;
6-[4-(2-Piperidin-1-yl-ethoxy)-5,6,7,8-tetrahydro-naphthalen-1-yl]-pyridin-2-ylamine;
6-[4-(2-Morpholin-4-yl-ethoxy)-5,6,7,8-tetrahydro-naphthalen-1-yl]-pyridin-2-ylamine;
6-{4-[2-(7,8-Dihydro-5H-[1,3]dioxolo[4,5-g]isoquinolin-6-yl)-ethoxy]-5,6,7,8-tetrahydro-naphthalen-1-yl}-pyridin-2-ylamine;
6-{4-[2-(4-Methyl-piperazin-1-yl)-ethoxy]-5,6,7,8-tetrahydro-naphthalen-1-yl}-pyridin-2-ylamine;
6-{4-[2-(4-Dimethylamino-piperidin-1-yl)-ethoxy]-5,6,7,8-tetrahydro-naphthalen-1-yl}-pyridin-2-ylamine;
6-{4-[2-(7,8-Dihydro-5H-[1,3]dioxolo[4,5-g]isoquinolin-6-yl)-ethoxy]-5,6,7,8-tetrahydro-naphthalen-1-yl}-pyridin-2-ylamine;
6-[4-(1-Isobutyl-piperidin-3-ylmethoxy)-5,6,7,8-tetrahydro-naphthalen-1-yl]-pyridin-2-ylamine;
6-[4-(1-Methyl-piperidin-3-ylmethoxy)-5,6,7,8-tetrahydro-naphthalen-1-yl]-pyridin-2-ylamine;
6-{4-[2-(2-Diethylamino-ethoxy)-ethoxy]-5,6,7,8-tetrahydro-naphthalen-1-yl}-pyridin-2-ylamine;
6-[4-(Piperidin-3-ylmethoxy)-5,6,7,8-tetrahydro-naphthalen-1-yl]-pyridin-2-ylamine;
6-[4-(2-Amino-cyclohexyloxy)-5,6,7,8-tetrahydro-naphthalen-1-yl]-pyridin-2-ylamine;
6-[4-(Pyrrolidin-2-ylmethoxy)-5,6,7,8-tetrahydro-naphthalen-1-yl]-pyridin-2-ylamine; and
6-[4-(2-Dimethylamino-ethoxy)-6,7,8,9-tetrahydro-5H-benzocyclohepten-1-yl]-pyridin-2-ylamine;
and the pharmaceutically acceptable salts of the foregoing compounds.

The following are additional examples of compounds of this invention:
6-[4-(2-Amino-cyclopentyloxy)-5,6,7,8-tetrahydro-naphthalen-1-yl]-pyridin-2-ylamine;
6-[4-(2-Amino-cyclobutyloxy)-5,6,7,8-tetrahydro-naphthalen-1-yl]-pyridin-2-ylamine;
6-[4-(2-Amino-cyclopropyloxy)-5,6,7,8-tetrahydro-naphthalen-1-yl]-pyridin-2-ylamine;
6-[4-(3-Amino-cyclohexyloxy)-5,6,7,8-tetrahydro-naphthalen-1-yl]-pyridin-2-ylamine;
6-[4-(3-Amino-cyclopentyloxy)-5,6,7,8-tetrahydro-naphthalen-1-yl]-pyridin-2-ylamine;
6-[4-(3-Amino-cyclobutyloxy)-5,6,7,8-tetrahydro-naphthalen-1-yl]-pyridin-2-ylamine;
6-[4-(4-Amino-cyclohexyloxy)-5,6,7,8-tetrahydro-naphthalen-1-yl]-pyridin-2-ylamine;
6-[4-(2-Amino-cyclopentyloxy)-naphthalen-1-yl]-pyridin-2-ylamine;
6-[4-(2-Amino-cyclobutyloxy)-naphthalen-1-yl]-pyridin-2-ylamine;
6-[4-(2-Amino-cyclopropyloxy)-naphthalen-1-yl]-pyridin-2-ylamine;
6-[4-(3-Amino-cyclohexyloxy)-naphthalen-1-yl]-pyridin-2-ylamine;
6-[4-(3-Amino-cyclopentyloxy)-naphthalen-1-yl]-pyridin-2-ylamine;
6-[4-(3-Amino-cyclobutyloxy)-naphthalen-1-yl]-pyridin-2-ylamine;
6-[4-(4-Amino-cyclohexyloxy)-naphthalen-1-yl]-pyridin-2-ylamine;
6-[4-(2-Amino-cyclopentyloxy)-indan-4-yl]-pyridin-2-ylamine;
6-[4-(2-Amino-cyclobutyloxy)-indan-4-yl]-pyridin-2-ylamine;
6-[4-(2-Amino-cyclopropyloxy)-indan-4-yl]-pyridin-2-ylamine;
6-[4-(3-Amino-cyclohexyloxy)-indan-4-yl]-pyridin-2-ylamine;
6-[4-(3-Amino-cyclopentyloxy)-indan-4-yl]-pyridin-2-ylamine;
6-[4-(3-Amino-cyclobutyloxy)-indan-4-yl]-pyridin-2-ylamine;
6-[4-(4-Amino-cyclohexyloxy)-indan-4-yl]-pyridin-2-ylamine;
6-[4-Piperidin-3-ylmethoxy)-6,7,8,9-tetrahydro-5H-benzocyclohepten-1-yl]-pyridin-2-ylamine;
6-[4-(2-Pyrrolidinyl-ethoxy)-6,7,8,9-tetrahydro-5H-benzocyclohepten-1-yl]-pyridin-2-ylamine;
6-[4-(2-Amino-cyclohexyloxy)-6,7,8,9-tetrahydro-5H-benzocyclohepten-1-yl]-pyridin-2-ylamine;
6-[4-(2-(4-Dimethylamino-piperidin-1-yl)-ethoxy))-6,7,8,9-tetrahydro-5H-benzocyclohepten-1-yl]-pyridin-2-ylamine; and
6-[4-(2-(4-Methyl-piperazin-1-yl)-ethoxy))-6,7,8,9-tetrahydro-5H-benzocyclohepten-1-yl]-pyridin-2-ylamine.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid, addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "one or more substituents", as used herein, refers to a number of substituents that equals from one to the maximum number of substituents possible based on the number of available bonding sites The terms "halo" and "halogen", as used herein, unless otherwise indicated, include chloro, fluoro, bromo and iodo.

Examples of more specific embodiments of the present invention include:
(a) compounds of the formula I wherein ring A is pyrrolo;
(b) compounds of the formula I wherein ring A is pyrido;
(c) compounds of the formula I wherein X is a bond;
(d) compounds of the formula I wherein ring A is pyrimido;
(e) compounds of the formula I wherein n is 2 or 3;
(f) compounds of the formula I wherein X is oxygen;
(g) compounds of the formula I wherein $R^1$ and $R^2$ are selected, independently, from $(C_1-C_6)$alkyl;
(h) compounds of the formula I wherein $R^1$ and $R^2$ do not form a ring with the nitrogen to which they are attached;
(i) compounds of the formula I wherein $R^1$ and $R^2$ form, together with the nitrogen to which they are attached, a piperazine, azetidine, piperidine or pyrrolidine ring;
(j) compounds of the formula I wherein $R^1$ is selected from $(C_1-C_6)$alkyl and $R^2$ is selected from aryl, tetrahydronaphthalene and aralkyl; and
(k) compounds of the formula I wherein ring A is thieno or thiazolo.

The present invention also relates to a pharmaceutical composition for treating or preventing a condition selected from the group consisting of migraine inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, depression (e.g., major depressive disorder and dysthymia, Parkinson's disease, Alzheimer's disease, chemical dependencies and addiction (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising an amount of a compound of the formula I, or a pharmaceutically acceptable salt thereof that is effective in treating or preventing such condition, and a pharmaceutically acceptable carrier.

The present invention also relates to a method of treating or preventing a condition selected from the group consisting of migraine inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, depression (e.g., major depressive disorder and dysthymia), Parkinson's disease, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising administering to said mammal an amount of a compound of the formula I, or a pharmaceutically acceptable salt thereof, that is effective in treating or preventing such condition.

The present invention also relates to a pharmaceutical composition for inhibiting nitric oxide synthase (NOS) in a mammal, including a human, comprising an NOS inhibiting effective amount of a compound of the formula I, or a pharmaceutically acceptable salt thereof and a pharmaceutically acceptable carrier.

The present invention also relates to a method of inhibiting NOS in a mammal, including a human, comprising administering to said mammal a NOS inhibiting effective amount of a compound of the formula I, or a pharmaceutically acceptable salt thereof.

The present invention also relates to a pharmaceutical composition for treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, depression (e.g., major depressive disorder and dysthymia), Parkinson's disease, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising a NOS inhibiting effective amount of a compound of the formula I, or a pharmaceutically acceptable salt thereof and a pharmaceutically acceptable carrier.

The present invention also relates to a method of treating or preventing a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, depression (e.g., major depressive disorder and dysthymia), Parkinson's disease, Alzheimer's disease, chemical dependencies and addictions (e.g., dependencies on drugs, alcohol or nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, glaucoma, macular degeneration, diabetic neuropathy, diabetic nephropathy and cancer in a mammal, including a human, comprising administering to said mammal a NOS inhibiting effective amount of a compound of the formula II, or a pharmaceutically acceptable salt thereof.

Compounds of formula I may contain chiral centers and therefore may exist in different enantiomeric and diastereomeric forms. This invention relates to all optical isomers and all stereoisomers of compounds of the formula I and mixtures thereof, and to all pharmaceutical compositions and methods of treatment defined above that contain or employ them, respectively.

Formula I above includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of the formula I may be prepared as described in the following reaction schemes and discussion. Unless otherwise indicated, ring A, X, n, $R^1$, $R^2$, $R^3$, $R^4$, $R^5$, $R^6$ and $R^7$ and structural formula I in the reaction schemes and discussion that follow are defined as above.

SCHEME 1

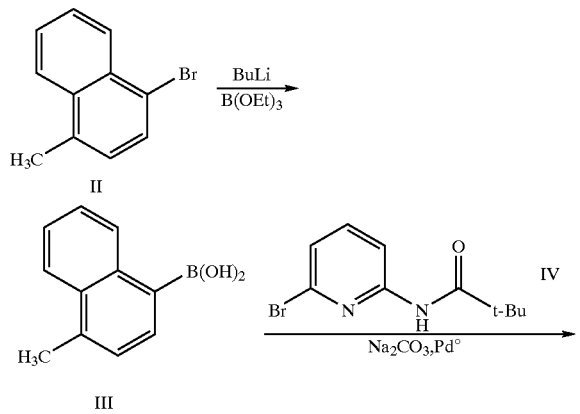

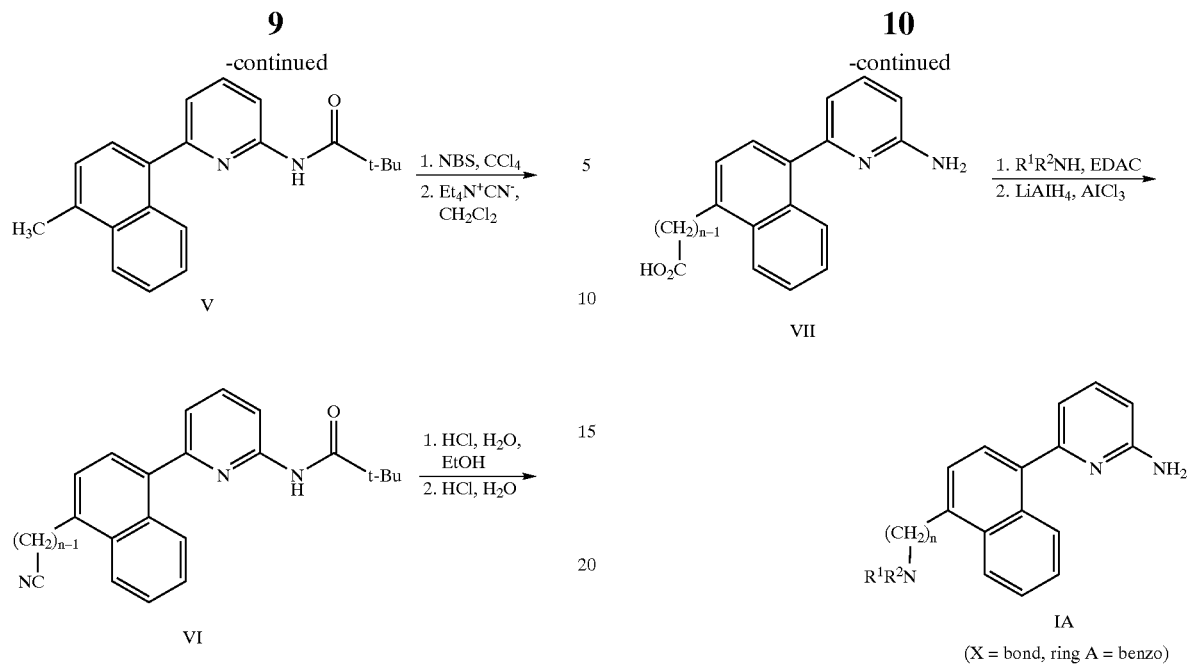
SCHEME 2
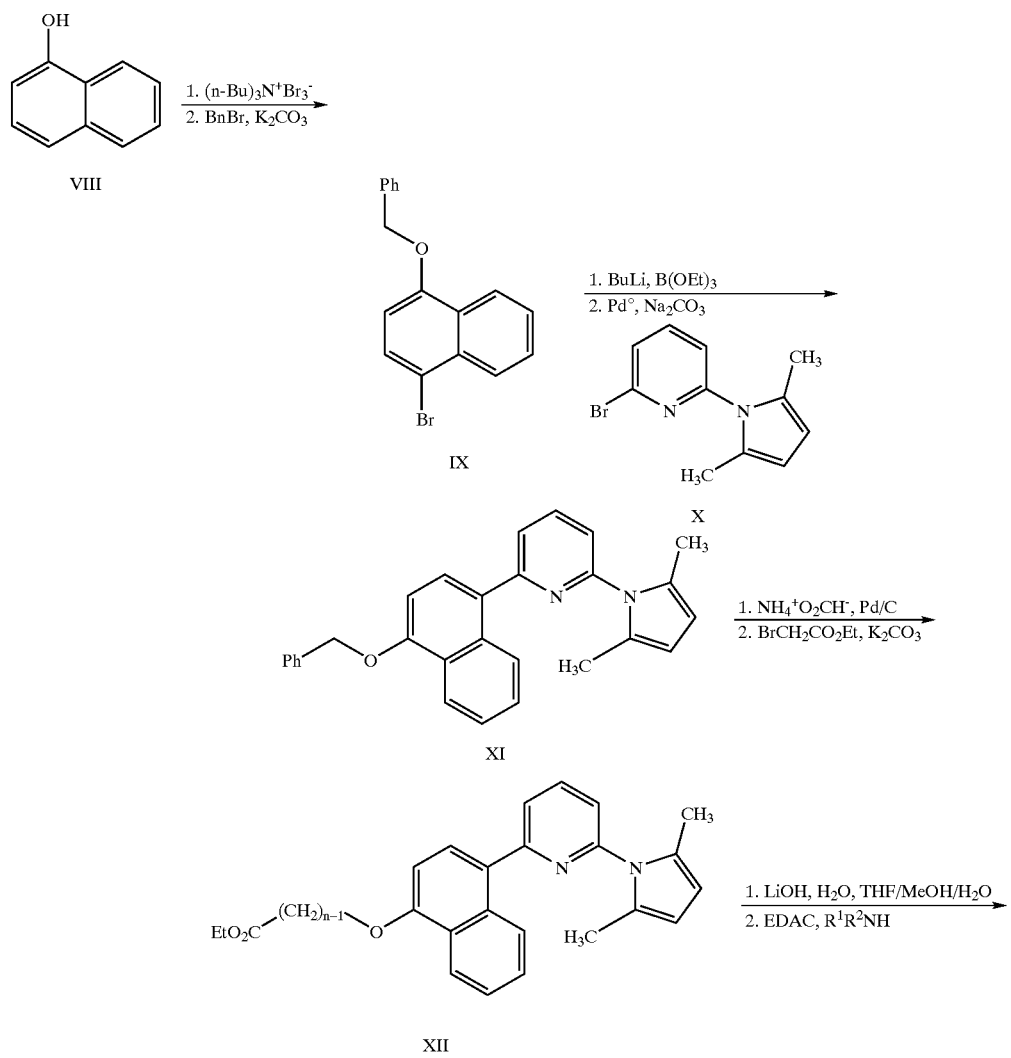

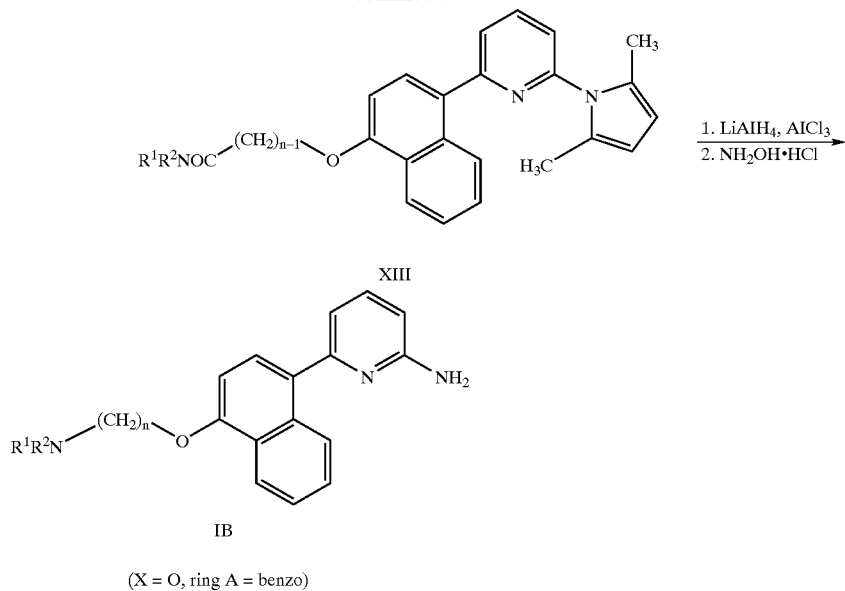

XIII

IB (X = O, ring A = benzo)

SCHEME 3

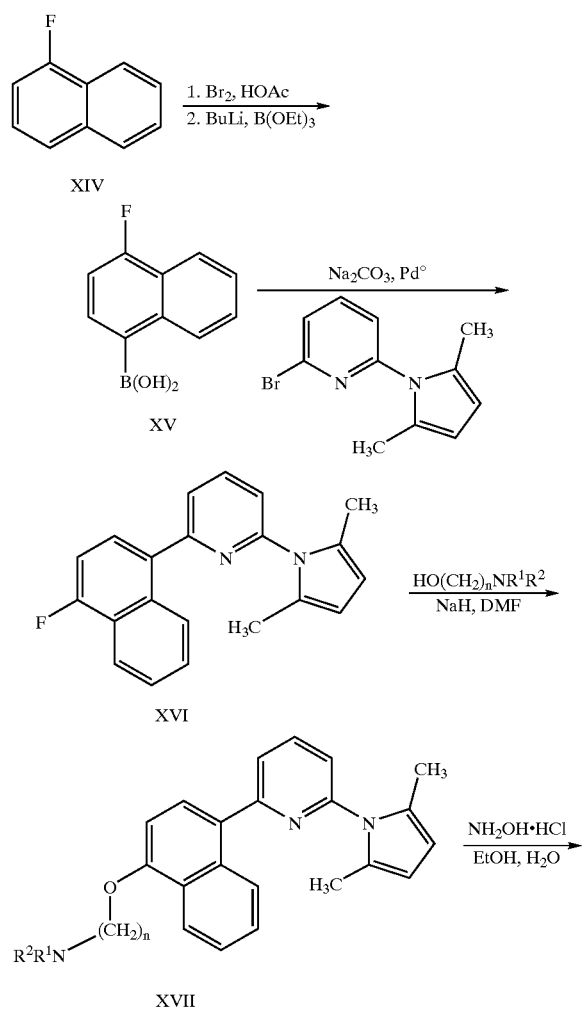

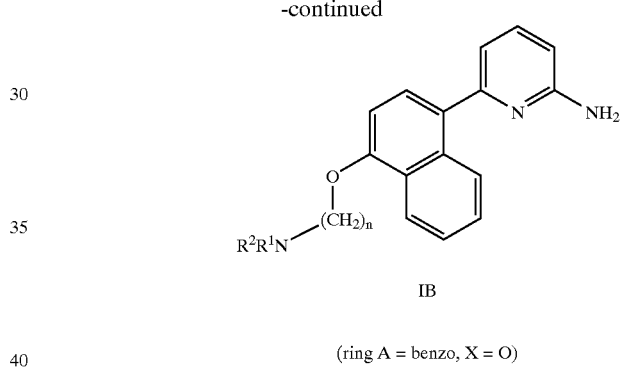

IB (ring A = benzo, X = O)

Scheme 1 illustrates a method of preparing compounds of the formula I wherein X is a bond and ring A is benzo. Schemes 2 and 3 illustrate methods of preparing compounds of the formula I wherein X is oxygen and ring A is benzo. The starting materials used in the procedures of Schemes 1 and 2 are either commercially available, known in the art or readily obtainable from known compounds by methods that will be apparent to those skilled in the art.

Referring to Scheme 1, the compound of formula II is cooled to about −70° C. in dry tetrahydrofuran (THF), and then a solution of n-butyl lithium is added to it. The resulting solution is then treated with triethyl borate and allowed to warm to room temperature to form the compound of formula III.

The compound of formula III is reacted with the compound of formula IV to form the compound of formula V. This reaction is generally carried out in an aqueous ethanol solvent, in the presence of sodium carbonate and tetrakistriphenylphoshine palladium, at about the reflux temperature.

The compound of the formula VI can be formed in the following manner. First, the compound of formula V is reacted with N-bromosuccinimide (NBS) and bis-(1-cyano-1-aza)-cyclohexane in carbon tetrachloride and refluxed for about 8 hours, with additional portions of the initiator being added at about 1, 2 and 4 hours. After evaporation of the solvent, the product of this reaction is reacted with triethylammonium cyanide in methylene chloride at about room temperature to form the compound of formula VI.

Saturation of a solution of the compound of formula VI in ethanol with hydrogen chloride, followed by refluxing the mixture and then heating in aqueous hydrochloric acid, yields the compound of formula VII.

The compound of the formula VII that is formed in the preceding step can be converted into the compound of formula IA in the following manner. First, the compound of formula VII is reacted with the appropriate compound of the formula $R^2R^1NH$ and N-ethyl-N-dimethylaminopropyl carbodiimide (EDAC) in the presence of a base. Examples of suitable bases are those selected from trialkylamines, alkali metal carbonates and alkaline earth metal carbonates. This reaction is typically conducted in a solvent such as acetonitrile, methylene chloride or N,N-dimethylformamide (DMF), at a temperature from about room temperature to about 100° C., preferably at about room temperature. Preferably, the reaction is conducted in the presence of a catalytic additive such as N-hydroxysuccinamide or hydroxybenzotriazole.

The product of the foregoing reaction is then reduced using methods well known to those of skill in the art. For example, the reduction can be carried out using lithium aluminum hydride in tetrahydrofuran, with or without aluminum chloride, or using borane methyl sulfide in tetrahydrofuran, at a temperature of about −78° C. to about 0° C., preferably at about −70° C., to yield the desired compound of formula IA.

Referring to scheme 2, the compound of formula VIII is reacted with tetrabutylammonium tribromide in 1,2-dichloroethane at about room temperature. The product of this reaction is then treated with benzyl bromide and potassium carbonate in a solvent such as acetonitite, at about the reflux temperature of the reaction mixture, to form the compound of formula IX.

The compound of formula IX is then converted into 1-benzyloxy-naphthalene-4-boronic acid by the procedure described above for preparing the boronic acid derivative of formula III in Scheme 1.

Reaction of 1-benzyoxy-napthalene-4-boronic acid with the compound of formula X in an ethanol solvent, in the presence of sodium carbonate and tetrakistriphenyl palladium, at about the reflux temperature of the reaction mixture, yields the compound of formula XI.

The compound of formula XI can be converted into the compound of formula XIII using the following two step process. The compound of formula XI is reacted with ammonium formate and ten percent palladium on carbon, in an ethanol solvent, at about the reflux temperature of the reaction mixture, to yield the analogous compound to that having formula XI, wherein the benzyloxy group of formula XI is replaced with a hydroxy group. The compound of formula XII is then formed by reacting the above hydroxy derivative with 2-bromoethylacetate and potassium carbonate in acetonitrile at about the reflux temperature of the reaction mixture.

Basic hydrolysis of the compound of formula XII, followed by reaction with N-ethyl-N-3-dimethylaminopropylcarbodiimide (EDAC) and the appropriate compound having the formula $R^1R^2NH$ yields the desired compound of the formula XIII. The base hydrolysis is typically carried out using an alkali metal or alkaline earth metal hydroxide in a mixture of THF, methanol and water at about room temperature. The reaction with $R^1R^2NH$ and EDAC is generally carried out using the procedure described above for the preparation of compounds of the formula IA from those of formula VII in Scheme 1.

The compound of formula XIII can be converted into the desired compound of formula IB as follows. The compound of formula XIII is reduced to form the corresponding compound wherein the carbonyl group is replaced by a methylene group, after which the 2,5-dimethylpyrrolyl protecting group is removed. The reduction can be carried out using methods well known to those of skill in the art, for example, using lithium aluminum hydride in tetrahydrofuran, with or without aluminum chloride, or using borane methyl sulfide in tetrahydrofuran, at a temperature of about −78° C. to about 0° C., preferably at about −70° C.

Removal of the 2,5-dimethylpyrrolyl protecting group can be accomplished by reaction with hydroxylamine hydrochloride. This reaction is generally carried out in an alcoholic or aqueous alcoholic solvent, at a temperature from about room temperature to about the reflux temperature of the reaction mixture, preferably at about the reflux temperature, for about 8 to about 72 hours.

Compounds of the formula I that are identical to those of formula IB but for the fact that ring A is other than benzo can be prepared in an analogous fashion, starting with the appropriate compound that is analogous to that of formula VIII, wherein the unsubstituted benzo ring of formula VIII is replaced by a ring other than benzo that is within the definition of ring A.

Referring to Scheme 3, the known 1-fluoronaphthalene (XIV) is brominated with bromine in acetic acid at a temperature from about room temperature to about the reflux temperature of the reaction mixture for about 1 to about 48 hours, and the bromide cooled to about −70° C. in dry tetrahydrofuran (THF), and then a solution of n-butyl lithium is added to it. The resulting solution is then treated with triethyl borate and allowed to warm to room temperature to form the compound of formula XV. The compound of formula XV is reacted with the compound of formula IV to form the compound of formula XVI. This reaction is generally carried out in an aqueous ethanol solvent, in the presence of sodium carbonate and tetrakistriphenylphoshine palladium, at about the reflux temperature. The compound of formula XVI is then treated with an alkali metal alkoxide prepared from a compound of the formula $HO(CH_2)_nNR^1R^2$ and sodium hydride in a polar solvent such as dimethylformamide, at a temperature from room temperature to 140° C. for about 1 to about 48 hours. This reaction produces the corresponding compound of formula XVII, which is then deblocked to remove the 2,5-dimethylpyrrolyl protecting group by reaction with hydroxylamine hydrochloride. This reaction is generally carried out in an alcoholic or aqueous alcoholic solvent, at a temperature from about room temperature to about the reflux temperature of the reaction mixture, preferably at about the reflux temperature, for about 8 to about 72 hours.

Compounds of the formula I that are identical to those of formula IA and IB but for the fact that ring A is other than benzo can be prepared in an analogous fashion, starting with the appropriate starting materials that are analogous to those of formulas VII and XIV, on Schemes 1, 2 and 3 respectively, wherein the unsubstituted benzo ring of such starting materials is replaced by a ring other than benzo that is within the definition of ring A.

The preparation of other compounds of the formula I not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formulae I ("the active compounds of this invention") which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compounds of this invention and their pharmaceutically acceptable salts are useful as NOS inhibitors i.e., they possess the ability to inhibit the NOS enzyme in mammals, and therefore they are able to function as therapeutic agents in the treatment of the aforementioned disorders and diseases in an afflicted mammal.

The active compounds of this invention and their pharmaceutically acceptable salts can be administered via either the oral, parenteral or topical routes. In general, these compounds are most desirably administered in dosages ranging from about 0.01 to about 250 mg per day, in single or divided doses (i.e., from 1 to 4 doses per day), although variations will necessarily occur depending upon the species, weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may be done by way of creams, jellies, gels, pastes, patches, ointments and the like, in accordance with standard pharmaceutical practice.

The ability of compounds of the formulae I to inhibit NOS may be determined using procedures described in the literature. The ability of compounds of the formulae I to inhibit endothelial NOS may be determined by using the procedures described by Schmidt et al. in *Proc. Natl. Acad. Sci. U.S.A.*, 88, pp. 365–369 (1991) and by Pollock et al., in *Proc. Natl. Acad. Sci. U.S.A.*, 88, pp. 10480–10484 (1991). The ability of compounds of the formulae I to inhibit inducible NOS may be determined using the procedures described by Schmidt et al., in *Proc. Natl. Acad. Sci. U.S.A.*, 88 pp. 365–369 (1991) and by Garvey et al. in *J. Biol. Chem.*, 269, pp. 26669–26676 (1994). The ability of the compounds of the formulae I to inhibit neuronal NOS may be determined using the procedure described by Bredt and Snyder in *Proc. Natl. Acad. Sci. U.S.A.*, 87, 682–685 (1990).

Of sixteen compounds of the formula I that were tested, all exhibited an $IC_{50} < 10$ $\mu$M for inhibition of either inducible or neuronal NOS.

The present invention is illustrated by the following examples. It will be understood, however, that the invention is not limited to the specific details of these examples.

EXAMPLE 1

6-{4-[2-(4-Phenethyl-piperazin-1-yl)-ethyl]-naphthalen-1-yl)-pyridin-2-ylamine

N-t-Butylcarbonyl-6-bromo-pyridyl-2-amine

To a 125 mL round-bottomed flask equipped with $N_2$ inlet were added 0.865 g (5 mmol) 6-bromo-2-aminopyridine, 0.677 mL (5.5 mmol) trimethylacetyl chloride, 15 mL dry acetonitrile, and 1.045 mL (7.5 mmol) triethylamine. The reaction was stirred at room temperature for 14 hours, poured into water, and stirred until a solid precipitate had formed. The solid was filtered, washed with water, and dried to afford 1.04 g (81%), mp 87–90° C.

$^1$H-NMR (δ, $CDCl_3$): 1.28 (s, 9H), 7.17 (d, J=8, 1H), 7.52 (t, J=8, 1H), 8.00 (bs, 1H), 8.19 (d, J=8, 1H).

$^{13}$C-NMR (δ, $CDCl_3$): 27.3, 39.8, 112.2, 123.3, 139.0, 140.5, 151.6, 177.1.

B. 4-Methylnaphthalene-1-boronic acid

To a 125 mL round-bottomed flask equipped with $N_2$ inlet were added 1.78 g (11.4 mmol) 1-bromo-4-methylnaphthalene and 20 mL dry tetrahydrofuran. The solution was cooled to −70° C., and 5.49 mL (13.7 mmol) of a 2.5M solution of n-butyl lithium in hexane was added over 5 minutes, and the reaction stirred at −70° C. for 10 minutes. The solution was then treated with 2.34 mL (13.7 mmol) triethyl borate, stirred 5 minutes at −70° C., then warmed to room temperature and stirred 40 hours. The reaction was quenched with aqueous ammonium chloride solution, poured into 0.5 N hydrochloric acid, and extracted into ethyl acetate. The organic layer was washed with brine, dried over sodium sulfate, and evaporated to a white solid after trituration with hexane, mp 224–228° C., 1.9 g (90%).

$^1$H-NMR (δ, $CDCl_3$): 2.63 (s, 3H), 7.25 (m, 1H), 7.3–7.5 (m, 3H), 7.75 (m, 1H), 7.95 (m, 1H).

$^{13}$C-NMR (δ, $CDCl_3$): 19.4, 124.5, 125.5, 125.7, 126.0, 128.5, 128.9, 129.9, 131.6, 134.9, 135.3.

C. N-t-Butylcarbonyl-6-(4-methylnaphthalen-1-yl)-pyridin-2-ylamine

To a 100 mL round-bottomed flask equipped with condenser and $N_2$ inlet were added 975 mg (3.795 mmol) N-t-butylcarbonyl-6-bromo-pyridyl-2-amine, 706 mg (3.795 mmol) 4-methylnaphthalene-1-boronic acid, 1.61 g (15.18 mmol) sodium carbonate, 50 mg (0.04 mmol) tetrakistriphenylphosphine palladium, 18 mL ethanol, and 2 mL water, and the reaction heated at 80° C. for 13 hours. TLC showed a major spot at $R_f$=0.2 in 15% ethyl acetate in hexane, and LCMS showed a major peak at P+1=319. The reaction was cooled, poured into water, and extracted into ethyl acetate. The organic layer was washed with water and brine, dried over sodium sulfate, and evaporated. The residue was chromatographed on silica gel using hexane/ethyl acetate as eluant to afford 1.25 g (~100%) of a foam.

$^1$H-NMR (δ, $CDCl_3$): 1.32 (s, 9H), 2.73 (s, 3H), 7.25 (m, 1H), 7.3–7.5 (m, 4H), 7.81 (t, J=8, 1H), 8.00 (d, J=8, 1H), 8.05 (d, J=8, 1H), 8.145 (bs, 1H), 8.31 (d, J=8, 1H).

$^{13}$C-NMR (δ, $CDCl_3$): 19.7, 27.5, 60.4, 112.1, 121.1, 124.4, 125.8, 126.08, 126.11, 126.16, 126.9, 131.1, 132.9, 135.3, 1338.7, 151.3, 157.8, 177.3.

MS (%): 319 (parent+1, 100).

D. N-t-Butylcarbonyl-6-(4-cyanomethylnaphthalen-1-yl)-pyridin-2-ylamine

To a 100 mL round-bottomed flask equipped with condenser and $N_2$ inlet were added 1.21 g (3.795 mmol) N-t-butylcarbonyl-6-(4-methylnaphthalen-1-yl)-pyridin-2-ylamine, 810 mg (4.554 mmol) N-bromosuccinimide, 35 mL carbon tetrachloride, and 10 mg bis-(1-cyano-1-azo)-cyclohexane. The reaction was heated at reflux for a total of 8 hours as additional portions of initiator were added at 1, 2, and 4 hours. The reaction was cooled, filtered with carbon tetrachloride, and evaporated. The red oil, 2.5 g, was used directly.

$^1$H-NMR (δ, $CDCl_3$): 1.33 (s, 9H), 5.00 (s, 2H), 7.26 (d, J=7.5, 1H), 7.49 (m, 2H), 7.63 (m, 2H), 7.84 (t, J=8, 1H), 8.02 (d, J=8, 1H), 8.115 (bs, 1H), 8.22 (d, J=8, 1H), 8.36 (d, J=7.5, 1H).

$^{13}$C-NMR (δ, $CDCl_3$): 27.6, 31.6, 39.9, 112.6, 121.0, 124.1, 126.6, 126.7, 127.3, 131.5, 131.7, 134.1, 138.8, 139.5, 151.4, 157.1, 177.35.

MS (%): 397/399 (parent+1, 100).

The above oil was taken up in 35 mL dry methylene chloride and treated with 593 mg (3.795 mmol) tetraethylammonium cyanide, and reaction stirred at room temperature for 13 hours. LCMS showed a major peak at P+1=344 and TLC showed a major spot at $R_f$=0.6 in 10% ethyl acetate in methylene chloride. The reaction was evaporated, and the residue chromatographed on silica gel using ethyl acetate in methylene chloride as eluant to afford 1.00 g (77%) of a foam.

$^1$H-NMR (δ, $CDCl_3$): 1.32 (s, 9H), 4.18 (s, 3H), 7.26 (d, J=7.5, 1H), 7.53 (m, 2H), 7.63 (m, 2H), 7.84 (t, J=8, 1H), 7.92 (d, J=8, 1H), 8.04 (d, J=8.5, 1H), 8.10 (bs, 1H), 8.34 (d, J=8, 1H).

$^{13}$C-NMR (δ, $CDCl_3$): 22.0, 27.5, 39.9, 112.6, 121.0, 122.75, 126.0, 126.7, 126.9, 127.2, 131.3, 131.4, 138.9, 139.1, 151.4, 156.9, 177.35.

MS (%): 344 (parent+1, 100).

E. 6-(4-Carboxymethylnaphthalen-1-yl)-pyridin-2-ylamine

To a 100 mL round-bottomed flask equipped with condenser and $N_2$ inlet were added 1.00 g (2.915 mmol) N-t-butylcarbonyl-6-(4-cyanomethylnaphthalen-1-yl)-pyridin-2-ylamine and 35 mL ethanol. The solution was saturated with HCl and refluxed 14 hours, adding two drops of water once it had reached reflux. The reaction (LCMS showed P+1=391) was cooled and evaporated, and the residue taken up in ethyl acetate, washed with aqueous sodium bicarbonate solution, water, and brine, dried over sodium sulfate, and evaporated to an oil, 1.09 g (96%), which was used directly.

$^1$H-NMR (δ, $CDCl_3$): 1.21 (t, J=7, 3H), 1.31 (s, 9H), 4.09 (s, 2H), 4.13 (q, J=7, 2H), 7.25 (d, J=7.5, 1H), 7.4–7.6 (m, 4H), 7.82 (t, J=7.5, 1H), 7.99 (d, J=8, 1H), 8.06 (d, J=8, 1H), 8.13 (bs, 1H), 8.31 (d, J=8, 1H).

$^{13}$C-NMR (δ, $CDCl_3$): 14.2, 27.5, 39.5, 60.4, 61.0, 112.3, 121.1, 124.2, 126.3, 126.4, 126.8, 127.5, 131.4, 131.7, 132.5, 137.8, 138.7, 151.3, 157.5, 171.4, 177.3.

MS (%): 391 (parent+1, 100).

The above oil was taken up in 25 mL 6 N hydrochloric acid, and heated at 95–100° C. for 12 hours. LCMS showed P+1=279. The reaction was cooled, washed with ether, and evaporated, finally dried under vacuum, to a white solid, 0.85 g (93% overall) of the product as the hydrochloride salt.

MS (%): 279 (parent+1, 100).

F. 6-(4-(4-(2-Phenylethyl)piperazinylcarbonyl)-methylnaphthalen-1-yl}-pyridin-2-ylamine To a 100 mL round-bottomed flask equipped with condenser and $N_2$ inlet were added 157 mg (0.50 mmol) 6-(4-carboxymethylnaphthalen-1-yl)-pyridin-2-ylamine, 95 mg (0.50 mmol) N-phenethylpiperazine, 96 mg (0.50 mmol) N-ethyl, N-3-dimethylaminopropyl-carbodiimide, 0.230 mL (1.65 mmol) triethylamine, 10 mg N-hydroxybenzotriazole, and 7 mL dry acetonitrile. The reaction was stirred at room temperature 12 hours (LCMS showed P+1=451 and TLC showed $R_f$=0.3 in 10% methanol/methylene chloride), then evaporated and the residue chromatographed on silica gel using methanol/methylene chloride as eluant to afford the product as a foam, 230 mg (~100%).

$^1$H-NMR ($\delta$, CDCl$_3$): 2.37 (m, 2H), 2.52 (m, 2H), 2.59 (m, 2H), 2.76 (m, 2H), 3.46 (m, 2H), 3.76 (m, 2H), 4.17 (s, 2H), 4.73 (bs, 2H, NH$_2$), 6.46 (d, J=8, 1H), 6.83 (d, J=7.5, 1H), 7.1–7.6 (m, 10H), 7.98 (d, J=8, 1H), 8.14 (d, J=8.5, 1H).

$^{13}$C-NMR ($\delta$, CDCl$_3$): 33.4, 38.5, 41.8, 46.1, 52.8, 53.2, 60.2, 137.2, 115.2, 123.5, 125.6, 126.1, 126.2, 126.3, 126.5, 127.0, 128.5, 128.7, 131.6, 132.2, 138.1, 138.5, 139.9, 157.4, 158.3, 169.7.

MS (%): 451 (parent+1, 100).

G. 6-{4-[2-(4-Phenethyl-piperazin-1-yl)-ethyl]-naphthalen-1-yl}-pyridin-2-ylamine To a 100 mL round-bottomed flask equipped with condenser and $N_2$ inlet were added 200 mg aluminum chloride and 5 mL dry tetrahydrofuran. The solution was cooled to 0° C., and 3.50 mL (3.50 mmol) of a 1.0 M solution of lithium aluminum hydride in tetrahydrofuran was added. Stirring was continued at room temperature for 20 minutes, then the solution was cooled to −70° C., and a solution of 225 mg (0.50 mmol) 6-(4-(4-(2-phenylethyl)piperazinylcarbonyl)-methylnaphthalen-1-yl)-pyridin-2-ylamine in 7 mL dry tetrahydrofuran was added. Stirring was continued 1 hour at −70° C., then 2 hours at room temperature (LCMS showed P+1=437), followed by careful quenching with 5 mL 1 N hydrochloric acid. After stirring for 20 minutes (min.), the reaction was treated with 6 mL 6 N aqueous sodium hydroxide solution, and extracted with several portions of methylene chloride. The organic phase was dried over sodium sulfate and evaporated to afford an oil, which was converted to the hydrochloride salt using HCl in ether, affording the product, 175 mg (64%) as a white solid, mp 80–105° C.

$^1$H-NMR ($\delta$, CDCl$_3$): 2.65 (m, 6H), 2.76 (m, 4H), 2.84 (m, 4H), 3.33 (m, 2H), 4.68 (bs, 2H, NH$_2$), 6.44 (d, J=8, 1H), 6.85 (d, J=7, 1H), 7.1–7.6 (m, 10H), 8.11 (m, 2H).

$^{13}$C-NMR ($\delta$, CDCl$_3$): 30.9, 33.7, 53.3, 59.7, 60.6, 106.9, 115.2, 123.9, 125.77, 125.83, 126.1, 126.7, 126.9, 128.4, 128.7, 131.4, 132.3, 136.9, 137.8, 138.0, 140.4, 157.9, 158.2.

MS (%): 437 (parent+1, 100).

Anal. Calc'd. for $C_{29}H_{32}N_4$.Cl.3/2H$_2$O.1/2(C$_4$H$_{10}$O): C, 69.32, H, 7.69, N, 10.43. Found C, 69.46, H, 7.35, N, 10.36.

EXAMPLE 2

3-{2-[4-(6-Amino-pyridin-2-yl)-naphthalen-1-yl]-ethyl}-3-aza-bicyclo[3.1.0]hex-6-ylamine Prepared as in Example 1, with an extra deblocking step using trifluoroacetic acid in methylene chloride to remove a t-butoxycarbonyl protecting group, in 71% yield, mp 250–260° C., as the hydrochloride salt.

$^1$H-NMR ($\delta$, CDCl$_3$): 1.24 (bs, 2H), 1.36 (bs, 1H), 2.43 (m, 2H), 2.72 (m, 2H), 3.1–3.2 (m, 4H), 4.63 (bs, 2H, NH$_2$), 6.45 (d, J=8, 1H), 6.83 (d, J=7, 1H), 7.3–7.6 (m, 5H), 8.07 (m, 2H).

$^{13}$C-NMR ($\delta$, CDCl$_3$): 25.8, 29.7, 32.7, 55.0, 56.7, 106.8, 115.2, 123.9, 125.7, 125.9, 126.6, 126.8, 131.5, 132.2, 137.1, 137.6, 138.0, 157.9, 158.1.

MS (%): 345 (parent+1, 100).

Anal. Calc'd. for $C_{22}H_{24}N_4$.7/4HCl.(C$_4$H$_{10}$O): C, 64.74, H, 7.47, N, 11.61. Found: C, 64.34, H, 6.94, N, 11.20.

EXAMPLE 3

6-{4-[2-(4-Benzhydryl-piperidin-1-yl)-ethyl]-naphthalen-1-yl}-pyridin-2-ylamine

Prepared as in Example 1, in 74% yield, mp 225–235° C., as the hydrochloride salt.

$^1$H-NMR ($\delta$, CDCl$_3$): 1.32 (m, 1H), 1.64 (m, 1H), 2.07 (m, 2H), 2.17 (m, 1H), 2.70 (m, 2H), 3.06 (m, 2H), 3.31 (m, 2H), 3.55 (d, J=8, 1H), 3.75 (m, 2H), 4.64 (bs, 2H, NH$_2$), 6.45 (d, J=8, 1H), 6.85 (d, J=7, 1H), 7.16 (m, 1H), 7.2–7.6 (m, 14H), 8.10 (m, 2H).

$^{13}$C-NMR ($\delta$, CDCl$_3$): 25.7, 31.0, 31.5, 39.7, 54.0, 59.0, 60.1, 68.0, 106.8, 115.2, 123.9, 125.7, 125.8, 126.1, 126.2, 126.7, 126.9, 128.1, 128.6, 131.6, 132.3, 137.1, 137.7, 138.0, 143.9, 157.9, 158.2.

MS (%): 498 (parent+1, 100).

Anal. Calc'd. for $C_{35}H_{35}N_3$.2HCl: C, 73.67, H, 6.54, N, 7.36. Found: C, 73.86, H, 6.97, N, 7.04.

EXAMPLE 4

6-{4-[2-(6,7-Dimethoxy-3,4-dihydro-1H-isoquinolin-2-yl)-ethyl]-naphthalen-1-yl}-pyridin-2-ylamine Prepared as in Example 1, in 56.5% yield, mp 172–176° C.

$^1$H-NMR ($\delta$, CDCl$_3$): 2.87 (m, 6H), 3.41 (m, 2H), 3.71 (m, 2H), 3.826 (s, 3H), 3.831 (s, 3H), 4.60 (bs, 2H, NH$_2$), 6.47 (d, J=8, 1H), 6.56 (s, 1H), 6.60 (s, 1H), 6.84 (d, J=7.5, 1H), 7.4–7.6 (m, 5H), 8.12 (m, 2H).

$^{13}$C-NMR ($\delta$, CDCl$_3$): 28.7, 31.3, 51.1, 55.7, 55.80, 55.83, 59.3, 106.8, 109.4, 111.3, 115.15, 123.8, 125.67, 125.74, 126.0, 126.5, 126.8, 131.5, 132.2, 136.8, 137.7, 138.0, 147.1, 147.4, 157.8, 158.0.

MS (%): 440 (parent+1, 100).

Anal. Calc'd. for $C_{28}H_{29}N_3O_2$.1/4H$_2$O: C, 75.73, H, 6.70, N, 9.46. Found: C, 75.66, H, 6.54, N, 9.17.

EXAMPLE 5

6-{4-[2-(6-Methoxy-1,3,4,9-tetrahydro-β-carbolin-2-yl)-ethyl]-naphthalen-1-yl}-pyridin-2-ylamine Prepared as in Example 1, in 60% yield, mp 132–138° C.

$^1$H-NMR ($\delta$, CDCl$_3$): 2.81 (m, 2H), 2.91 (m, 4H), 3.31 (m, 2H), 3.51 (bs, 2H), 3.83 (s, 3H), 4.61 (bs, 2H, NH$_2$), 6.46 (d, J=8, 1H), 6.75 (dd, J=2.5, 8.7, 1H), 6.84 (d, J=7, 1H), 6.92 (d, J=2.5, 1H), 7.08 (d, J=8, 1H), 7.36 (d, J=7, 1H), 7.4–7.6 (m, 3H), 8.08 (d, J=8, 1H), 8.13 (dd, J=1,8, 1H), 8.39 (bs, 1H).

$^{13}$C-NMR ($\delta$, CDCl$_3$): 25.5, 50.2, 51.1, 55.8, 58.7, 67.9, 100.2, 103.9, 107.8, 110.7, 111.3, 115.2, 123.8, 125.7, 125.8, 126.1, 126.6, 126.8, 127.5, 131.1, 131.6, 132.1, 132.8, 136.8, 137.6, 138.1, 153.7, 157.7, 158.0.

MS (%): 449 (parent+1, 100).

Anal. Calc'd. for $C_{29}H_{28}N_4O$.(C$_4$H$_{10}$O): C, 75.83, H, 7.33, N, 10.72. Found: C, 75.80, H, 7.00, N, 11.33.

EXAMPLE 6

6-(4-{2-[(Benzo[1,3]dioxol-5-ylmethyl)-amino]-ethyl}-naphthalen-1-yl)-pyridin-2-ylamine Prepared as in Example 1, in 77% yield, mp 80–110° C., as the hydrochloride salt.

$^1$H-NMR (δ, CDCl$_3$): 3.00 (t, J=7, 2H), 3.31 (t, J=7, 2H), 3.70 (s, 2H), 4.62 (bs, 2H, NH$_2$), 5.90 (s, 2H), 6.48 (d, J=8, 1H), 6.72 (s, 1H), 6.73 (m, 1H), 6.81 (m, 1H), 6.85 (d, J=7, 1H), 7.4–7.6 (m, 5H), 8.09 (m, 2H).

$^{13}$C-NMR (δ, CDCl$_3$): 33.7, 49.7, 53.7, 100.9, 106.9, 108.1, 108.7, 115.2, 121.2, 123.9, 125.76, 125.80, 126.1, 126.5, 126.8, 131.7, 132.3, 134.2, 136.5, 137.8, 138.1, 146.5, 147.7, 157.8, 158.1.

MS (%): 398 (parent+1, 100).

Anal. Calc'd. for C$_{25}$H$_{23}$N$_3$O$_2$.2HCl.H$_2$O.1/2(C$_4$H$_{10}$O): C, 61.72, H, 6.14, N, 8.00. Found: C, 61.81, H, 5.97, N, 7.56.

EXAMPLE 7

6-{4-[2-(3,4-Difluoro-benzylamino)-ethyl]-naphthalen-1-yl}-pyridin-2-ylamine

Prepared as in Example 1, in 91% yield, mp 70–80° C., as the hydrochloride salt.

$^1$H-NMR (δ, CDCl$_3$): 2.93 (t, J=7, 2H), 3.315 (t, J=7, 2H), 3.70 (s, 2H), 4.76 (bs, 2H, NH$_2$), 6.47 (d, J=8, 1H), 6.81 (d, J=7, 1H), 7.0–7.2 (m, 3H), 7.4–7.6 (m, 5H), 8.06 (m, 2H).

$^{13}$C-NMR (δ, CDCl$_3$): 32.9, 49.2, 52.2, 107.1, 115.0, 117.1, 123.7, 124.2, 125.9, 126.1, 126.4, 126.7, 131.6, 132.0, 135.8, 137.8, 138.1, 148.1, 148.3, 148.8, 149.0, 150.6, 150.7, 151.3, 151.4, 157.4, 158.1.

MS (%): 390 (parent+1, 100).

Anal. Calc'd. for C$_{24}$H$_{21}$N$_3$F$_2$.3/2HCl.1/2H$_2$O.(C$_4$H$_{10}$O): C, 63.78, H, 6.40, N, 7.97. Found: C, 63.94, H, 5.95, N, 7.89.

EXAMPLE 8

6-{4-[2-(3,4,5-Trimethoxy-benzylamino)-ethyl]-naphthalen-1-yl}-pyridin-2-ylamine Prepared as in Example 1, in 80% yield, mp 75–95° C., as the hydrochloride salt.

$^1$H-NMR (δ, CDCl$_3$): 3.02 (t, J=7, 2H), 3.34 (t, J=7, 2H), 3.73 (s, 2H), 3.78 (s, 6H), 3.795 (s, 3H), 4.655 (bs, 2H, NH$_2$), 6.46 (d, J=8, 1H), 6.49 (s, 2H), 6.82 (d, J=7.5, 1H), 7.4–7.6 (m, 5H), 8.08 (m, 2H).

$^{13}$C-NMR (δ, CDCl$_3$): 33.5, 49.7, 54.0, 55.9, 60.7, 104.7, 106.9, 115.0, 123.8, 125.4, 125.70, 125.74, 126.1, 126.4, 126.7, 131.6, 132.1, 135.8, 136.3, 136.6, 137.8, 138.0, 153.1, 157.6, 158.1.

MS (%): 444 (parent+1, 100).

Anal. Calc'd. for C$_{27}$H$_{29}$N$_3$O$_3$.2HCl.(C$_4$H$_{10}$O): C, 63.05, H, 7.00, N, 7.11. Found: C, 63.04, H, 6.70, N, 6.96.

EXAMPLE 9

6-{4-[2-(3-Chloro-benzylamino)-ethyl]-naphthalen-1-yl}-pyridin-2-ylamine

Prepared as in Example 1, using as a precursor 3,4-dichlorobenzylamine. In this case, the lithium aluminum hydride/aluminum chloride reduction removed one of the chlorine atoms, affording the 3-chlorobenzyl compound. The final product was prepared in 73% yield, mp 60–75° C., as the hydrochloride salt.

$^1$H-NMR (δ CDCl$_3$): 2.99 (t, J=7, 2H), 3.30 (t, J=7, 2H), 3.73 (bs, 2H), 4.675 (bs, 2H, NH$_2$), 6.46 (d, J=8, 1H), 6.83 (d, J=7, 1H), 7.2–7.6 (m, 9H), 8.07 (m, 2H).

$^{13}$C-NMR (δ, CDCl$_3$): 33.6, 49.7, 68.0, 107.0, 115.1, 123.9, 125.8, 126.1, 126.5, 126.8, 128.5, 129.5, 131.7, 132.2, 136.3, 137.8, 138.1, 157.7, 158.2.

MS (%): 388 (parent+1, 100).

Anal. Calc'd. for C$_{24}$H$_{22}$N$_3$Cl.HCl.H$_2$O.1/2(C$_4$H$_{10}$O): C, 65.13, H, 6.31, N, 8.76. Found: C, 64.84, H, 6.25, N, 8.35.

EXAMPLE 10

6-(4-{2-[(Furan-2-ylmethyl)-amino]-ethyl}-naphthalen-1-yl)-pyridin-2-ylamine

Prepared as in Example 1, in 44% yield, mp 185–205° C., as the hydrochloride salt.

$^1$H-NMR (δ, CDCl$_3$): 3.00 (d, J=7, 2H), 3.295 (d, J=7, 2H), 3.79 (s, 2H), 4.68 (bs, 2H, NH$_2$), 6.13 (bs, 1H), 6.26 (bs, 1H), 6.45 (d, J=8, 1H), 6.83 (d, J=7.5, 1H), 7.3–7.6 (m, 6H), 8.08 (m, 2H).

$^{13}$C-NMR (δ, CDCl$_3$): 33.4, 46.1, 49.5, 106.9, 107.0, 110.0, 115.05, 123.8, 125.7, 126.0, 126.4, 126.7, 131.6, 132.1, 136.2, 137.7, 138.0, 141.75, 153.5, 157,6, 158.1.

MS (%): 344 (parent+1, 100).

Anal. Calc'd. for C$_{22}$H$_{21}$N$_3$O.HCl.3/2H$_2$O: C, 64.23, H, 6.25, N, 10.21. Found: C, 64.42, H, 6.04, N, 9.86.

EXAMPLE 11

6-{4-[2-(3,4-Dichloro-benzylamino)-ethyl]-naphthalen-1-yl}-pyridin-2-ylamine

Prepared as in Example 1, using borane methyl sulfide in place of the lithium aluminum hydride/aluminum chloride reduction in the final step. The final product was prepared in 68.5% yield, mp 145–170° C., as the hydrochloride salt.

$^1$H-NMR (δ, CDCl$_3$): 2.98 (t, J=7, 2H), 3.295 (t, J=7, 2H), 3.71 (s, 2H), 4.60 (bs, 2H, NH$_2$), 6.49 (d, J=8, 1H), 6.85 (d, J=7.5, 1H), 7.2–7.6 (m, 7H), 8.08 (m, 2H).

$^{13}$C-NMR (δ, CDCl$_3$): 33.6, 49,7, 52.7, 107.0, 115.3, 123.8, 125.8, 125.9, 126.2, 126.5, 126.9, 127.3, 127.4, 129.9, 130.0, 130.2, 130.7, 131.7, 132.2, 132.3, 136.2, 138.1, 140.7, 157.8, 158.1.

MS (%): 388 (parent+1, 100).

Anal. Calc'd. for C$_{24}$H$_{21}$N$_3$Cl$_2$.HCl.2H$_2$O.1/2(C$_4$H$_{10}$O): C, 58.71, H, 5.87, N, 7.90. Found: C, 58.35, H, 5.92, N, 6.62.

EXAMPLE 12

6-[4-(2-Dimethylamino-ethoxy)-naphthalen-1-yl]-pyridin-2-ylamine

Referring to Scheme 2

A. 4-Bromo-1-benzyloxy-naphthalene:

To a 250 mL round-bottomed flask equipped with addition funnel and N$_2$ inlet were added 2.88 g (20 mmol) 1-naphthol and 50 mL 1,2-dichloroethane, and with stirring a solution of 9.64 g (20 mmol) tetrabutylammonium tribromide in 30 mL 1,2-dichloroethane dropwise over 10 minutes. After stirring an additional 10 minutes at room temperature, the solution was washed with dilute aqueous sodium bisulfite and water, dried over sodium sulfate, and evaporated. The mixture of product and tributylammonium salts was used directly.

$^1$H-NMR (δ, CDCl$_3$): 7.22 (d, J=8, 1H), 7.43 (m, 2H), 7.50 (dt, J=1,8, 1H), 8.05 (d, J=8, 1H), 8.18 (d, J=8, 1H).

$^{13}$C-NMR (δ, CDCl$_3$): 109.8, 111.4, 122.7, 125.3, 126.25, 126.7, 137.4, 129.9, 132.5, 153.0.

The above oil was dissolved in 100 mL acetonitrile, and treated with 3.57 mL (30 mmol) benzyl bromide and 5.53 g (40 mmol) potassium carbonate, the refluxed 14 hours. TLC showed a major spot at $R_f$=0.2 in 5% methylene chloride/hexane. The reaction was cooled, poured into dilute aqueous hydrochloric acid/ethyl acetate, and the organic layer separated, washed with water and brine, dried over sodium sulfate, and evaporated. The residue was chromatographed on silica gel using methylene chloride/hexane as eluant to afford 5.8 g (93%) of an oil.

$^1$H-NMR ($\delta$, CDCl$_3$): 5.22 (s, 2H), 6.74 (d, J=8, 1H), 7.4–7.7 (m, 8H), 8.21 (d, J=8, 1H), 8.39 (d, J=8, 1H).

$^{13}$C-NMR ($\delta$, CDCl$_3$): 70.3, 105.9, 113.6, 122.7, 126.1, 126.9, 127.0, 127.4, 127.9, 128.1, 128.7, 129.5, 132.6, 136.7, 154.3.

MS (%): 314 (parent+1, 100).

B. 1-Benzyloxy-naphthalene-4-boronic acid

Using the procedure in Example 1A, 5.95 g (19 mmol) of 4-bromo-1-benzyloxy-naphthalene was converted to the product in 55% yield as a white solid, mp 149–152° C.

$^1$H-NMR ($\delta$, CDCl$_3$): 5.18 (s, 2H), 6.82 (m, 1H), 7.2–7.8 (m, 8H), 8.28 (m, 2H).

$^{13}$C-NMR ($\delta$, CDCl$_3$): 69.9, 104.5, 104.7, 122.2, 122.4, 124.8, 125.0, 126.5, 126.6, 127.6, 127.7, 127.9, 128.0, 128.5, 130.9, 132.9, 136.9.

C. 2-(2,5-Dimethylpyrrolyl)-6-(4-benzyloxy-1-naphthyl)-pyridine

Prepared as in Example 1B, in ~100% yield as an oil.

$^1$H-NMR ($\delta$, CDCl$_3$): 2.25 (s, 6H), 5.29 (s, 2H), 5.92 (s, 2H), 6.95 (d, J=8, 1H), 7.21 (d, J=7.5, 1H), 7.3–7.6 (m, 9H), 7.89 (t, J=8, 1H), 8.14 (m, 1H), 8.45 (m, 1H).

$^{13}$C-NMR ($\delta$, CDCl$_3$): 13.5, 70.1, 104.8, 106.8, 119.7, 122.5, 123.4, 125.2, 125.3, 125.9, 126.4, 126.9, 127.3, 127.9, 128.2, 128.6, 130.5, 132.0, 136.9, 138.0, 151.8, 155.0, 159.1.

MS (%): 405 (parent+1, 100).

D. 2-(2,5-Dimethylpyrrolyl)-6-(4-hydroxy-1-naphthyl)-pyridine

To a 125 mL round-bottomed flask equipped with condenser and N$_2$ inlet were added 1.53 g (3.795 mmol) 2-(2,5-dimethylpyrrolyl)-6-(4-benzyloxy-1-naphthyl)-pyridine, 1.20 g (18.975 mmol) ammonium formate, 100 mg 10% palladium-on-carbon, and 30 mL ethanol. The reaction was refluxed 4 hours, with additional catalyst and formate added at 2 and 3 hours, then cooled and filtered through Celite with ethanol and methylene chloride. The filtrate was evaporated and the residue taken up in ethyl acetate/aqueous sodium bicarbonate solution. The organic layer was washed with brine, dried over sodium sulfate, and evaporated to a light brown solid, 1.21 g (~100%).

$^1$H-NMR ($\delta$, CDCl$_3$): 2.105 (s, 6H), 5.775 (s, 2H), 6.66 (d, J=8, 1H), 7.04 (d, J=8, 1H), 7.29 (m, 2H), 7.38 (d, J=8, 1H), 7.72 (t, J=8, 1H), 7.95 (m, 1H), 8.18 (m, 1H).

$^{13}$C-NMR ($\delta$, CDCl$_3$): 13.8, 106.7, 106.8, 107.6, 119.6, 122.55, 124.5, 124.7, 125.0, 126.5, 128.4, 128.5, 128.7, 132.0, 138.2, 151.5, 153.9, 159.3.

MS (%): 315 (parent+1, 100).

E. 2-(2,5-Dimethylpyrrolyl)-6-(4-(2-carboethoxymethyloxy)-1-naphthyl)-pyridine

To a 125 mL round-bottomed flask equipped with condenser and N$_2$ inlet were added 1.19 g (3.795 mmol) 2-(2,5-dimethylpyrrolyl)-6-(4-hydroxy-1-naphthyl)-pyridine, 0.505 mL (4.554 mmol) ethyl bromoacetate, 1.05 g (7.59 mmol) potassium carbonate, and 25 mL acetonitrile. The mixture was refluxed 12 hours, cooled (TLC Rf=0.6 in 1/1-ethyl acetate/hexane), poured into water, and extracted into ethyl acetate. The organic layer was washed with brine, dried over sodium sulfate, and evaporated. The residue was chromatographed on silica gel using hexane/ethyl acetate as eluant to afford 2.05 g (~100%) of an oil.

$^1$H-NMR ($\delta$, CDCl$_3$): 1.31 (t, J=7, 3H), 2.26 (s, 6H), 4.29 (q, J=7, 2H), 4.82 (s, 2H), 5.94 (s, 2H), 6.78 (d, J=8, 1H), 7.20 (d, J=8, 1H), 7.5–7.6 (m, 5H), 7.87 (t, J=8, 1H), 8.15 (m, 1H), 8.50 (m, 1H).

$^{13}$C-NMR ($\delta$, CDCl$_3$): 13.6, 14.2, 61.4, 65.7, 104.6, 107.0, 119.9, 122.6, 123.6, 125.3, 125.6, 125.8, 127.2, 128.0, 128.6, 131.4, 132.1, 138.3, 151.8, 154.3, 158.9, 168.6.

MS (%): 401 (parent+1, 100).

F. 2-(2,5-Dimethylpyrrolyl)-6-(4-(2-carboxymethyloxy)-1-naphthyl)-pyridine

To a 125 mL round-bottomed flask equipped with condenser and N$_2$ inlet were added 1.52 g (3.795 mmol) of 2-(2,5-dimethylpyrrolyl)-6-(4-(2-carboethoxymethyloxy)-1-naphthyl)-pyridine, 15 mL tetrahydrofuran, and 478 mg (11.385 mmol) lithium hydroxide hydrate in 15 mL water, with additional methanol to maintain a solution. The reaction was stirred at room temperature for 12 hours, (LCMS P+1=373), poured into dilute aqueous hydrochloric acid, and extracted into ethyl acetate. The organic layer was washed with brine, dried over sodium sulfate, and evaporated to a solid, 1.27 g (90%).

$^1$H-NMR ($\delta$, CDCl$_3$): 2.20 (s, 6H), 4.74 (s, 2H), 5.89 (s, 2H), 6.765 (d, J=8, 1H), 7.20 (d, J=8, 1H), 7.4–7.6 (m, 4H), 7.885 (t, J=8, 1H), 8.04 (m, 1H), 8.44 (m, 1H).

$^{13}$C-NMR ($\delta$ CDCl$_3$): 13.3, 65.3, 104.5, 106.9, 120.3, 122.6, 124.0, 125.0, 125.6, 125.7, 127.2, 128.0, 128.7, 130.8, 132.0, 138.6, 151.7, 154.3, 158.9, 170.9.

MS (%): 373 (parent+1, 100).

G. 2-(2,5-Dimethylpyrrolyl)-6-(4-(2-(dimethylaminocarbonyl)methyloxy)-1-naphthyl)-pyridine Prepared as in Example 1D in ~100% yield as an oil.

$^1$H-NMR ($\delta$, CDCl$_3$): 2.225 (s, 6H), 2.97 (s, 3H), 3.10 (s, 3H), 4.90 (s, 2H), 5.89 (s, 2H), 6.93 (d, J=8, 1H), 7.21 (d, J=8, 1H), 7.4–7.6 (m, 4H), 7.90 (t, J=8, 1H), 8.09 (m, 1H), 8.38 (m, 1H).

$^{13}$C-NMR ($\delta$, CDCl$_3$): 13.5, 35.8, 36.8, 67.9, 104.7, 106.8, 119.9, 122.2, 123.5, 125.4, 125.56, 125.63, 127.1, 128.1, 128.6, 131.2, 132.1, 138.2, 151.8, 154.1, 159.0, 167.7.

MS (%): 400 (parent+1, 100).

H. 2-(2,5-Dimethylpyrrolyl)-6-(4-(2-(2-dimethylaminoethyl)methyloxy)-1-naphthyl)-pyridine Prepared as in Example 1E in ~100% yield as an oil.

$^1$H-NMR ($\delta$, CDCl$_3$): 2.24 (s, 6H), 2.42 (s, 6H), 2.915 (t, J=6, 2H), 4.30 (t, J=6, 2H), 5.91 (s, 2H), 6.90 (d, J=8, 1H), 7.20 (d, J=8, 1H), 7.5–7.7 (m, 4H), 7.89 (t, J=8, 1H), 8.13 (m, 1H), 8.37 (m, 1H).

$^{13}$C-NMR ($\delta$, CDCl$_3$): 13.5, 46.2, 58.2, 67.0, 104.3, 106.8, 119.7, 122.5, 123.5, 125.2, 125.3, 123.8, 126.9, 128.3, 138.6, 130.4, 132.0, 138.1, 151.8, 155.3, 159.1.

MS (%): 386 (parent+1, 100).

I. 6-[4-(2-Dimethylamino-ethoxy)-naphthalen-1-yl]-pyridin-2-ylamine

To a 100 mL round-bottomed flask equipped with condenser and N$_2$ inlet were added 155 mg (0.403 mmol) 2-(2,5-dimethylpyrrolyl)-6-(4-(2-(2-dimethylaminoethyl)methyloxy)-1-naphthyl)-pyridine, 500 mg hydroxylamine hydrochloride, 9 mL ethanol, and 1 mL water. The solution was refluxed 40 h (LCMS P+1=308), cooled, poured into dilute aqueous hydrochloric acid, and washed with ethyl acetate. The aqueous layer was adjusted to pH 12 with 6 N aqueous sodium hydroxide solution and extracted with several portions of methylene chloride. The organic layer was dried over sodium sulfate and evaporated to a solid, 81 mg (65%), mp 98–106° C.

$^1$H-NMR (δ, CDCl$_3$): 2.395 (s, 6H), 2.89 (t, J=6, 2H), 4.27 (t, J=6, 2H), 4.65 (bs, 2H, NH$_2$), 6.43 (d, J=8, 1H), 6.84 (m, 2H), 7.4–7.6 (m, 4H), 8.10 (m, 1H), 8.32 (m, 1H).

$^{13}$C-NMR (δ, CDCl$_3$): 46.2, 58.2, 66.9, 104.2, 106.6, 115.2, 122.2, 125.1, 125.7, 125.8, 126.7, 127.2, 131.4, 132.2, 138.0, 154.7, 157.8, 158.2.

MS (%): 308 (parent+1, 100).

Anal. Calc'd. for C$_{19}$H$_{21}$N$_3$O.1/4H$_2$O: C, 73.17, H, 6.95, N, 13.47. Found: C, 73.18, H, 7.00, N, 13.43.

EXAMPLE 13

6-[4-(2-Pyrrolidin-1-yl-ethoxy)-naphthalen-1-yl]-pyridin-2-ylamine

Prepared as in Example 12, in 69% yield, mp 245–255° C., as the hydrochloride salt.

$^1$H-NMR (δ, CDCl$_3$): 1.79 (bs, 4H), 2.685 (bs, 2H), 3.035 (t, J=6, 2H), 4.30 (t, J=6, 2H), 4.68 (bs, 2H, NH$_2$), 6.41 (d, J=8, 1H), 6.82 (m, 2H), 7.4–7.6 (m, 4H), 8.10 (m, 1H), 8.31 (m, 1H).

$^{13}$C-NMR (δ, CDCl$_3$): 23.6, 54.9, 55.0, 67.8, 104.2, 106.6, 115.1, 122.2, 125.0, 125.7, 125.8, 126.6,. 127.3, 131.4, 132.2, 138.0, 154.7, 157.7, 158.2.

MS (%): 334 (parent+1, 100).

Anal. Calc'd. for C$_{21}$H$_{23}$N$_3$O.2HCl.1/2(C$_4$H$_{10}$O): C, 63.30, H, 6.82, N, 9.48. Found: C, 62.23, H, 6.41, N, 9.56.

EXAMPLE 14

6-(4-{2-[(Benzo[1,3]dioxol-5-ylmethyl)-amino]-ethoxy}-naphthalen-1-yl)-pyridin-2-ylamine Prepared as in Example 12, in 75% yield, mp 60–80° C., as the hydrochloride salt.

$^1$H-NMR (δ, CDCl$_3$): 3.12 (t, J=6, 2H), 3.81 (s, 2H), 4.25 (t, J=6, 2H), 5.91 (s, 2H), 6.41 (d, J=8, 1H), 6.7–6.8 (m, 4H), 6.89 (s, 1H), 7.4–7.5 (m, 4H), 8.10 (m, 1H), 8.28 (m, 1H).

$^{13}$C-NMR (δ, CDCl$_3$): 47.9, 53.5, 67.7, 100.9, 104.4, 106.6, 108.1, 108.7, 115.1, 121.3, 122.0, 125.1, 125.7, 125.8, 126.7, 127.3, 131.5, 132.2, 134,1, 138.0, 146.6, 147.8, 154.6, 157.6, 158.3.

MS (%): 414 (parent+1, 100).

Anal. Calc'd. for C$_{25}$H$_{23}$N$_3$O$_3$.HCl.3/2H$_2$O: C, 62.96, H, 5.71, N, 8.81. Found: C, 63.17, H, 5.63, N, 8.48.

EXAMPLE 15

6-{4-[2-(6,7-Dimethoxy-3,4-dihydro-1H-isoquinolin-2-yl)-ethoxy]-naphthalen-1-yl}-pyridin-2-ylamine Prepared as in Example 12, in 61% yield, mp 130–150° C., as the hydrochloride salt.

$^1$H-NMR (δ, CDCl$_3$): 2.83 (m, 2H), 2.90 (m, 2H), 3.105 (t, J=6, 2H), 3.74 (s, 2H), 3.78 (s, 3H), 3.80 (s, 3H), 4.37 (t, J=6, 2H), 4.69 (bs, 2H, NH$_2$), 6.39 (d, J=8, 1H), 6.49 (s, 1H), 6.57 (s, 1H), 6.84 (m, 2H), 7.4–7.5 (m, 4H), 8.11 (m, 1H), 8.33 (m, 1H).

$^{13}$C-NMR (δ, CDCl$_3$): 28.6, 51.6, 55.9, 56.1, 56.8, 67.0, 104.3, 106.6, 109.5, 111.3, 115.1, 122.2, 125.1, 125.7, 125.8, 125.9, 126.4, 126.7, 127.3, 147.2, 147.5, 154.6, 157.6, 158.2.

MS (%): 456 (parent+1, 100).

Anal. Calc'd. for C$_{28}$H$_{29}$N$_3$O$_3$.2HCl.H$_2$O: C, 61.54, H, 6.09, N, 7.69. Found: C, 61.77, H, 6.04, N, 7.35.

EXAMPLE 16

3-{2-[4-(6-Amino-pyridin-2-yl)-naphthalen-1-yloxy]-ethyl}-3-aza-bicyclo[3.1.0]hex-6-ylamine Prepared as in Example 12, in 63% yield (following a deblocking step with trifluoroacetic acid in methylene chloride to remove a t-butoxycarbonyl protecting group), mp 140–155° C., as the hydrochloride salt.

$^1$H-NMR (δ, CDCl$_3$): 1.35 (bs, 2H), 1.41 (s, 1H), 2.53 (bs, 2H), 2.93 (t, J=6, 2H), 3.11 (m, 4H), 4.185 (t, J=6, 2H), 4.67 (bs, 2H, NH$_2$), 6.42 (d, J=8, 1H), 6.81 (m, 2H), 7.4–7.5 (m, 4H), 8.10 (m, 1H), 8.29 (m, 1H).

$^{13}$C-NMR (δ, CDCl$_3$): 25.8, 32.6, 54.0, 55.6, 67.7, 104.2, 106.6, 115.2, 122.2, 125.1, 125.7, 125.9, 126.6, 127.3, 132.1, 133.7, 138.0, 154.7, 157.7, 158.2.

MS (%): 361 (parent+1, 100).

Anal. Calc'd. for C$_{22}$H$_{24}$N$_4$O.2HCl.1/2(C$_4$H$_{10}$O): C, 61.28, H, 6.64, N, 11.91. Found: C, 61.89, H, 6.44, N, 11.83.

EXAMPLE 17

6-{4-[2-(4-Phenethyl-piperazin-1-yl)-ethoxy]-naphthalen-1-yl}-pyridin-2-ylamine

Prepared as in Example 12, in 78% yield, mp 45–80° C., as the hydrochloride salt.

$^1$H-NMR (δ, CDCl$_3$): 2.5–2.9 (m, 12H), 3.00 (t, J=6, 2H), 4.325 (t, J=6, 2H), 4.62 (bs, 2H), 6.47 (d, J=8, 1H), 6.84 (d, J=8, 1H), 6.85 (d, J=7, 1H), 7.20 (m, 3H), 7.28 (m, 2H), 7.46 (m, 4H), 8.10 (m, 1H), 8.31 (m, 1H).

$^{13}$C-NMR (δ, CDCl$_3$): 33.53, 53.14, 53.64, 57.135, 60.43, 66.61, 104.26, 106.49, 115.165, 122.10, 125.04, 125.43, 125.61, 125.94, 126.57, 127,15, 128.29, 128.61, 131.41, 132.40, 137.92, 140.23, 154.61, 157.67, 158.03.

MS (%): 453 (parent+1, 100).

Anal. Calc'd. for C$_{29}$H$_{32}$N$_4$O.3HCl.3/2H$_2$O.(C$_4$H$_{10}$O): C, 59.77, H, 7.30, N, 8.45. Found: C, 59.42, H, 7.19, N, 8.05.

EXAMPLE 18

6-{4-[2-(3-Amino-pyrrolidin-1-yl)-ethoxy]-naphthalen-1-yl}-pyridin-2-ylamine

Prepared as in Example 12, in 59% yield, mp 70–90° C., as the hydrochloride salt.

$^1$H-NMR (δ, CDCl$_3$): 1.25 (m, 2H), 2.5 (m, 1H), 2.6 (m, 1H), 2.88 (m, 2H), 3.035 (t, J=6, 2H), 4.30 (t, J=6, 2H), 4.59 (bs, 2H), 6.47 (d, J=8, 1H), 6.85 (m, 2H), 7.4–7.6 (m, 4H), 8.09 (m, 1H), 8.31 (m, 1H).

$^{13}$C-NMR (δ, CDCl$_3$): 35.14, 50.90, 53.95, 54.71, 64.63, 67.60, 104.19, 106.45, 115.21, 122.12, 125.00, 125.60, 126.54, 126.72, 127.16, 137.92, 142.45, 147.38, 154.66, 156.33, 157.92.

MS (%): 349 (parent+1, 100).

Anal. Calc'd. for C$_{21}$H$_{24}$N$_4$O.2HCl.2(C$_4$H$_{10}$O).1/3 (CH$_2$Cl$_2$): C, 58.92, H, 7.87, N, 9.37. Found: C, 58.93, H, 7.84, N, 7.77.

EXAMPLE 19

6-[4-(2-Diisopropylamino-ethoxy)-naphthalen-1-yl]-pyridin-2-ylamine

Prepared as in Example 12, in 97.5% yield, as an amorphous solid.

$^1$H-NMR (δ, CDCl$_3$): 1.09 (d, J=6.6, 12H), 3.01 (t, J=7, 2H), 3.11 (m, 2H), 4.12 (t, J=7, 2H), 4.62 (bs, 2H), 6.43 (d, J=8, 1H), 6.86 (m, 2H), 7.47 (m, 4H), 8.14 (m, 1H), 8.35 (m, 1H).

¹³C-NMR (δ, CDCl₃): 20.94, 44.49, 49.61, 69.61, 104.27, 106.50, 115.22, 124.97, 125.70, 125.86, 126.59, 127.34, 131.20, 132.17, 137.98, 154.93, 157,90, 158.14.

MS (%): 364 (parent+1, 100).

HRMS Calc'd. for $C_{23}H_{30}N_3O$: 364.2389. Found: 364.2383.

EXAMPLE 20

6-[4-(2-Morpholin-4-yl-ethoxy)-naphthalen-1-yl]-pyridin-2-ylamine

Prepared as in Example 12, in 60% yield, as an amorphous solid.

¹H-NMR (δ, CDCl₃): 2.66 (m, 4H), 2.96 (t, J=6, 2H), 3.74 (m, 4H), 4.32 (t, J=6, 2H), 4.60 (bs, 2H), 6.48 (d, J=8, 1H), 6.86 (m, 2H), 7.46 (m, 4H), 8.11 (m, 1H), 8.30 (m, 1H).

¹³C-NMR (δ, CDCl₃): 54.10, 57.55, 66.54, 66.94, 104.32, 106.49, 115.19, 122.02, 125.07, 125.61, 125.78, 126.60, 127.13, 131.42, 132.10, 137.97, 154.56, 157.59, 157.93.

MS (%): 350 (parent+1, 100).

Anal. Calc'd. for $C_{21}H_{23}N_3O_2 \cdot 1/4H_2O$: C, 72.18, H, 6.63, N, 12.03. Found: C, 71.62, H, 6.67, N, 11.69.

EXAMPLE 21

6-[4-(2-Piperidin-1-yl-ethoxy)-naphthalen-1-yl]-pyridin-2-ylamine

Prepared as in Example 12, in 68% yield, as an amorphous solid as the hydrochloride salt.

¹H-NMR (δ, CDCl₃): 1.45 (m, 2H), 1.60 (m, 4H), 2.58 (m, 4H), 2.93 (t, J=6, 2H), 4.30 (t, J=6, 2H), 4.66 (bs, 2H), 6.38 (d, J=8, 1H), 6.82 (m, 2H), 7.45 (m, 4H), 8.11 (m, 1H), 8.32 (m, 1H).

¹³C-NMR (δ, CDCl₃): 24.19, 26.07, 55.08, 57.91, 66.66, 104.33, 106.54, 115.09, 122.22, 125.07, 125.75, 125.86, 126.62, 127.18, 131.46, 132.17, 137.94, 154.71, 157.75, 158.24.

MS (%): 348 (parent+1, 100).

Anal. Calc'd. for $C_{22}H_{25}N_3O \cdot 2HCl \cdot 3H_2O \cdot 1/4(C_4H_{10}O)$: C, 56.04, H, 7.26, N, 8.52. Found: C, 56.20, H, 7.11, N, 8.27.

EXAMPLE 22

6-{4-[2-(3,4-Dihydro-1H-isoquinolin-2-yl)-ethoxy]-naphthalen-1-yl}-pyridin-2-ylamine Prepared as in Example 12, in 26% yield, as an amorphous solid as the hydrochloride salt.

¹H-NMR (δ, CDCl₃): 2.96 (m, 4H), 3.16 (t, J=6, 2H), 3.87 (m, 2H), 4.42 (t, J=6, 2H), 4.58 (bs, 2H), 6.48 (d, J=8, 1H), 6.88 (m, 2H), 7.01 (m, 1H), 7.11 (m, 3H), 7.50 (m, 4H), 8.12 (m, 1H), 8.36 (m, 1H).

¹³C-NMR (δ, CDCl₃): 28.96, 51.46, 56.43, 56.79, 66.94, 104.34, 106.45, 115.21, 122.10, 125.04, 125.57, 125.64, 125.84, 126.11, 126.52, 126.57, 127.16, 128.61, 131.46, 132.13, 133.98, 134.48, 137.92, 154.63, 157.73, 157.96.

MS (%): 396 (parent+1, 100).

HRMS Calc'd. for $C_{26}H_{26}N_3O$: 396.2076. Found: 396.2080.

EXAMPLE 23

6-{4-[2-(4-Dimethylamino-piperidin-1-yl)-ethoxy]-naphthalen-1-yl}pyridin-2-ylamine Prepared as in Example 12, in 73% yield, as an amorphous solid as the hydrochloride salt.

¹H-NMR (δ, CDCl₃): 1.56 (m, 2H), 1.80 (m, 2H), 2.18 (m, 3H), 2.26 (s, 6H), 4.28 (t, J=6, 2H), 3.10 (m, 2H), 4.28 (t, J=6, 2H), 4.58 (bs, 2H), 6.43 (d, J=8, 1H), 6.83 (m, 2H), 7.44 (m, 4H), 8.09 (m, 1H), 8.29 (m, 1H).

¹³C-NMR (δ, CDCl₃): 28.33, 29.70, 41.61, 53.65, 57.12, 62.11, 66.77, 76.76, 104.33, 106.51, 115.22, 122.15, 125.09, 125.70, 125.85, 126.64, 127.23, 131.49, 132.15, 137.97, 154.65, 157.80, 158.08.

MS (%): 391 (parent+1, 100).

Anal. Calc'd. for $C_{24}H_{30}N_4O \cdot 3HCl \cdot 3H_2O \cdot 1/2(C_4H_{10}O)$: C, 52.84, H, 7.50, N, 9.48. Found: C, 52.65, H, 7.78, N, 9.38.

HRMS Calc'd. for $C_{24}H_{31}N_4O$: 391.2498. Found: 391.2485.

EXAMPLE 24

6-[4-(1-Benzyl-piperidin-4-yloxy)-naphthalen-1-yl]-pyridin-2-ylamine

A. 4-Bromo-1-fluoronaphthalene

To a 50 mL round-bottomed flask equipped with condenser and N₂ inlet were added 3.75 mL (5.0 g, 34.25 mmol) 1-fluoronaphthalene and 10 mL carbon tetrachloride, followed by dropwise addition of 1.7 mL (5.5 g., 34.375 mmol) bromine over 3 min. The reaction was heated to 50–60° C. as HBr was evolved for 2 hours, then cooled and concentrated. The residue was dissolved in methanol and kept overnight at 0° C. After filtration with cold methanol, the product, with mp close to room temperature, was 4.62 g (60%) of a yellow oil.

¹H-NMR (δ, CDCl₃): 7.02 (t, J=8, 1H), 7.6–7.7 (m, 3H), 8.10 (d, J=8.5, 1H), 8.20 (d, J=8.5, 1H).

GCMS (%): 224/226 (parent, Br⁷⁹/Br⁸¹ 100).

B. 4-Fluoronaphthalene-1-boronic acid

To a 250 mL three-necked round-bottomed flask equipped with septum and N₂ inlet were added 4.62 g (20.53 mmol) 4-bromo-1-fluoronaphthalene and 100 mL dry tetrahydrofuran. The solution was cooled to –70° C., and 15.4 mL (24.64 mmol) of a 1.6 M solution of butyl lithium in hexane was added dropwise over 5 min. The reaction was stirred at –70° C. for 10 min, then 4.2 mL (3.59 g, 24.64 mmol) triethyl borate was added, and the reaction stirred at –70° C. for 20 min and warmed to room temperature. After stirring overnight at room temperature, the reaction was quenched with saturated aqueous ammonium chloride solution, acidified with 1 N hydrochloric acid, and extracted into ethyl acetate (twice). The combined organic layer was washed with brine, dried over sodium sulfate, and evaporated. The residue was triturated with hexane to give an off-white powder, 1.97 g (51%), as a mixture of monoaryl and diaryl boronic acids.

¹H-NMR (δ, CDCl₃): 7.2–7.4 (m, 1H), 7.5–7.7 (m, 3H), 8.0–8.5 (m, 1H), 8.5 and 9.2 (m, 1H). APCI (–) (%): 189 (parent-1, 60).

C. 2-(2,5-Dimethylpyrrolyl)-6-(4-fluoro-naphth-1-yl) pyridine

To a 50 mL round-bottomed flask equipped with condenser and N₂ inlet were added 404 mg (2.13 mmol) 4-fluoronaphthalene-1-boronic acid, 534 mg (2.13 mmol) 2-(2,5-dimethylpyrrolyl)-6-bromopyridine, 902 mg (8.51 mmol) sodium carbonate, 150 mg tetrakistriphenylphosphine, 10 mL ethanol, and 2 mL water. The reaction was refluxed overnight, cooled, poured into water, and extracted into ethyl acetate. After combining with another run on a larger scale, the combined organic layer was washed with brine, dried over sodium sulfate, and evaporated. The residue was chromatographed on silica gel using hexane/ethyl acetate as eluant to afford 4.72 g (85%) of an oil.

¹H-NMR (δ, CDCl₃): 2.25 (s, 6H), 5.92 (s, 2H), 7.1–7.2 (m, 2H), 7.4–7.6 (m, 4H), 7.95 (t, J=8, 1H), 8.12 (d, J=8, 1H), 8.19 (d, J=8, 1H).

¹³C-NMR (δ, CDCl₃): 13.41, 106.97, 108.82, 109.02, 120.18, 120.78, 120.84, 123.42, 123.81, 123.96, 125.48, 126.20, 127.32, 127.68, 127.76, 128.56, 132.35, 133.90, 138.22, 151.87, 157.82, 158.30, 160.34.

MS (%): 317 (parent+1, 100).

HRMS Calc'd. for $C_{21}H_{18}N_2F$ (parent+1): 317.1454. Found: 317.1462.

D. 2-(2,5-Dimethylpyrrolyl)-6-(4-((N-benzyl)-4-piperidinyloxy)-naphth-1-yl)pyridine To a 20 mL round-bottomed flask equipped with condenser and $N_2$ inlet were added 121 mg (0.633 mml) 4-hydroxy-N-benzylpiperidine and 5 mL dry dimethylformamide, followed by 32 mg (0.791 mmol) sodium hydride (60% in oil). The reaction was heated to 70° C. to ensure complete formation of the alkoxide, and then 100 mg (0.316 mmol) 2-(2,5-dimethylpyrrolyl)-6-(4-fluoro-naphth-1-yl)pyridine in 2 mL dry dimethylformamide was added, and the reaction was heated at 80° C. for 10 min. The reaction was cooled, poured into water, and extracted into ethyl acetate. After combining with another run on a larger scale, the combined organic layer was washed with brine, dried over sodium sulfate, and evaporated. The residue was chromatographed on silica gel using methanol/methylene chloride as eluant to afford 489 mg (54%) of an oil.

¹H-NMR (δ, CDCl₃): 2.04 (m, 2H), 2.10 (m, 2H), 2.25 (s, 6H), 2.44 (m, 2H), 2.79 (m, 2H), 3.58 (s, 2H), 4.65 (m, 1H), 5.91 (s, 2H), 6.92 (d, J=8, 1H), 7.2–7.6 (m, 7H), 7.90 (t, J=8, 1H), 8.12 (m, 1H), 8.39 (m, 1H).

¹³C-NMR (δ, CDCl₃): 13.55, 30.69, 50.43, 63.19, 72.54, 105.94, 106.84, 119.72, 122.68, 123.50, 125.22, 126.69, 126.90, 127.08, 128.27, 128.32, 128.67, 129.09, 129.19, 130.12, 132.22, 138.09, 138.40, 151.83, 153.75, 159.16.

MS (%): 488 (parent+1, 100).

HRMS Calc'd. for $C_{33}H_{34}N_3O$ (parent+1): 488.2702. Found: 488.2703.

E. 6-[4-(1-Benzyl-Piperidin-4-yloxy)-naphthalen-1-yl]-pyridin-2-ylamine

Prepared as in Example 12I, in 93% yield, mp 265–285° C. (dec.), as the hydrochloride salt.

¹H-NMR (δ, CDCl₃): 1.9–2.1 (m, 4H), 2.41 (m, 2H), 2.77 (m, 2H), 4.61 (m, 1H), 4.68 (bs, 2H, NH), 6.42 (d, J=8, 1H), 6.86 (m, 2H), 7.2–7.5 (m, 9H), 8.12 (m, 1H), 8,37 (m, 1H).

¹³C-NMR (δ, CDCl₃): 30.65, 50.37, 63.10, 72.53, 106.05, 106.49, 115.08, 122.37, 124.97, 125.67, 126.52, 126.70, 126.97, 127.12, 128.16, 129.11, 131.24, 132.38, 137.89, 138.35, 153.16, 157.66, 158.16.

MS (%): 410 (parent+1, 100).

Anal. Calc'd. for $C_{27}H_{27}N_3O.2HCl.5/3H_2O$: C, 63.28, H, 6.36, N, 8.20. Found: C, 63.18, H, 6.40, N, 7.88.

EXAMPLE 25

6-[4-(1-Benzyl-pyrrolidin-3-yloxy)-naphthalen-1-yl]-pyridin-2-ylamine

Prepared as in Example 24, in 98% yield, mp 160–170° C., as the hydrochloride salt.

¹H-NMR (δ, CDCl₃): 2.15 (m, 1H), 2.36 (m, 1H), 2.67 (m, 1H), 2.79 (m, 1H), 2.87 (m, 1H), 3.12 (m, 1H), 3.69 (AB$_q$, J=13, Dn=20, 2H), 4.74 (bs, 2H), 5.00 (m, 1H), 6.37 (d, J=8, 1H), 6.72 (d, J=8, 1H), 6.83 (d, J=8, 1H), 7.2–7.6 (m, 9H), 8.14 (m, 1H), 8.38 (m, 1H).

¹³C-NMR (δ, CDCl₃): 32.37, 52.84, 60.17, 60.35, 77.0, 105.32, 106.52, 114.95, 122.40, 125.02, 125.70, 126.11, 126.62, 127.03, 127.12, 128.28, 128.82, 131.33, 132.28, 137.88, 138.70, 153.59, 157.59, 158.26.

MS (%): 396 (parent+1, 100).

Anal. Calc'd. for $C_{26}H_{25}N_3O.2HCl.5/3H_2O$: C, 62.65, H, 6.13, N, 8.43. Found: C, 62.73, H, 6.06, N, 8.40.

EXAMPLE 26

6-[4-(4-Dimethylamino-butoxy)-naphthalen-1-yl]-pyridin-2-ylamine

Prepared as in Example 24, in 71% yield, mp 78–90° C., as the hydrochloride salt.

¹H-NMR (δ, CDCl₃): 1.75 (m, 2H), 1.94 (m, 2H), 2.23 (s, 6H), 2.37 (m, 2H), 4.16 (t, J=6, 2H), 4.63 (bs, 2H), 6.43 (d, J=8, 1H), 6.83 (m, 2H), 7.4–7.6 (m, 4H), 8.08 (m, 1H), 8.32 (m, 1H).

¹³C-NMR (δ, CDCl₃): 24.33, 27.12, 45.31, 59.34, 67.90, 104.06, 106.44, 115.11, 122.09, 124.91, 125.57, 125.83, 126.49, 127.17, 131.12, 132.08, 137.88, 154.86, 157.73, 158.06.

MS (%): 336 (parent+1, 100).

Anal. Calc'd. for $C_{21}H_{25}N_3O.2HCl.1/2(H_2CO_3).5/4H_2O$: C, 55.91, H, 6.66, N, 9.10. Found: C, 55.89, H, 6.89, N, 8.80.

EXAMPLE 27

6-[4-(Piperidin-4-yloxy)-naphthalen-1-yl]-Pyridin-2-ylamine

Prepared as in Example 24, in 88% yield, mp 65–75° C. as the free base, and mp 205–220° C., as the hydrochloride salt.

¹H-NMR (δ, CDCl₃): 1.80 (m, 2H), 2.01 (m, 2H), 2.72 (m, 2H), 3.12 (m, 2H), 4.59 (m, 1H), 4.71 (bs, 2H), 6.38 (d, J=8, 1H), 6.82 (m, 2H), 7.4–7.6 (m, 4H), 8.10 (m, 1H), 8.34 (m, 1H).

¹³C-NMR (δ, CDCl₃): 32.01, 43.63, 73.20, 106.09, 106.44, 114.95, 122.30, 124.94, 125.66, 126.49, 126.67, 127.05, 131.32, 132.35, 137.84, 153.03, 157.64, 158.19.

MS (%): 320 (parent+1, 100).

Anal. Calc'd. for $C_{20}H_{21}N_3O.3/4(C_4H_8O_2).1/2H_2O$: C, 70.03, H, 7.15, N, 10.65. Found: C, 70.30, H, 6.77, N, 10.99.

EXAMPLE 28

6-[4-(Pyrrolidin-3-yloxy)-naphthalen-1-yl]-pyridin-2-ylamine

Prepared as in Example 24, in 75% yield, mp 60–70° C. as the free base, and 180–200° C. as the hydrochloride salt.

¹H-NMR (δ, CDCl₃): 2.05 (m, 2H), 2.87 (m, 1H), 3.05 (m, 1H), 3.14 (m, 1H), 3.25 (m, 1H), 4.73 (bs, 2H), 4.94 (m, 1H), 6.37 (d, J=8, 1H), 6.74 (d, J=8, 1H), 6.79 (d, J=7, 1H), 7.42 (m, 4H), 8.10 (m, 1H), 8.24 (m, 1H).

¹³C-NMR (δ, CDCl₃): 33.44, 46.13, 53.62, 76.81, 105.43, 106.47, 114.91, 122.06, 124.98, 125.70, 126.13, 126.54, 127.00, 131.35, 132.23, 137.82, 153.29, 157.56, 158.23.

MS (%): 306 (parent+1, 100).

HRMS Calc'd. for $C_{19}H_{20}N_3O$: 306.1606. Found: 306.1608.

EXAMPLE 29

6-[4-(1-Isobutyl-piperidin-4-yloxy)-naphthalen-1-yl]-pyridin-2-ylamine

Prepared as in Example 24, in 38% yield, mp 198–210° C., as the hydrochloride salt.

¹H-NMR (δ, CDCl₃): 0.92 (d, J=7, 6H), 1.81 (m, 1H), 2.01 (m, 2H), 2.12 (m, 2H), 2.16 (d, J=7, 2H), 2.39 (m, 2H), 2.75 (m, 2H), 4.59 (m, 3H), 6.46 (d, J=8, 1H), 6.87 (m, 2H), 7.4–7.6 (m, 4H), 8.09 (m, 1H), 8.33 (m, 1H).

$^{13}$C-NMR (δ, CDCl$_3$): 20.92, 25.59, 30.46, 50.83, 66.81, 72.56, 106.06, 106.42, 115.16, 122.30, 124.92, 125.63, 126.49, 126.70, 127.07, 131.24, 132.33, 137.89, 153.14, 157.76, 158.00.

MS (%): 376 (parent+1, 100).

Anal. Calc'd. for C$_{24}$H$_{29}$N$_3$O.2HCl.3/2H$_2$O: C, 60.63, H, 7.21, N, 8.84. Found: C, 60.77, H, 7.30, N, 8.48.

EXAMPLE 30

6-[4-(1-Furan-2-ylmethyl-piperidin-4-yloxy)-naphthalen-1-yl]-pyridin-2-ylamine Prepared as in Example 24, in 38% yield, mp 178–195° C., as the hydrochloride salt.

$^1$H-NMR (δ, CDCl$_3$): 2.07 (m, 4H), 2.48 (m, 2H), 2.76 (m, 2H), 3.59 (s, 2H), 4.5 (bs, 2H), 4.62 (m, 1H), 6.21 (m, 1H), 6.31 (m, 1H), 6.45 (d, J=8, 1H), 6.85 (m, 2H), 7.4–7.6 (m, 5H), 8.09 (m, 1H), 8.32 (m, 1H).

$^{13}$C-NMR (δ, CDCl$_3$): 30.42, 49.93, 54.93, 72.00, 106.08, 106.44, 108.69, 109.98, 115.16, 122.30, 124.95, 125.61, 126.49, 126.70, 127.05, 131.29, 132.33, 137.89, 142.07, 151.74, 153.06, 157.73, 158.02.

MS (%): 400 (parent+1, 100).

Anal. Calc'd. for C$_{25}$H$_{25}$N$_3$O$_2$.2HCl.9/4H$_2$O: C, 58.54, H, 6.19, N, 8.19. Found: C, 58.66, H, 6.13, N, 8.04.

EXAMPLE 31

6-[4-(1-Isobutyl-pyrrolidin-3-yloxy)-naphthalen-1-yl]-pyridin-2-ylamine

Prepared as in Example 24, in 45% yield, mp 78–85° C., as the hydrochloride salt.

$^1$H-NMR (δ, CDCl$_3$): 0.94 (d, J=7, 6H), 1.76 (m, 1H), 2.14 (m, 1H), 2.2–2.4 (m, 3H), 2.6–2.9 (m, 3H), 3.10 (m, 1H), 4.59 (bs, 2H), 5.03 (m, 1H), 6.45 (d, J=8, 1H), 6.75 (d, J=8, 1H), 6.85 (d, J=8, 1H), 7.4–7.6 (m, 4H), 8.10 (m, 1H), 8.33 (m, 1H).

$^{13}$C-NMR (δ, CDCl$_3$): 20.35, 21.02, 27.31, 32.20, 53.31, 60.50, 64.82, 105.29, 106.42, 115.15, 122.37, 124.92, 125.56, 126.16, 126.56, 127.05, 131.20, 132.21, 137.88, 153.66, 157.73, 158.03.

MS (%): 362 (parent+1, 100).

HRMS Calc'd. for C$_{23}$H$_{28}$N$_3$O: 362.2232. Found: 362.2217.

EXAMPLE 32

6-[4-(1-Furan-2-ylmethyl-pyrrolidin-3-yloxy)-naphthalen-1-yl]-pyridin-2-ylamine Prepared as in Example 24, in 46% yield, mp 140–160° C., as the hydrochloride salt.

$^1$H-NMR (δ, CDCl$_3$): 2.15 (m, 1H), 2.38 (m, 1H), 2.7–2.9 (m, 3H), 3.21 (m, 1H), 3.72 (AB$_q$, J=7, Dn=20, 2H), 4.60 (bs, 2H), 5.03 (m, 1H), 6.21 (m, 1H), 6.31 (m, 1H), 6.44 (d, J=8, 1H), 6.72 (d, J=8, 1H), 6.84 (d, J=7, 1H), 7.37 (m, 1H), 7.44 (m, 4H), 8.10 M, 1H), 8.32 (m, 1H).

$^{13}$C-NMR (δ, CDCl$_3$): 32.34, 51.72, 52.53, 59.80, 76.70, 105.19, 106.47, 107.98, 110.03, 115.12, 122.37, 124.95, 125.57, 126.06, 126.59, 127.02, 131.30, 132.21, 137.89, 141.98, 152.21, 153.53, 157.67, 158.05.

MS (%): 386 (parent+1, 100).

Anal. Calc'd. for C$_{24}$H$_{23}$N$_3$O$_2$.2HCl.9/4H$_2$O: C, 57.78, H, 5.96, N, 8.42. Found: C, 57.96, H, 5.98, N, 8.14.

EXAMPLE 33

6-[4-(1-Methyl-piperidin-4-yloxy)-naphthalen-1-yl]-pyridin-2-ylamine

Prepared as in Example 24, in 90% yield, mp 179–187° C., as the hydrochloride salt.

$^1$H-NMR (δ, CDCl$_3$): 2.00 (m, 4H), 2.26 (s, 3H), 2.33 (m, 2H), 2.645 (m, 2H), 4.54 (m, 1H), 4.76 (bs, 2H), 6.35 (d, J=8, 1H), 6.78 (d, J=7, 1H), 6.81 (d, J=8, 1H), 7.41 (m, 4H), 8.09 (m, 1H), 8.33 (m, 1H).

$^{13}$C-NMR (δ, CDCl$_3$): 30.46, 46.13, 52.35, 71.64, 105.93, 106.51, 114.88, 122.27, 124.95, 125.66, 126.47, 126.59, 127.07, 131.26, 132.32, 137.84, 153.02, 157.47, 158.26.

MS (%): 334 (parent+1, 100).

Anal. Calc'd. for C$_{21}$H$_{23}$N$_3$O.2HCl.H$_2$O.(C$_4$H$_8$O): C, 60.48, H, 7.11, N, 8.46. Found: C, 60.19, H, 7.61, N, 9.94.

EXAMPLE 34

6-[4-(1-Methyl-pyrrolidin-3-yloxy)-naphthalen-1-yl]-pyridin-2-ylamine

Prepared as in Example 24, in 77% yield, mp 138–145° C., as the hydrochloride salt.

$^1$H-NMR (δ, CDCl$_3$): 2.10 (m, 1H), 2.35 (m, 1H), 2.395 (s, 3H), 2.55 (m, 1H), 2.79 (m, 1H), 2.89 (m, 1H), 2.99 (m, 1H), 4.69 (bs, 2H), 5.01 (m, 1H), 6.41 (d, J=8, 1H), 6.70 (d, J=8, 1H), 6.81 (d, J=8, 1H), 7.43 (m, 4H), 8.07 (m, 1H), 8.32 (m, 1H).

$^{13}$C-NMR (δ, CDCl$_3$): 32.97, 42.10, 55.09, 62.34, 77.39, 105.13, 106.51, 115.04, 122.39, 124.94, 125.54, 126.03, 126.57, 126.99, 131.26, 132.21, 137.88, 153.53, 157.57, 158.15.

MS (%): 320 (parent+1, 100).

Anal. Calc'd. for C$_{20}$H$_{21}$N$_3$O.2HCl.3H$_2$O: C, 53.82, H, 6.55, N, 9.41. Found: C, 54.02, H, 6.45, N, 9.13.

EXAMPLE 35

6-[4-(3-Dimethylamino-propoxy)-naphthalen-1-yl]-pyridin-2-ylamine

Prepared as in Example 24, in 91.5% yield, mp 105–120° C., as the hydrochloride salt.

$^1$H-NMR (δ, CDCl$_3$): 2.08 (m, 2H), 2.26 (s, 6H), 2.54 (t, J=7, 2H), 4.18 (t, J=6, 2H), 4.72 (bs, 2H), 6.40 (d, J=8, 1H), 6.81 (m, 2H), 7.45 (m, 4H), 8.08 (m, 1H), 8.32 (m, 1H).

$^{13}$C-NMR (δ, CDCl$_3$): 27.47, 45.41, 56.52, 66.39, 104.16, 106.47, 115.01, 122.03, 124.91, 125.63, 125.77, 126.47, 127.20, 131.17, 132.08, 137.85, 154.78, 157.63, 158.17.

MS (%): 322 (parent+1, 100).

Anal. Calc'd. for C$_{20}$H$_{23}$N$_3$O.2HCl.7/2H$_2$O: C, 52.52, H, 7.05, N, 9.19. Found: C, 52.62, H, 6.77, N, 8.73.

EXAMPLE 36

6-[4-(1-Aza-bicyclo[2.2.2]oct-3-yloxy)-naphthalen-1-yl]-pyridin-2-ylamine

Prepared as in Example 24, in 89% yield, mp 220–228° C., as the hydrochloride salt.

$^1$H-NMR (δ, CDCl$_3$): 1.41 (m, 1H), 1.54 (m, 1H), 1.71 (m, 1H), 2.09 (m, 1H), 2.27 (m, 1H), 2.78 (m, 3H), 2.96 (m, 2H), 3.30 (m, 1H), 4.56 (m, 1H), 4.71 (bs, 2H), 6.39 (d, J=8, 1H), 6.70 (d, J=8, 1H), 6.81 (d, J=7, 1H), 7.43 (m, 4H), 8.09 (m, 1H), 8.32 (m, 1H).

¹³C-NMR (δ, CDCl₃): 19.61, 24.37, 25.15, 46.53, 47.33, 55.73, 73.44, 105.38, 106.47, 114.95, 122.07, 125.01, 125.73, 126.24, 126.54, 127.05, 131.29, 132.33, 137.84, 153.00, 157.56, 158.20.

MS (%): 346 (parent+1, 100).

Anal. Calc'd. for $C_{22}H_{23}N_3O \cdot 2HCl \cdot 5/2H_2O$: C, 57.02, H, 6.52, N, 9.07. Found: C, 57.07, H, 6.27, N, 8.88.

EXAMPLE 37

6-[4-(2-Dimethylamino-ethoxy)-5,6,7,8-tetrahydro-naphthalen-1-yl]-pyridin-2-ylamine A. 4-Bromo-5,6,7,8-tetrahydro-1-benzyloxynaphthalene To a 250 mL round-bottomed flask equipped with addition funnel and $N_2$ inlet were added 2.96 g (20 mmol) 5,6,7,8-tetrahydro-naphthalen-1-ol and 50 mL 1,2-dichloroethane, and with stirring a solution of 9.64 g (20 mmol) tributylammonium tribromide in 30 mL 1,2-dichloroethane dropwise over 10 min. After stirring an additional 10 min at room temperature, the solution was washed with water, dilute aqueous sodium bisulfite, and water, dried over sodium sulfate, and evaporated. The mixture of product and tributylammonium bromide was used directly.

¹H-NMR (δ, CDCl₃): 1.70 (m, 4H), 2.56 (t, J=6, 2H), 2.61 (t, J=6, 2H), 7.02 (AB, 2H), 8.0 (bs, 1H, OH).

¹³C-NMR (δ, CDCl₃): 22.2, 22.9, 23.8, 30.5, 114.0, 114.7, 126.6, 129.0, 136.7, 154.1.

The above oil was dissolved in 100 mL acetonitrile, and treated with 3.57 mL (30 mmol) benzyl bromide and 5.53 g (40 mmol) potassium carbonate, the refluxed 14 h. TLC showed a major spot at $R_f$=0.3 in 10% methylene chloride/hexane (with benzyl bromide at $R_f$=0.4). The reaction was cooled, poured into dilute aqueous hydrochloric acid/ethyl acetate, and the organic layer separated, washed with water and brine, dried over sodium sulfate, and evaporated. The residue was chromatographed on silica gel using methylene chloride/hexane as eluant to afford 4.0 g (63%) of an oil.

¹H-NMR (δ, CDCl₃): 1.77 (m, 4H), 2.75 (m, 4H), 5.045 (s, 2H), 6.62 (d, J=9, 1H), 7.3–7.5 (m, 6H).

¹³C-NMR (δ, CDCl₃): 22.2, 22.9, 24.0, 30.7, 69.9, 109.8, 116.7, 127.1, 127.9, 128.6, 129.1, 129.3, 137.2, 137.5, 155.6.

B. 5,6,7,8-tetrahydro-1-benzyloxynaphthalene-4-boronic acid

Prepared as in Example 12B as a white solid after trituration with hexane, mp 199–205° C., in 72% yield.

¹H-NMR (δ, CDCl₃): 1.72 (m, 4H), 2.70 (m, 4H), 5.005 (s, 2H), 6.66 (m, 1H), 7.01 (d, J=8, 1H), 7.2–7.4 (m, 5H).

¹³C-NMR (δ, CDCl₃): 22.6, 22.9, 23.4, 30.0, 107.8, 125.9, 127.0, 127.6, 128.4, 131.1, 137.5, 140.8, 156.9.

C. 2-(2,5-Dimethylpyrrolyl)-6-[4-benzyloxy-5,6,7,8-tetrahydro-naphthalen-1-yl]-pyridine Prepared as in Example 12C in 100% yield as an oil.

¹H-NMR (δ, CDCl₃): 1.81 (m, 2H), 1.91 (m, 2H), 2.29 (s, 6H), 2.93 (m, 4H), 5.19 (s, 2h), 6.02 (s, 2H), 6.91 (d, J=8, 1H), 7.21 (d, J=8, 1H), 7.32 (d, J=8, 1H), 7.4–7.6 (m, 6H), 7.89 (t, J=8, 1H).

¹³C-NMR (δ, CDCl₃): 13.5, 22.5, 23.0, 24.0, 28.9, 69.8, 106.8, 108.2, 119.6, 123.1, 126.8, 127.2, 127.8, 12.9, 128.6, 128.7, 132.8, 136.8, 137.6, 138.0, 151.4, 156.8, 160.4.

MS (%): 409 (parent+1, 100).

D. 2-(2,5-Dimethylpyrrolyl)-6-[4-hydroxy-5,6,7,8-tetrahydro-naphthalen-1-yl]-pyridine Prepared as in Example 12D in 100% yield as an low melting solid.

¹H-NMR (δ, CDCl₃): 1.67 (m, 2H), 1.77 (m, 2H), 2.16 (s, 6H), 2.63 (m, 2H), 2.73 (m, 2H), 5.89 (s, 2H), 6.3 (bs, 1H, OH), 6.51 (d, J=8, 1H), 7.02 (d, J=8, 1H), 7.13 (d, J=8, 1H), 7.35 (d, J=8, 1H), 7.83 (t, J=8, 1H).

¹³C-NMR (δ, CDCl₃): 13.3, 22.3, 22.8 23.3, 28.6, 106.6, 112.1, 119.7, 123.3, 124.2, 127.8, 128.7, 131.9, 136.6, 138.1, 151.2, 154.4, 160.5.

MS (%): 319 (parent+1, 100).

E. 2-(2,5-Dimethylpyrrolyl)-6-[4-carboethoxymethoxy-5,6,7,8-tetrahydro-naphthalen-1-yl]-pyridine Prepared as in Example 12E in 83.5% yield as an oil.

¹H-NMR (δ, CDCl₃): 1.31 (t, J=7, 3H), 1.71 (m, 2H), 1.83 (m, 2H), 2.19 (s, 6H), 4.26 (q, J=7, 2H), 4.66 (s, 2H), 5.90 (s, 2H), 6.64 (d, J=8, 1H), 7.12 (d, J=8, 1H), 7.20 (d, J=8, 1H), 7.35 (d, J=8, 1H), 7.82 (t, J=8, 1H).

¹³C-NMR (δ, CDCl₃): 13.4, 14.2, 22.3, 22.9, 23.7, 28.7, 61.2, 65.5, 106.7, 107.8, 119.6, 123.0, 126.9, 127.7, 128.5, 133.4, 137.0, 138.1, 151.3, 156.0, 160.1, 169.0.

MS (%): 405 (parent+1, 100).

F. 2-(2,5-Dimethylpyrrolyl)-6-[4-carboxymethoxy-5,6,7,8-tetrahydro-naphthalen-1-yl]-pyridine Prepared as in Example 12F in 100% yield as a solid, mp 199–206° C.

¹H-NMR (δ, CDCl₃): 1.62 (m, 2H), 1.72 (m, 2H), 2.08 (s, 6H), 2.66 (m, 2H), 2.75 (m, 2H), 4.56 (s, 2H), 5.81 (s, 2H), 6.58 (d, J=8, 1H), 7.09 (m, 2H), 7.31 (d, J=8, 1H), 7.80 (t, J=8, 1H).

¹³C-NMR (δ, CDCl₃): 12.95, 22.1, 22.6, 23.4, 28.4, 65.0, 106.5, 107.7, 119.9, 123.3, 126.7, 127.4, 128.5, 132.8 136.6, 138.3, 151.1, 155.9, 160.1, 171.2.

MS (%): 377 (parent+1, 100).

G. 2-(2,5-Dimethylpyrrolyl)-6-[4-(N,N-dimethylcarboxamido)methoxy-5,6,7,8-tetrahydro-naphthalen-1-yl]-pyridine Prepared as in Example 12G in 100% yield as an oil.

¹H-NMR (δ, CDCl₃): 1.67 (m, 2H), 1.77 (m, 2H), 2.14 (s, 6H), 2.76 (m, 4H), 2.96 (s, 3H), 3.08 (s, 3H), 4.71 (s, 2H), 5.86 (s, 2H), 6.75 (d, J=8, 1H), 7.11 (d, J=8, 1H), 7.16 (d, J=8, 1H), 7.34 (d, J=8, 1H), 7.82 (t, J=8, 1H).

¹³C-NMR (δ, CDCl₃): 13.3, 22.2, 22.8, 23.6, 28.6, 35.7, 36.7, 67.7, 106.5, 107.7, 119.6, 122.9, 126.5, 127.8, 128.6, 133.2, 136.8, 138.0, 151.2, 155.9, 160.2, 168.1.

MS (%): 404 (parent+1, 100).

H. 2-(2,5-Dimethylpyrrolyl)-6-[4-(N,N-dimethylaminoethoxy)-5,6,7,8-tetrahydro-naphthalen-1-yl]-pyridine Prepared as in Example 12H in 93% yield as an oil.

¹H-NMR (δ, CDCl₃): 1.69 (m, 2H), 1.78 (m, 2H), 2.16 (s, 6H), 2.36 (s, 6H), 2.73 (t, J=7, 2H), 2.78 (m, 4H), 4.11 (t, J=7, 2H), 5.88 (s, 2H), 6.74 (d, J=8, 1H), 7.11 (d, J=8, 1H), 7.20 (d, J=8, 1H), 7.36 (d, J=8, 1H), 7.81 (t, J=8, 1H).

¹³C-NMR (δ, CDCl₃): 13.3, 22.3, 22.9, 23.7, 28.7, 46.2, 58.4, 66.6, 106.6, 107.6, 119.5, 122.95, 126.5, 127.7, 128.6, 132.4, 136.6, 137.9, 151.2, 156.9, 160.35.

MS (%): 390 (parent+1, 100).

I. 6-[4-(N,N-Dimethylamino-ethoxy)-5,6,7,8-tetrahydro-naphthalen-1-yl]-pyridin-2-ylamine Prepared as in Example 12I in 57% yield as the hydrochloride salt, mp 239–242° C. from methanol/isopropyl ether.

¹H-NMR (δ, CDCl₃): 1.64 (m, 2H), 1.71 (m, 2H), 2.33 (s, 6H), 2.67 (m, 4H), 2.74 (t, J=6, 2H), 4.07 (t, J=6, 2H), 4.55 (bs, 2H), 6.36 (d, J=8, 1H), 6.62 (d, J=8, 1H), 6.67 (d, J=8, 1H), 7.07 (d, J=8, 1H), 7.40 (t, J=8, 1H).

¹³C-NMR (δ, CDCl₃): 22.3, 22.8 23.6, 28.1, 46.0, 58.2, 66.4, 106.0, 107.4, 114.3, 126.2, 126.8, 133.5, 136.2, 137.6, 156.3, 157.6, 158.8.

MS (%): 312 (parent+1, 100).

Anal. Calc'd. for $C_{19}H_{25}N_3O \cdot 2HCl \cdot 1/4H_2O$: C, 58.69, H, 7.13, N, 10.81. Found: C, 58.72, H, 7.14, N, 10.79.

6-[4-(N,N-Dimethylamino-ethoxy)-5,6,7,8-tetrahydro-naphthalen-1-yl]-pyridin-2-ylamine may also be prepared by the following method:

J. 4-Bromo-1-(N,N-dimethylaminoethoxy)-5,6,7,8-tetrahydro-naphthalene

To a 1 L round-bottomed flask equipped with condenser and N₂ inlet were added 10.0 g (44 mmol) 4-bromo-5,6,7,8-tetrahydro-naphthalen-1-ol (Example 37A), 19 g (130 mmol) 2-dimethylaminoethyl chloride hydrochloride, 30.3 g (220 mmol) powdered potassium carbonate, and 600 mL acetonitrile. The reaction was refluxed 60 hours, followed by an additional portion of the chloride and continued refluxing for 24 hours. The reaction was cooled, filtered and concentrated. The residue was chromatographed on silica gel using methanol/methylene chloride as eluant to afford 8.55 g (65%) of a light brown oil.

¹H-NMR (δ, CDCl₃): 1.72 (m, 4H), 2.33 (s, 6H), 2.63 (m, 2H), 2.68 (m, 2H), 2.73 (t, J=6, 2H), 4.01 (t, J=6, 2H), 6.53 (d, J=8, 1H), 7.28 (d, J=8, 1H).

¹³C-NMR (δ, CDCl₃): 22.1, 22.8, 23.7, 30.5, 46.0, 538.2, 66.6, 109.2, 116.4, 128.8, 129.2, 137.2, 155.6.

MS: 298/300 (parent+1).

K. 1-(N,N-Dimethylaminoethoxy)-5,6,7,8-tetrahydro-naphthalene-4-boronic acid

To a 1 L 3N round-bottomed flask equipped with septum and N₂ inlet were added 8.55 g (28.7 mmol) 4-bromo-1-(2-dimethylaminoethoxy)-5,6,7,8-tetrahydro-naphthalene and 300 mL dry tetrahydrofuran. The solution was cooled to −70° C., and 13.8 mL (34.4 mmol) of a 2.5 M solution of butyl lithium in hexanes was added. The reaction was stirred at −70° C. for 1 h, then 5.9 mL (34.4 mmol) triethyl borate was added, and the reaction stirred at −70° C. for 2 h and warmed to room temperature overnight. The reaction was quenched with aqueous saturated ammonium chloride solution and extracted three times with ethyl acetate. The organic layer was washed with brine, dried over sodium sulfate, and evaporated. The residue was triturated with hexane to a white solid, 6.3 g (83.5%).

¹H-NMR (δ, CDCl₃): 1.79 (m, 4H), 2.44 (s, 6H), 2.68 (m, 2H), 2.89 (m, 2H), 3.32 (m, 2H), 4.19 (m, 2H), 6.74 (d, J=8, 1H), 8.03 (d, J=8, 1H).

L. 2-(2,5-Dimethylpyrrolyl)-6-[4-(N,N-dimethylaminoethoxy)-5,6,7,8-tetrahydro-naphthalen-1-yl]-pyridine To a 500 mL round-bottomed flask equipped with condenser and N₂ inlet were added 6.3 g (23.4 mmol) 1-(N,N-dimethylaminoethoxy)-5,6,7,8-tetrahydro-naphthalene-4-boronic acid, 6.0 g (23.4 mmol) 6-bromo-2-(2,5-dimethylpyrrolyl)pyridine, 10.1 g (95.6 mmol) sodium carbonate, 552 mg tetrakistriphenylphosphine palladium, 200 mL ethanol and 20 mL water. The reaction was refluxed for 20 hours, cooled, and filtered. The filtrate was concentrated, taken up in 1N sodium hydroxide solution, and extracted three times into ethyl acetate. The organic layer was washed with saturated aqueous sodium bicarbonate solution and brine, dried over sodium sulfate, and evaporated. The residue was chromatographed on silica gel using methanol/methylene chloride as eluant to afford 7.67 g (82%) of the product as an oil.

¹H-NMR (δ, CDCl₃): 1.69 (m, 2H), 1.78 (m, 2H), 2.16 (s, 6H), 2.36 (s, 6H), 2.73 (t, J=7, 2H), 2.78 (m, 4H), 4.11 (t, J=7, 2H), 5.88 (s, 2H), 6.74 (d, J=8, 1H), 7.11 (d, J=8, 1H), 7.20 (d, J=8, 1H), 7.36 (d, J=8, 1H), 7.81 (t, J=8, 1H).

¹³C-NMR (δ, CDCl₃): 13.3, 22.3, 22.9, 23.7, 28.7, 46.2, 58.4, 66.6, 106.6, 107.6, 119.5, 122.95, 126.5, 127.7, 128.6, 132.4, 136.6, 137.9, 151.2, 156.9, 160.35.

MS (%): 390 (parent+1, 100).

This material was then converted to 6-[4-(N,N-dimethylamino-ethoxy)-5,6,7,8-tetrahydro-naphthalen-1-yl]-pyridin-2-ylamine by the method given in Example 37I in 83% yield.

EXAMPLE 38

6-[4-(2-Pyrrolidin-1-yl-ethoxy)-5,6,7,8-tetrahydro-naphthalen-1-yl]-pyridin-2-ylamine Prepared as in Example 37, in 58% yield, as a hygroscopic solid as the hydrochloride salt.

¹H-NMR (δ, CDCl₃): 1.64 (m, 2H), 1.74 (m, 2H), 1.77 (m, 4H), 2.62 (m, 4H), 2.68 (m, 4H), 2.89 (t, J=6, 2H), 4.10 (t, J=6, 2H), 4.52 (bs, 2H), 6.37 (d, J=8, 1H), 6.63 (d, J=8, 1H), 6.65 (d, J=8, 1H), 7.07 (d, J=8, 1H), 7.40 (t. J=8, 1H).

¹³C-NMR (δ, CDCl₃): 22.4, 22.9, 23.5, 23.7, 28.2, 54.9, 55.0, 67.4, 106.1, 107.5, 114.4, 126.3, 126.9, 133.5, 136.3, 137.7, 156.4, 157.7, 158.9.

MS (%): 338 (parent+1, 100).

Anal. Calc'd. for $C_{21}H_{27}N_3O \cdot 2HCl \cdot 3H_2O$: C, 54.31, H, 7.60, N, 9.05. Found: C, 54.00, H, 7.83, N, 9.19.

EXAMPLE 39

6-{4-[2-(tert-Butyl-methyl-amino)-ethoxy]-5,6,7,8-tetrahydro-naphthalen-1-yl}-pyridin-2-ylamine Prepared as in Example 37, in 93% yield, mp 65–90° C., as the hydrochloride salt.

¹H-NMR (δ, CDCl₃): 1.08 (s, 9H), 1.64 (m, 2H), 1.74 (m, 2H), 2.325 (s, 3H), 2.68 (m, 4H), 2.79 (t, J=6, 2H), 4.01 (t, J=6, 2H), 4.50 (bs, 2H), 6.37 (d, J=8, 1H), 6.64 (d, J=8, 1H), 6.68 (d, J=8, 1H), 7.08 (d, J=8, 1H), 7.41 (t, J=8, 1H).

¹³C-NMR (δ, CDCl₃): 22.44, 22.89, 23.72, 26.07, 28.24, 36.67, 50.50, 67.89, 106.05, 107.50, 114.52, 126.21, 126.88, 133.32, 136.19, 137.73, 156.56, 157.65, 158.97.

MS (%): 354 (parent+1, 100).

Anal. Calc'd. for $C_{22}H_{31}N_3O \cdot 2HCl \cdot 3H_2O$: C, 55.00, H, 8.18, N, 8.75. Found: C, 55.29, H, 8.25, N, 8.57.

EXAMPLE 40

6-[4-(2-Diisopropylamino-ethoxy)-5,6,7,8-tetrahydro-naphthalen-1-yl]-pyridin-2-ylamine Prepared as in Example 37, in 83% yield, mp 50–60° C., as the hydrochloride salt.

¹H-NMR (δ, CDCl₃): 1.04 (d, J=7, 6H), 1.65 (m, 2H), 1.75 (m, 2H), 2.69 (m, 4H), 2.83 (t, J=7, 2H), 3.05 (septet, J=7, 1H), 3.90 (t, J=7, 2H), 4.55 (bs, 2H), 6.38 (d, J=8, 1H), 6.65 (d, J=8, 1H), 6.70 (d, J=8, 1H), 7.09 (d, J=8, 1H), 7.42 (t, J=8, 1H).

¹³C-NMR (δ, CDCl₃): 20.79, 22.37, 22.81, 23.63, 28.16, 44.51, 49.42, 69.26, 105.99, 107.53, 114.39, 126.14, 126.79, 133.18, 136.12, 137.67, 156.51, 157.60, 158.88.

MS (%): 368 (parent+1, 100).

Anal. Calc'd. for $C_{23}H_{33}N_3O \cdot 2HCl \cdot 5/2H_2O \cdot (C_4H_{10}O)$: C, 57.95, H, 9.01, N, 7.51. Found: C, 57.74, H, 8.62, N, 7.25.

EXAMPLE 41

6-[4-(2-Diethylamino-ethoxy)-5,6,7,8-tetrahydro-naphthalen-1-yl]-pyridin-2-ylamine Prepared as in Example 37, in 42% yield, as a hygroscopic solid as the hydrochloride salt.

$^1$H-NMR (δ, CDCl$_3$): 1.07 (t, J=7, 6H), 1.66 (m, 2H), 1.735 (m, 2H), 2.6–2.8 (m, 8H), 2.91 (t, J=6, 2H), 4.05 (t, J=6, 2H), 4.49 (bs, 2H), 6.39 (d, J=8, 1H), 6.65 (d, J=8, 1H), 6.69 (d, J=8, 1H), 7.09 (d, J=8, 1H), 7.43 (t, J=8, 1H).

$^{13}$C-NMR (δ, CDCl$_3$): 11.92, 22.35, 22.80, 23.60, 25.28, 28.11, 47.78, 51.67, 66.62, 105.96, 107.43, 114.43, 126.20, 126.77, 133.39, 136.20, 137.64, 156.43, 157.54, 158.91.

MS (%): 340 (parent+1, 100).

EXAMPLE 42

6-{4-[2-(3,4-Dihydro-1H-isoquinolin-2-yl)-ethoxy]-5,6,7,8-tetrahydro-naphthalen-1-yl}-pyridin-2-ylamine Prepared as in Example 37, in 67% yield, as an amorphous solid, as the hydrochloride salt.

$^1$H-NMR (δ, CDCl$_3$): 1.67 (m, 2H), 1.79 (m, 2H), 2.73 (m, 4H), 2.94 (m, 4H), 3.03 (t, J=6, 2H), 3.83 (s, 2H), 4.24 (t, J=6, 2H), 4.87 (bs, 2H), 6.37 (d, J=8, 1H), 6.65 (d, J=8, 1H), 6.74 (d, J=8, 1H), 7.0–7.2 (m, 5H), 7.43 (t, J=8, 1H).

$^{13}$C-NMR (δ, CDCl$_3$): 22.39, 22.81, 23.73, 28.17, 28.82, 32.46, 51.37, 56.38, 56.86, 66.47, 106.29, 107.47, 114.25, 125.56, 126.10, 126.14, 126.53, 126.95, 128.61, 133.25, 133.98, 134.47, 136.30, 137.84, 156.31, 157.79, 158.46.

MS (%): 400 (parent+1, 100).

HRMS Calc'd. for C$_{26}$H$_{30}$N$_3$O: 400.2383. Found: 400.2389.

EXAMPLE 43

6-[4-(2-Piperidin-1-yl-ethoxy)-5,6,7,8-tetrahydro-naphthalen-1-yl]-pyridin-2-ylamine Prepared as in Example 37, in 93% yield, as a foam, as the hydrochloride salt.

$^1$H-NMR (δ, CDCl$_3$): 1.42 (m, 2H), 1.58 (m, 6H), 1.74 (m, 2H), 2.51 (m, 4H), 2.67 (m, 4H), 2.79 (t, J=6, 2H), 4.10 (t, J=6, 2H), 4.535 (bs, 2H), 6.34 (d, J=8, 1H), 6.63 (d, J=8, 1H), 6.67 (d, J=8, 1H), 7.08 (d, J=8, 1H), 7.39 (t, J=8, 1H).

$^{13}$C-NMR (δ, CDCl$_3$): 22.43, 22.87, 23.71, 24.18, 26.04, 28.23, 55.04, 58.01, 66.24, 106.05, 107.56, 114.37, 126.26, 126.88, 133.55, 136.26, 137.70, 156.38, 157.72, 158.90.

MS (%): 352 (parent+1, 100).

Anal. Calc'd. for C$_{22}$H$_{23}$N$_3$O.2HCl.2H$_2$O.1/2(C$_4$H$_{10}$O): C, 57.94, H, 8.10, N, 8.45. Found: C, 58.25, H, 7.78, N, 8.69.

EXAMPLE 44

6-[4-(2-Morpholin-4-yl-ethoxy)-5,6,7,8-tetrahydro-naphthalen-1-yl]-pyridin-2-ylamine Prepared as in Example 37, in 67% yield, as a white amorphous solid.

$^1$H-NMR (d, CDCl$_3$): 1.64 (m, 2H), 1.74 (m, 2H), 2.58 (m, 4H), 2.68 (m, 4H), 2.81 (t, J=6, 2H), 3.71 (m, 4H), 4.11 (t, J=6, 2H), 4.45 (bs, 2H), 6.39 (d, J=8, 1H), 6.66 (m, 2H), 7.09 (d, J=8, 1H), 7.43 (t, J=8, 1H).

$^{13}$C-NMR (d, CDCl$_3$): 22.39, 22.85, 23.72, 28.21, 54.16, 57.73, 66.26, 67.03, 106.12, 107.61, 114.53, 126.36, 126.88, 136.39, 137.80, 156.30, 157.57, 158.83.

MS (%): 354 (parent+1, 100).

Anal. Calc'd. for C$_{21}$H$_{27}$N$_3$O$_2$.1/2H$_2$O: C, 69.59, H, 7.79, N, 11.59. Found: C, 69.61, H, 7.51, N, 11.56.

EXAMPLE 45

6-{4-[2-(7,8-Dihydro-5H-[1,3]dioxolo[4,5-g]isoquinolin-6-yl)-ethoxy]-5,6,7,8-tetrahydro-naphthalen-1-yl}-pyridin-2-ylamine Prepared as in Example 37, in 82% yield, as a white, amorphous solid, as the hydrochloride salt.

$^1$H-NMR (d, CDCl$_3$): 1.65 (m, 2H), 1.76 (m, 2H), 2.72 (m, 4H), 2.84 (m, 4H), 2.98 (t, J=6, 2H), 3.69 (s, 2H), 4.20 (t, J=6, 2H), 4.52 (bs, 2H), 5.86 (s, 2H), 6.37 (d, J=8, 1H), 6.47 (s, 1H), 6.55 (s, 1H), 6.65 (d, J=8, 1H), 6.68 (d, J=8, 1H), 7.11 (d, J=8, 1H), 7.42 (t, J=8, 1H).

$^{13}$C-NMR (d, CDCl$_3$): 22.44, 22.89, 23.79, 28.25, 29.09, 51.47, 56.57, 56.87, 66.69, 100.59, 106.11, 106.47, 107.57, 108.43, 114.46, 126.31, 126.92, 127.04, 127.51, 133.65, 136.38, 137.76, 145.67, 146.03, 156.35, 157.68, 158.87.

MS (%): 444 (parent+1, 100).

Anal. Calc'd. for C$_{27}$H$_{29}$N$_3$O$_3$: C, 73.11, H, 6.59, N, 9.47. Found: C, 73.37, H, 7.19, N, 8.96.

HRMS Calc'd. for C$_{27}$H$_{30}$N$_3$O$_3$: 444.2287. Found: 444.2287.

EXAMPLE 46

6-{4-[2-(4-Methyl-piperazin-1-yl)-ethoxy]-5,6,7,8-tetrahydro-naphthalen-1-yl}-pyridin-2-ylamine Prepared as in Example 37, in 100% yield, as an amorphous solid, as the hydrochloride salt.

$^1$H-NMR (d, CDCl$_3$): 1.62 (m, 2H), 1.72 (m, 2H), 2.26 (s, 3H), 2.4–2.8 (m, 12H), 2.81 (t, J=6, 2H), 4.09 (t, J=6, 2H), 4.50 (bs, 2H), 6.35 (d, J=8, 1H), 6.63 (m, 2H), 7.07 (d, J=8, 1H), 7.39 (t, J=8, 1H).

$^{13}$C-NMR (d, CDCl$_3$): 22.4, 22.9, 23.37, 28.2, 46.1, 53.37, 55.2, 57.3, 66.3, 106.1, 107.6, 114.4, 126.3, 126.9, 133.6, 136.3, 137.7, 156.3, 157.7, 158.9.

MS (%): 367 (parent+1, 100).

Anal. Calc'd. for C$_{22}$H$_{30}$N$_4$O.3HCl.H$_2$O.1/2(C$_4$H$_{10}$O): C, 54.29, H, 7.59, N, 10.55. Found: C, 54.20, H, 7.59, N, 10.50.

EXAMPLE 47

6-{4-[2-(4-Dimethylamino-piperidin-1-yl)-ethoxy]-5,6,7,8-tetrahydro-naphthalen-1-yl}-pyridin-2-ylamine Prepared as in Example 37, in 92% yield, as an amorphous solid, as the hydrochloride salt.

$^1$H-NMR (d, CDCl$_3$): 1.54 (m, 2H), 1.64 (m, 2H), 1.77 (m, 4H), 2.12 (m, 3H), 2.26 (s, 6H), 2.66 (m, 4H), 2.80 (t, J=6, 2H), 3.03 (m, 2H), 4.09 (t, J=6, 2H), 4.48 (bs, 2H), 6.37 (d, J=8, 1H), 6.64 (d, J=8, 1H), 6.67 (d, J=8, 1H), 7.07 (d, J=8, 1H), 7.41 (t, J=8, 1H).

$^{13}$C-NMR (d, CDCl$_3$): 22.32, 22.78, 23.61, 28.27, 41.56, 53.55, 57.15, 62.04, 66.31, 105.96, 107.51, 114.36, 126.23, 126.79, 133.52, 136.22, 137.62, 149.63, 156.25, 157.56, 158.85.

MS (%): 395 (parent+1, 100).

HRMS Calc'd. for C$_{24}$H$_{35}$N$_4$O: C 395.2807. Found: 395.2811.

EXAMPLE 48

6-[4-(Piperidin-3-ylmethoxy)-5,6,7,8-tetrahydro-naphthalen-1-yl]-pyridin-2-ylamine A. 2-(2,5-Dimethylpyrrolyl)-6-[4-N-(4-toluenesulfonyl)-(piperidin-3-ylmethoxy)-5,6,7,8-tetrahydro-naphthalen-1-yl]-pyridine To a 125 mL round-bottomed flask equipped with condenser and $N_2$ inlet were added 2.0 g (6.3 mmol) 2-(2,5-dimethylpyrrolyl)-6-(4-hydroxy-5,6,7,8-tetrahydro-naphthalen-1-yl)-pyridine, 4.0 g (9.4 mmol) 3-(hydroxymethyl)-piperidine-di-p-toluenesulfonate, 3.5 g (25.2 mol) potassium carbonate, and 60 mL dry dimethylformamide. The reaction was heated at 140° C. for 14 hours, cooled, and poured into water. The mixture was extracted with ethyl acetate, and the organic layer washed thoroughly with water and brine, dried over sodium sulfate, and evaporated. The residue was chromatographed on silica gel using hexane/ethyl acetate as eluant to afford 3.1 g (86%) of a white solid.

$^1$H-NMR ($\delta$, CDCl$_3$): 1.25 (m, 2H), 1.67 (m, 4H), 1.77 (m, 4H), 2.15 (s, 6H), 2.42 (s, 3H), 2.66 (m, 2H), 2.76 (m, 2H), 3.6–3.9 (m, 5H), 5.87 (s, 2H), 6.66 (d, J=8, 1H), 7.12 (d, J=8, 1H), 7.18 (d, J=8, 1H), 7.3–7.4 (m, 3H), 7.63 (m, 2H), 7.82 (t, J=8, 1H).

$^{13}$C-NMR ($\delta$, CDCl$_3$): 21.43, 22.19, 22.74, 23.53, 23.97, 26.44, 28.53, 35.74, 46.60, 49.30, 69.59, 106.48, 107.31, 119.42, 122.83, 126.39, 127.63, 128.55, 129.51, 132.52, 133.17, 136.62, 137.77, 143.34, 151.14, 156.50, 160.11.

MS (%): 570 (parent+1, 100).

B. 6-[4-N-(4-toluenesulfonyl)-(piperidin-3-ylmethoxy)-5,6,7,8-tetrahydro-naphthalen-1-yl]-pyridin-2-ylamine To a 500 mL round-bottomed flask equipped with condenser and $N_2$ inlet were added 3.1 g (5.4 mmol) 2-(2,5-dimethylpyrrolyl)-6-[4-N-(4-toluenesulfonyl)-(piperidin-3-ylmethoxy)-5,6,7,8-tetrahydro-naphthalen-1-yl]-pyridine, 7.6 g (109 mmol) hydroxylamine hydrochloride, 250 mL ethanol, and 25 mL water. The reaction was refluxed 5 days, cooled, and evaporated. The residue was taken up in ethyl acetate and 1 N hydrochloric acid, and the organic layer washed with additional ethyl acetate and adjusted to pH 12 with 6 N sodium hydroxide solution, then extracted with ethyl acetate. The organic layer was washed with brine, dried over sodium sulfate, and evaporated to afford 2.87 g (100%) of a light brown foam.

$^1$H-NMR ($\delta$, CDCl$_3$): 1.16 (m, 1H), 1.6–1.8 (m, 7H), 2.2–2.4 (m, 3H), 2.41 (s, 3H), 2.7 (m, 4H), 3.7–3.9 (m, 4H), 4.51 (bs, 2H), 6.395 (d, J=8, 1H), 6.61 (d, J=8, 1H), 6.64 (d, J=8, 1H), 7.08 (d, J=8, 1H), 7.29 (m, 2H), 7.42 (t, J=8, 1H), 7.62 (m, 2H).

$^{13}$C-NMR ($\delta$, CDCl$_3$): 21.53, 22.39, 22.85, 23.62, 24.09, 26.52, 28.23, 35.84, 46.70, 49.43, 69.70, 106.19, 107.36, 114.43, 126.35, 126.87, 127.73, 129.61, 133.16, 133.71, 136.44, 137.80, 143.42, 156.18, 157.67, 158.73.

MS (%): 492 (parent+1, 100).

C. 6-[4-(Piperidin-3-ylmethoxy)-5,6,7,8-tetrahydro-naphthalen-1-yl]-pyridin-2-ylamine To a three-necked round-bottomed flask equipped with condenser, septum and $N_2$ inlet were added 4.5 g (33.6 mmol) aluminum chloride and 150 mL dry 1,2-dimethoxyethane. The reaction was cooled to 0° C., and 79 mL (79 mmol) of a 1.0 M solution of lithium aluminum hydride in tetrahydrofuran was added. The reaction was stirred at room temperature for 30 min, then cooled to –70° C., and a solution of 2.77 g (5.6 mmol) 6-[4-N-(4-toluenesulfonyl)-(piperidin-3-ylmethoxy)-5,6,7,8-tetrahydro-naphthalen-1-yl]-pyridin-2-ylamine in 150 mL dry 1,2-dimethoxyethane was added over 10 min. The reaction was stirred and warmed to room temperature, then heated at reflux for 3 days. The reaction was cooled, quenched carefully with 1 N hydrochloric acid, then adjusted to pH 12 with 6 N sodium hydroxide solution. The mixture was extracted with several portions of methylene chloride, and the organic layer washed with aqueous sodium bicarbonate solution and brine, dried over sodium sulfate, and evaporated. The residue was chromatographed using methanol/methylene chloride/triethylamine as eluant to afford 784 mg (41.5%) of an off-white solid, which was converted to the hydrochloride salt.

$^1$H-NMR ($\delta$, CDCl$_3$): 1.21 (m, 1H), 1.46 (m, 1H), 1.6–2.0 (m, 8H), 2.4–2.6 (m, 2H), 2.66 (m, 3H), 3.1 (m, 2H), 3.76 (m, 2H), 4.57 (bs, 2H), 6.35 (d, J=8, 1H), 6.60 (d, J=8, 1H), 6.63 (d, J=8, 1H), 7.39 (t, J=8, 1H).

$^{13}$C-NMR ($\delta$, CDCl$_3$): 22.4, 22.9, 23.6, 25.3, 27.6, 28.2, 36.6, 46.2, 49.3, 70.7, 106.2, 107.3, 114.4, 126.4, 126.8, 133.5, 135.3, 137.8, 156.5, 157.8, 158.7.

MS (%): 338 (parent+1, 100).

Anal. Calc'd. for $C_{21}H_{27}N_3O.1/2H_2O$: C, 72.80, H, 8.15, N, 12.13. Found: C, 73.11, H, 8.29, N, 11.89.

EXAMPLE 49

6-[4-(1-Methyl-piperidin-3-ylmethoxy)-5,6,7,8-tetrahydro-naphthalen-1-yl]-pyridin-2-ylamine Prepared from Example 48 by reductive amination with formaldehyde in formic acid, in 84.5% yield, as a yellow amorphous solid, as the hydrochloride salt.

$^1$H-NMR ($\delta$, CDCl$_3$): 1.12 (m, 2H), 1.6–2.0 (m, 8H), 2.18 (m, 1H), 2.29 (s, 3H), 2.69 (m, 4H), 2.79 (m, 1H), 3.00 (m, 1H), 3.81 (m, 2H), 4.44 (bs, 2H), 6.40 (d, J=8, 1H), 6.65 (m, 2H), 7.08 (d, J=8, 1H), 7.43 (t, J=8, 1H).

$^{13}$C-NMR ($\delta$, CDCl$_3$): 22.32, 22.80, 23.54, 24.83, 26.71, 28.16, 36.45, 46.60, 56.13, 59.30, 70.68, 105.98, 107.24, 114.49, 126.26, 126.74, 127.83, 133.29, 136.16, 137.68, 156.44, 157.49, 158.89.

MS (%): 352 (parent+1, 100).

HRMS Calc'd. for $C_{22}H_{30}N_3O$: 352.2389. Found: 352.2365.

EXAMPLE 50

6-[4-(1-Isobutyl-piperidin-3-ylmethoxy)-5,6,7,8-tetrahydro-naphthalen-1-yl]-pyridin-2-ylamine Prepared from Example 48 by reductive amination with isobutyraldehyde, in 5.7% yield, as a light tan amorphous solid, as the hydrochloride salt.

$^1$H-NMR ($\delta$, CDCl$_3$): 0.90 (d, J=6, 6H), 1.19 (m, 1H), 1.6–2.0 (m, 10H), 2.15 (m, 3H), 2.68 (m, 4H), 2.83 (m, 1H), 2.98 (m, 1H), 3.83 (m, 2H), 4.54 (bs, 2H), 6.41 (d, J=8, 1H), 6.65 (m, 2H), 7.08 (d, J=8, 1H), 7.435 (t, J=8, 1H).

$^{13}$C-NMR ($\delta$, CDCl$_3$): 20.99, 21.06, 22.42, 22.87, 23.61, 24.44, 25.36, 27.34, 28.22, 35.98, 54.48, 57.44, 67.05, 70.71, 106.19, 107.36, 114.54, 126.33, 126.86, 133.14, 136.24, 137.86, 156.58, 157.59, 158.82.

MS (%): 394 (parent+1, 100).

HRMS Calc'd. for $C_{25}H_{36}N_3O$: C 394.2858. Found: 394.2893.

EXAMPLE 51

6-{4-[2-(7,8-Dihydro-5H-[1,3]dioxolo[4,5-g]
isoquinolin-6-yl)-ethoxy]-naphthalen-1-yl}-pyridin-
2-ylamine Prepared as in Example 12, in 65% yield, as an amorphous solid.

$^1$H-NMR (d, CDCl$_3$): 2.85 (m, 2H), 2.93 (m, 2H), 3.15 (t, J=6, 2H), 3.77 (s, 2H), 4.415 (t, J=6, 2H), 4.56 (bs, 2H), 5.87 (s, 2H), 6.48 (s, 1H), 6.51 (d, J=8, 1H), 6.56 (s, 1H), 6.88 (m, 2H), 7.4–7.6 (m, 4H), 8.10 (m, 1H), 8.31 (m, 1H).

$^{13}$C-NMR (d, CDCl$_3$): 28.9, 51.4, 566.4, 56.6, 66.8, 100.5, 104.3, 106.4, 106.5, 108.3, 115.3, 122.1, 125.1, 125.6, 125.8, 126.6, 126.8, 127.2, 131.3, 132.1, 138.0, 145.7, 146.0, 154.6, 157.6, 157.8.

MS (%): 440 (parent+1, 100).

HRMS Calc'd. for $C_{27}H_{26}N_3O_3$: 440.1974. Found: 440.1971.

EXAMPLE 52

6-[7-(2-Dimethylamino-ethoxy)-indan-4-yl]-pyridin-
2-ylamine

Prepared as in Example 37, starting with 1-indanol, in 57% yield, mp 215–218° C., as the hydrochloride salt.

$^1$H-NMR (d, CDCl$_3$): 2.00 (quin, J=6, 2H), 2.32 (s, 6H), 2.72 (t, J=6, 2H), 2.86 (t, J=7, 2H), 3.06 (t, J=7, 2H), 4.10 (t, J=6, 2H), 4.63 (bs, 2H), 6.32 (d, J=8, 1H), 6.71 (d, J=8, 1H), 6.76 (d, J=8, 1H), 7.39 (m, 2H).

$^{13}$C-NMR (d, CDCl$_3$): 25.31, 29.56, 33.78, 46.07, 58.24, 66.46, 106.02, 109.34, 112.88, 127.97, 129.99, 132.66, 137.80, 144.30, 155.24, 157.34, 158.08.

MS (%): 298 (parent+1, 100).

Anal. Calc'd. for $C_{18}H_{23}N_3O·2HCl·1/2H_2O$: C, 56.99, H, 6.91, N, 11.08. Found: C, 56.59, H, 6.93, N, 11.01.

EXAMPLE 53

6-[7-(2-Diisopropylamino-ethoxy)-indan-4-yl]-
pyridin-2-ylamine

Prepared as in Example 37, in 63% yield, as a tan amorphous solid, as the hydrochloride salt.

$^1$H-NMR (d, CDCl$_3$): 1.06 (d, J=6, 12H), 2.02 (quin, J=7, 2H), 2.875 (m, 4H), 3.10 (m, 4H), 3.98 (m, 2H), 4.52 (bs, 2H), 6.35 (d, J=8, 1H), 6.74 (d, J=8, 1H), 6.80 (d, J=8, 1H), 7.41 (m, 2H).

$^{13}$C-NMR (d, CDCl$_3$): 20.71, 25.33, 29.56, 33.81, 44.65, 49.86, 68.95, 105.94, 109.31, 112.99, 127.99, 129.76, 132.48, 137.83, 144.27, 155.39, 157.45, 157.94.

MS (%): 354 (parent+1, 100).

Anal. Calc'd. for $C_{22}H_{31}N_3O·2HCl·H_2O·1/2(C_4H_{10}O)$: C, 59.87, H, 8.37, N, 8.73. Found: C, 59.69, H, 8.19, N, 8.75.

EXAMPLE 54

6-[7-(2-Morpholin-4-yl-ethoxy)-indan-4-yl]-pyridin-
2-ylamine

Prepared as in Example 37, in 93% yield, as a tan amorphous solid.

$^1$H-NMR (d, CDCl$_3$): 2.01 (quin, J=7, 2H), 2.58 (m, 4H), 2.79 (t, J=6, 2H), 2.86 (t, J=7, 2H), 3.09 (t, J=7, 2H), 3.71 (m, 4H), 4.14 (t, J=6, 2H), 4.57 (bs, 2H), 6.33 (d, J=8, 1H), 6.72 (d, J=8, 1H), 6.79 (d, J=8, 1H), 7.40 (m, 2H).

$^{13}$C-NMR (d, CDCl$_3$): 25.20, 29.50, 33.73, 54.10, 57.56, 66.18, 66.92, 105.89, 109.33, 112.81, 127.91, 130.07, 132.59, 137.71, 144.29, 155.04, 157.26, 157.95.

MS (%): 340 (parent+1, 100).

Anal. Calc'd. for $C_{20}H_{25}N_3O_2$: C, 70.77, H, 7.42, N, 12.38. Found: C, 70.49, H, 7.58, N, 12.02.

EXAMPLE 55

6-{7-[2-(7,8-Dihydro-5H-[1,3]dioxolo[4,5-g]
isoquinolin-6-yl)-ethoxy]-indan-4-yl}-pyridin-2-
ylamine Prepared as in Example 37, in 81% yield, as a foam.

$^1$H-NMR (d, CDCl$_3$): 2.04 (quin, J=7, 2H), 2.8–3.0 (m, 8H), 3.11 (t, J=7, 2H), 3.70 (s, 2H), 4.24 (t, J=6, 2H), 4.63 (bs, 2H), 5.86 (s, 2H), 6.35 (d, J=8, 1H), 6.48 (s, 1H), 6.55 (s, 1H), 6.76 (d, J=8, 1H), 6.81 (d, J=8, 1H), 7.4–7.5 (m, 2H).

$^{13}$C-NMR (d, CDCl$_3$): 25.25, 28.83, 29.56, 33.75, 51.24, 56.29, 56.46, 66.49, 100.52, 105.99, 106.39, 108.34, 109.30, 112.86, 126.89, 127.28, 127.98, 129.88, 132.59, 137.82, 144.32, 145.63, 145.99, 155.12, 157.13, 157.87.

MS (%): 430 (parent+1, 100).

HRMS Calc'd. for $C_{26}H_{28}N_3O_3$: 430.2160. Found: 430.2131.

EXAMPLE 56

6-{7-[2-(4-Methyl-piperazin-1-yl)-ethoxy]-indan-4-
yl}-pyridin-2-ylamine

Prepared as in Example 37, in 81% yield, as a tan solid, mp>205° C., as the hydrochloride salt.

$^1$H-NMR (d, CDCl$_3$): 2.00 (quin, J=7, 2H), 2.26 (s, 3H), 2.4–2.7 (m, 8H), 2.8–2.9 (m, 4H), 3.08 (t, J=7, 2H), 4.13 (t, J=6, 2H), 4.49 (bs, 2H), 6.34 (d, J=8, 1H), 6.71 (d, J=8, 1H), 6.79 (d, J=8, 1H), 7.40 (t, J=8, 1H).

$^{13}$C-NMR (d, CDCl$_3$): 25.20, 29.46, 33.72, 45.96, 53.55, 55.04, 57.08, 66.24, 105.85, 109.32, 112.86, 127.86, 129.97, 132.61, 137.69, 144.23, 155.08, 157.31, 157.87.

MS (%): 353 (parent+1, 100).

HRMS Calc'd. for $C_{21}H_{29}N_4O$: 353.2345. Found: 353.2341.

EXAMPLE 57

6-{7-[2-(tert-Butyl-methyl-amino)-ethoxy]-indan-4-
yl}-pyridin-2-ylamine

Prepared as in Example 37, in 96% yield, mp foams at 110° C., as the hydrochloride salt.

$^1$H-NMR (d, CDCl$_3$): 1.10 (s, 9H), 2.005 (quin, J=7, 2H), 2.34 (s, 3H), 2.81 (t, J=7, 2H), 2.87 (t, J=7, 2H), 3.07 (t, J=7, 2H), 4.09 (t, J=7, 2H), 4.79 (bs, 2H), 6.34 (d, J=8, 1H), 6.75 (m, 2H), 7.40 (m, 2H).

$^{13}$C-NMR (d, CDCl$_3$): 14.11, 25.26, 25.89, 29.47, 32.51, 33.65, 36.50, 50.31, 67.47, 106.04, 109.13, 112.84, 128.01, 129.50, 132.33, 137.81, 144.07, 155.34, 156.10, 157.24, 158.05.

MS (%): 340 (parent+1, 100).

HRMS Calc'd. for $C_{21}H_{30}N_3O$: 340.2381. Found: 340.2389.

EXAMPLE 58

6-{7-[2-(4-Dimethylamino-piperidin-1-yl)-ethoxy]-indan-4-yl}-pyridin-2-ylamine

Prepared as in Example 37, in 100% yield, as an amorphous solid, as the hydrochloride salt.

$^1$H-NMR (d, CDCl$_3$): 1.60 (m, 2H), 1.82 (m, 3H), 2.00 (quin, J=7, 2H), 2.13 (m, 2H), 2.27 (s, 6H), 2.80 (t, J=6, 2H), 2.85 (t, J=7, 2H), 3.06 (t, J=7, 2H), 4.15 (t, J=6, 2H), 4.75 (bs, 2H), 6.35 (d, J=8, 1H), 6.72 (d, J=8, 1H), 6.76 (d, J=8, 1H), 7.405 (m, 2H).

$^{13}$C-NMR (d, CDCl$_3$): 25.22, 27.83, 29.47, 32.47, 33.63, 41.37, 53.51, 56.96, 61.98, 66.14, 106.04, 109.30, 112.86, 127.99, 129.77, 132.49, 137.81, 144.16, 155.09, 155.91, 157.20, 158.00.

MS (%): 381 (parent+1, 100).

HRMS Calc'd. for C$_{23}$H$_{33}$N$_4$O: 381.2669. Found: 381.2654.

EXAMPLE 59

6-[7-(2-Pyrrolidin-1-yl-ethoxy)-indan-4-yl]-pyridin-2-ylamine

Prepared as in Example 37, in 72% yield, mp 113–117° C., as the hydrochloride salt.

$^1$H-NMR (d, CDCl$_3$): 1.77 (m, 4H), 2.01 (uqin, J=7, 2H), 2.62 (m, 4H), 2.89 (m, 4H), 3.08 (t, J=7, 2H), 4.15 (t, J=6, 2H), 4.52 (bs, 2H), 6.34 (d, J=8, 1H), 6.73 (d, J=8, 1H), 6.79 (d, J=8, 1H), 7.40 (m, 4H).

$^{13}$C-NMR (d, CDCl$_3$): 23.53, 25.30, 29.57, 33.78, 54.88, 54.98, 67.37, 105.94, 109.36, 112.99, 127.97, 129.94, 132.65, 137.80, 144.28, 155.27, 157.45, 157.95.

MS (%): 324 (parent+1, 100).

Anal. Calc'd. for C$_{20}$H$_{25}$N$_3$O.2HCl.3/2H$_2$O: C, 56.74, H, 7.14, N, 9.92. Found: C, 56.40, H, 7.07, N, 9.84.

EXAMPLE 60

6-[7-[2-(N-Benzyl,N-methyl-amino)-ethoxy)]-indan-4-yl]-pyridin-2-ylamine

Prepared as in Example 37, in 48% yield, mp 110–130° C., as the hydrochloride salt.

$^1$H-NMR (d, CDCl$_3$): 2.045 (quin, J=7, 2H), 2.37 (s, 3H), 2.87 (t, J=6, 2H), 2.92 (t, J=7, 2H), 3.13 (t, J=7, 2H), 3.65 (s, 2H), 4.16 (t, J=6, 2H), 4.65 (bs, 2H), 6.34 (d, J=8, 1H), 6.74 (d, J=8, 1H), 6.82 (d, J=8, 1H), 7.2–7.6 (m, 7H).

$^{13}$C-NMR (d, CDCl$_3$): 25.37, 29.67, 33.86, 43.04, 55.84, 62.74, 66.54, 106.04, 109.25, 112.94, 127.07, 128.04, 128.32, 129.06, 129.98, 132.62, 137.84, 139.06, 144.34, 155.34, 157.42, 158.13.

MS (%): 374 (parent+1, 100).

Anal. Calc'd. for C$_{24}$H$_{27}$N$_3$O.2HCl: C, 64.57, H, 6.55, N, 9.41. Found: C, 64.52, H, 6.88, N, 9.38.

EXAMPLE 61

6-[7-[(4-Phenethylpiperazin-1-yl)-ethoxy]-indan-4-yl]-pyridin-2-ylamine

Prepared as in Example 37, in 41% yield, mp 105–130° C., as the hydrochloride salt.

$^1$H-NMR (d, CDCl$_3$): 1.995 (quin, J=7, 2H), 2.5–2.9 (m, 16H), 3.08 (t, J=7, 2H), 4.13 (t, J=6, 2H), 4.61 (bs, 2H), 6.30 (d, J=8, 1H), 6.70 (d, J=8, 1H), 6.76 (d, J=8, 1H), 7.2–7.5 (m, 7H).

$^{13}$C-NMR (d, CDCl$_3$): 25.31, 29.57, 33.60, 33.82, 53.20, 53.69, 57.22, 60.55, 66.27,7 105.95, 109.35, 112.82, 126.02, 128.00, 128.37, 128.66, 128.69, 130.07, 132.62, 137.76, 140.29, 144.30, 155.17, 157.34, 158.10.

MS (%): 443 (parent+1, 100).

Anal. Calc'd. for C$_{28}$H$_{34}$N$_4$O.2HCl: C, 65.24, H, 7.04, N, 10.87. Found: C, 65.03, H, 7.23, N, 10.81.

EXAMPLE 62

6-[7-[(4-Isobutylpiperazin-1-yl)-ethoxy]-indan-4-yl]-pyridin-2-ylamine

Prepared as in Example 37, in 92% yield, mp 170–190° C., as the hydrochloride salt.

$^1$H-NMR (d, CDCl$_3$): 0.85 (d, J=6, 6H), 1.73 (m, 1H), 2.0 (m, 2H), 2.04 (d, J=7, 2H), 2.40 (m, 4H), 2.60 (m, 4H), 2.79 (t, J=7, 2H), 2.84 (t, J=7, 2H), 3.07 (t, J=7, 2H), 4.13 (t, J=6, 2H), 4.57 (bs, 2H), 6.32 (d, J=8, 1H), 6.70 (d, J=8, 1H), 6.76 (d, J=8, 1H), 7.38 (m, 2H).

$^{13}$C-NMR (d, CDCl$_3$): 25.16, 25.28, 29.45, 33.69, 53.47, 53.70, 57.16, 66.22, 66.84, 105.82, 109.32, 112.79, 127.88, 129.96, 132.56, 137.65, 144.20, 155.12, 157.33, 157.92.

MS (%): 395 (parent+1, 100).

Anal. Calc'd. for C$_{24}$H$_{34}$N$_4$O.3HCl.H$_2$O: C, 55.23, H, 7.53, N, 10.73. Found: C, 55.51, H, 7.72, N, 10.46.

EXAMPLE 63

6-[4-(2-Amino-cyclohexyloxy)-naphthalen-1-yl]-pyridin-2-ylamine

Prepared as in Example 24, in 96% yield, mp 218–230° C., as the hydrochloride salt.

$^1$H-NMR (d, CDCl$_3$): 1.36 (m, 4H), 1.76 (m, 2H), 2.0–2.4 (m, 2H), 3.05 (m, 1H), 4.10 (m, 1H), 4.62 (bs, 2H), 6.45 (d, J=8, 1H), 6.84 (d, J=8, 1H), 6.93 (d, J=8, 1H), 7.4–7.6 (m, 4H), 8.08 (m, 1H), 8.32 (m, 1H).

$^{13}$C-NMR(d, CDCl$_3$): 24.30, 24.49, 29.60, 33.36, 54.87, 83.58, 106.14, 106.51, 115.12, 122.07, 125.00, 125.71, 126.50, 126.57, 127.12, 131.32, 132.28, 137.94, 153.86, 157.64, 158.05.

MS (%): 334 (parent+1, 100).

Anal. Calc'd. for C$_{21}$H$_{23}$N$_3$O.2HCl.1/4H$_2$O.1/2(C$_4$H$_8$O): C, 60.73, H, 6.54, N, 9.24. Found: C, 60.63, H, 6.58, N, 9.10.

EXAMPLE 64

6-[4-(Piperidin-3-ylmethoxy)-naphthalen-1-yl]-pyridin-2-ylamine

Prepared as in Example 24, in 38% yield, mp 164–185° C., as the hydrochloride salt.

$^1$H-NMR (d, CDCl$_3$): 1.2–1.4 (m, 1H), 1.54 (m, 1H), 1.69 (m, 1H), 1.91 (m, 1H), 2.07 (m, 1H), 2.45 (m, 1H), 2.55 (m, 1H), 2.8–3.0 (m, 1H), 3.04 (m, 1H), 3.25 (m, 1H), 3.92 (m, 2H), 4.71 (bs, 2H), 6.43 (d, J=8, 1H), 6.78 (d, J=8, 1H), 6.82 (d, J=8, 1H), 7.4–7.6 (m, 4H), 8.08 (m, 1H), 8.29 (m, 1H).

$^{13}$C-NMR (d, CDCl$_3$): 25.72, 27.81, 36.93, 46.67, 49.84, 71.04, 103.97, 106.55, 115.05, 122.04, 125.02, 125.60, 125.73, 126.60, 127.17, 131.17, 132.05, 137.95, 154.79, 157.60, 158.13.

MS (%): 334 (parent+1, 100).

Anal. Calc'd. for C$_{21}$H$_{23}$N$_3$O.2HCl.1/2H$_2$O.1/4(C$_4$H$_8$O): C, 60.41, H, 6.45, N, 9.61. Found: C, 60.33, H, 6.50, N, 9.28.

EXAMPLE 65

6-[4-(1-Isobutyl-azetidin-3-yloxy)-naphthalen-1-yl]-pyridin-2-ylamine

Prepared as in Example 24, in 57% yield, mp 133–148° C., as the hydrochloride salt.

$^1$H-NMR (d, CDCl$_3$): 0.91 (d, J=6, 6H), 1.65 (septet, J=6, 1H), 2.37 (d, J=7, 2H), 3.18 (m, 2H), 3.98 (m, 2H), 4.56 (bs, 2H), 5.01 (m, 1H), 6.47 (d, J=8, 1H), 6.59 (d, J=8, 1H), 6.84 (d, J=8, 1H), 7.3–7.5 (m, 4H), 8.09 (m, 1H), 8.30 (m, 1H).

$^{13}$C-NMR (d, CDCl$_3$): 20.89, 27.19, 62.17, 67.03, 68.54, 104.60, 106.61, 115.26, 122.16, 125.20, 125.66, 125.73, 126.78, 127.05, 131.87, 132.25, 138.04, 152.89, 157.70, 158.04.

MS (%): 348 (parent+1, 100).

Anal. Calc'd. for C$_{22}$H$_{25}$N$_3$O.2HCl.1/2H$_2$O.(C$_4$H$_8$O): C, 60.35, H, 7.01, N, 8.12. Found: C, 60.50, H, 7.05, N, 8.00.

EXAMPLE 66

6-[4-(8-Methyl-8-aza-bicyclo[3.2.1]oct-3-yloxy)-naphthalen-1-yl]-pyridin-2-ylamine Prepared as in Example 24, in 93% yield, mp 260–275° C., as the hydrochloride salt.

$^1$H-NMR (d, CDCl$_3$): 2.0–2.3 (m, 8H), 2.305 (s, 3H), 3.15 (m, 2H), 4.59 (bs, 2H), 4.75 (m, 1H), 6.43 (d, J=8, 1H), 6.79 (d, J=8, 1H), 6.84 (d, J=7, 1H), 7.4–7.6 (m, 4H), 8.09 (m, 1H), 8.29 (m, 1H).

$^{13}$C-NMR (d, CDCl$_3$): 25.81, 35.97, 40.52, 59.84, 69.09, 104.46, 106.38, 115.09, 122.16, 125.00, 125.70, 126.31, 126.47, 127.12, 130.74, 132.39, 137.89, 153.06, 157.79, 158.00.

MS (%): 360 (parent+1, 100).

Anal. Calc'd. for C$_{23}$H$_{25}$N$_3$O.1/2(CO$_2$) (i.e., ½ carboxylate): C, 73.99, H, 6.61, N, 11.02. Found: C, 74.00, H, 6.65, N, 10.85.

EXAMPLE 67

6-[4-(1-Furan-2-ylmethyl-azetidin-3-yloxy)-naphthalen-1-yl]-pyridin-2-ylamine

Prepared as in Example 24, in 50% yield, mp 75–90° C., as the hydrochloride salt.

$^1$H-NMR (δ, CDCl$_3$): 3.34 (m, 2H), 3.71 (s, 2H), 3.97 (m, 2H), 4.58 (bs, 2H), 5.01 (m, 1H), 6.20 (m, 1H), 6.30 (m, 1H), 6.48 (d, J=8, 1H), 6.57 (d, J=8, 1H), 6.84 (d, J=7, 1H), 7.3–7.5 (m, 5H), 8.09 (m, 1H), 8.30 (m, 1H).

$^{13}$C-NMR (δ, CDCl$_3$): 54.99, 61.12, 66.84, 104.54, 106.57, 107.86, 110.06, 115.18, 122.07, 125.15, 125.63, 126.72, 126.95, 131.79, 132.16, 138.01, 142.28, 151.47, 152.74, 157.49, 157.90.

MS (%): 372 (parent+1, 100).

HRMS Calc'd. for C$_{23}$H$_{22}$N$_4$O$_2$: 372.1712. Found: 372.1690.

EXAMPLE 68

6-[4-(Pyrrolidin-2-ylmethoxy)-5,6,7,8-tetrahydro-naphthalen-1-yl]-pyridin-2-ylamine Prepared as in Example 48, using R-N-t-BOC-pyrrolidine-2-methanol, followed by conversion to the tosylate and alkylation with 2-(2,5-dimethylpyrrolyl)-6-(4-hydroxy-5,6,7,8-tetrahydro-naphthalen-1-yl)-pyridine, then deblocking to afford a tan, amorphous solid, in 95% yield, as the hydrochloride salt.

$^1$H-NMR (δ, CDCl$_3$): 1.63 (m, 3H), 1.74 (m, 4H), 1.90 (m, 1H), 2.68 (m, 4H), 2.96 (AB, 2H), 3.50 (m, 1H), 3.90 (m, 2H), 4.56 (bs, 2H), 6.37 (d, J=8, 1H), 6.63 (d, J=7, 1H), 6.67 (d, J=8, 1H), 7.07 (d, J=8, 1H), 7.40 (t, J=8, 1H).

$^{13}$C-NMR (δ, CDCl$_3$): 22.31, 22.77, 23.57, 25.28, 27.91, 28.13, 46.50, 57.42, 70.65, 106.06, 107.50, 114.32, 126.16, 126.80, 133.51, 136.22, 137.67, 156.28, 157.63, 158.72.

MS (%): 324 (parent+1, 100).

HRMS Calc'd. for C$_{20}$H$_{26}$N$_3$O: 324.2076. Found: 324.2055.

EXAMPLE 69

6-[4-(1-Methyl-pyrrolidin-2-ylmethoxy)-naphthalen-1-yl]-pyridin-2-ylamine

Prepared as in Example 24, using S-(−)-1-methyl-2-pyrrolidine methanol to afford, after deblocking in 88% yield, a tan solid, mp 80–95° C., α$_D$=−36.47° (c=1, CH$_2$Cl$_2$).

$^1$H-NMR (δ, CDCl$_3$): 1.8 (m, 2H), 1.9 (m, 1H), 2.12 (m, 1H), 2.34 (m, 1H), 2.56 (s, 3H), 2.83 (m, 1H), 3.13 (m, 1H), 4.13 (AB, 2H), 4.63 (bs, 2H), 6.41 (d, J=8, 1H), 6.83 (m, 2H), 7.46 (m, 4H), 8.10 (m, 1H), 8.31 (m, 1H).

$^{13}$C-NMR (δ, CDCl$_3$): 23.00, 28.92, 41.87, 57.79, 64.27, 71.57, 104.06, 106.45, 115.09, 122.07, 124.97, 125.64, 125.73, 126.01, 126.53, 127.20, 131.29, 132.06, 137.89, 154.78, 157.69, 158.07.

MS (%): 334 (parent+1, 100).

Anal. Calc'd. for C$_{21}$H$_{23}$N$_3$O.1/3H$_2$O: C, 74.31, H, 7.03, N, 12.38. Found: C, 74.11, H, 7.19, N, 12.22.

EXAMPLE 70

6-[4-(2-Amino-cyclohexyloxy)-5,6,7,8-tetrahydro-naphthalen-1-yl]-pyridin-2-ylamine Prepared as in Example 48, via the following four-step sequence: 2-(2,5-dimethylpyrrolyl)-6-[4-hydroxy-5,6,7,8-tetrahydro-naphthalen-1-yl]-pyridine was first alkylated with 2-chlorocyclohexanone, using potassium carbonate as the base and a catalytic amount of sodium iodide, in dimethylformamide at 80° C. for 24 hours, in 92% yield. The resulting ketone was converted to the oxime methyl ether using O-methylhydroxylamine hydrochloride and triethylamine in methanol at reflux for 16 h in 81% yield. The oxime ether was then reduced to the amine using borane methyl sulfide in tetrahydrofuran at reflux for 2 days, followed by refluxing in ethanol with sodium carbonate and cesium fluoride for 16 hours, in 12% yield. The amine was then deblocked with hydroxylamine hydrochloride in refluxing aqueous ethanol to afford the desired final product in 89% yield as a tan solid after conversion to the hydrochloride salt.

$^1$H-NMR (δ, CDCl$_3$): 1.2–1.5 (m, 6H), 1.6–1.9 (m, 6H), 2.70 (m, 4H), 2.94 (m, 1H), 4.49 (m, 1H), 4.55 (bs, 2H), 6.39 (d, J=8, 1H), 6.65 (d, J=8, 1H), 6.72 (d, J=8, 1H), 7.07 (d, J=8, 1H), 7.43 (t, J=8, 1H).

$^{13}$C-NMR (δ, CDCl$_3$): 20.3, 22.4, 22.37, 23.7, 23.9, 27.4, 28.2, 30.9, 52.1, 75.8, 106.1, 108.6, 114.4, 126.8, 127.0, 133.1, 136.5, 137.7, 154.9, 157.6, 158.7.

MS (%): 338 (parent+1, 100).

HRMS Calc'd. for C$_{21}$H$_{28}$N$_3$O: 338.2232. Found: 338.2256.

EXAMPLE 71

6-[4-(Azetidin-2-ylmethoxy)-naphthalen-1-yl]-pyridin-2-ylamine

Prepared as in Example 24 using L-azetidine-2-carboxylic acid as the precursor to N-t-BOC-azetidine-2-methanol as the reagent to add to 2-(2,5-dimethylpyrrolyl)-6-(4-fluoro-naphth-1-yl)pyridine, followed by removal of blocking groups to afford 45% yield of a solid, mp 135–150° C.

$^1$H-NMR (δ, CDCl$_3$): 2.33 (m, 1H), 2.43 (m, 1H), 3.4 (bs, 1H), 3.54 (m, 1H), 3.67 (m, 1H), 4.20 (m, 2H), 4.37 (m, 1H), 4.625 (bs, 2H), 6.45 (d, J=8, 1H), 6.84 (m, 2H), 7.45 (m, 4H), 8.10 (m, 1H), 8.31 (m, 1H).

$^{13}$C-NMR (δ, CDCl$_3$): 23.93, 44.25, 57.45, 72.10, 104.39, 106.54, 115.15, 122.00, 125.04, 125.63, 125.73, 126.63, 127.15, 131.50, 132.06, 137.95, 154.59, 157.62, 158.03.

MS (%): 306 (parent+1, 100).

Anal. Calc'd. for C$_{19}$H$_{19}$N$_3$O.2HCl.3/2H$_2$O.1/2(C$_4$H$_8$O): C, 56.13, H, 6.28, N, 9.35. Found: C, 56.24, H, 6.52, N, 9.05.

EXAMPLE 72

6-[4-(1-Pyridin-3-ylmethyl-azetidin-3-yloxy)-naphthalen-1-yl]-pyridin-2-ylamine Prepared as in Example 24, in 24% yield, mp 150–180° C., as the hydrochloride salt.

$^1$H-NMR (δ, CDCl$_3$): 3.29 (m, 2H), 3.71 (s, 2H), 3.92 (m, 2H), 4.57 (bs, 2H), 5.005 (m, 1H), 6.47 (d, J=8, 1H), 6.56 (d, J=8, 1H), 6.83 (d, J=7, 1H), 7.24 (m, 1H), 7.39 (d, J=8, 1H), 7.5–7.6 (m, 4H), 7.63 (m, 1H), 8.09 (m, 1H), 8.29 (m, 1H), 8.50 (m, 1H), 8.54 (s, 1H).

$^{13}$C-NMR (δ, CDCl$_3$): 60.9, 61.4, 66.8, 104.5, 106.6, 115.1, 122.0, 123.4, 125.5, 125.7, 126.7, 126.9, 132.0, 132.2, 133.3, 136.0, 138.0, 148.7, 149.8, 152.7, 157.5, 158.0.

MS (%): 383 (parent+1, 100).

Anal. Calc'd. for C$_{24}$H$_{22}$N$_4$O.3HCl.3H$_2$O.1/3(C$_4$H$_8$O): C, 53.39, H, 5.95, N, 9.83. Found: C, 53.22, H, 6.18, N, 9.43.

EXAMPLE 73

6-[4-(Azetidin-3-ylmethoxy)-naphthalen-1-yl]-pyridin-2-ylamine

Prepared as in Example 24, in which N-BOC azetidine-3-methanol was added to 2-(2,5-dimethylpyrrolyl)-6-(4-fluoro-naphth-1-yl)pyridine as in Example 24D followed by sequential removal of the BOC and pyrrolyl protecting groups, with the final step proceeding in 75% yield, in 75% yield, mp 88–110° C., as the hydrochloride salt.

$^1$H-NMR (δ, CDCl$_3$): 3.27 (m, 1H), 3.64 (m, 2H), 3.78 (m, 2H), 4.25 (d, J=6, 2H), 4.63 (bs, 2H), 6.45 (d, J=8, 1H), 6.83 (m, 2H), 7.4–7.6 (m, 4H), 8.09 (m, 1H), 8.29 (m, 1H).

$^{13}$C-NMR (δ, CDCl$_3$): 34.2, 49.8, 69.8, 104.2, 106.5, 115.1, 122.0, 125.0, 125.4, 125.6, 125.7, 126.6, 127.1, 131.4, 132.0, 138.0, 154.7, 157.6, 158.1.

MS (%): 306 (parent+1, 100).

Anal. Calc'd. for C$_{19}$H$_{19}$N$_3$O.2HCl2H$_2$O.3/2(C$_4$H$_8$O): C, 57.25, H, 7.00, N, 8.04. Found: C, 57.47, H, 7.14, N, 8.21.

EXAMPLE 74

6-[4-(1-Pyridin-2-ylmethyl-azetidin-3-yloxy)-naphthalen-1-yl]-pyridin-2-ylamine Prepared as in Example 24, in 24% yield, mp 97–120° C., as the hydrochloride salt from tetrahydrofuran.

$^1$H-NMR (δ, CDCl$_3$): 3.42 (m, 2H), 3.89 (s, 2H), 4.015 (m, 2H), 4.62 (bs, 2H), 5.045 (m, 1H), 6.47 (d, J=8, 1H), 6.57 (d, J=8, 1H), 6.82 (d, J=7, 1H), 7.16 (m, 1H), 7.3–7.5 (m, 5H), 7.64 (t, J=8, 1H), 8.07 (m, 1H), 8.30 (m, 1H), 8.55 (m, 1H).

$^{13}$C-NMR (δ, CDCl$_3$): 61.62, 64.89, 67.10, 104.52, 106.64, 115.14, 122.09, 122.13, 122.42, 125.18, 125.60, 126.73, 126.92, 131.75, 132.16, 136.58, 138.04, 149.30, 152.77, 157.41, 157.76, 157.96.

MS (%): 383 (parent+1, 100).

Anal. Calc'd. for C$_{24}$H$_{22}$N$_4$O.3HCl.7/4H$_2$O: C, 55.08, H, 5.49, N, 10.70. Found: C, 55.44, H, 5.61, N, 10.31.

EXAMPLE 75

6-[4-(N-methyl-azetidin-3-yloxy)-naphthalen-1-yl]-pyridin-2-ylamine

Prepared as in Example 24, using formaldehyde in methanol with sodium cyanoborohydride at room temperature, in 30% yield, mp 240–255° C., as the hydrochloride salt from tetrahydrofuran.

$^1$H-NMR (δ, CDCl$_3$): 2.45 (s, 3H), 2.75 (bs, 2H), 3.30 (m, 2H), 3.99 (m, 2H), 4.96 (m, 1H), 6.47 (d, J=8, 1H), 6.55 (d, J=8, 1H), 6.80 (d, J=7, 1H), 7.3–7.5 (m, 4H), 8.03 (m, 1H), 8.28 (m, 1H).

$^{13}$C-NMR (δ, CDCl$_3$): 45.81, 63.07, 66.19, 104.44, 106.84, 115.08, 121.97, 125.23, 125.43, 125.57, 126.76, 126.87, 131.82, 132.15, 138.14, 152.56, 157.13, 158.05.

MS (%): 306 (parent+1, 100).

Anal. Calc'd. for C$_{19}$H$_{19}$N$_3$O.2HCl.2H$_2$O: C, 55.08, H, 6.08, N, 10.14. Found: C, 55.34, H, 6.01, N, 9.82.

EXAMPLE 76

6-[4-(N-Isopropyl-azetidin-3-yloxy)-naphthalen-1-yl]-pyridin-2-ylamine

Prepared as in Example 24, as a byproduct of the reaction used for preparation of Example 75, from acetone in the methanol, in 19% yield, mp 120–135° C., as the hydrochloride salt from tetrahydrofuran.

$^1$H-NMR (δ, CDCl$_3$): 0.99 (d, J=6, 6H), 2.49 (septet, J=6, 1H), 3.25 (m, 2H), 3.96 (m, 2H), 4.65 (bs, 2H), 4.97 (m, 1H), 6.48 (d, J=8, 1H), 6.60 (d, J=8, 1H), 6.81 (d, J=6, 1H), 7.4–7.5 (m, 4H), 8.03 (m, 1H), 8.27 (m, 1H).

$^{13}$C-NMR (δ, CDCl$_3$): 19.30, 50.44, 58.78, 65.40, 104.52, 106.81, 115.12, 122.00, 125.20, 125.45, 125.56, 126.73, 126.89, 131.78, 132.15, 138.15, 152.66, 157.21, 158.02.

MS (%): 332 (parent+1, 100).

Anal. Calc'd. for C$_{21}$H$_{23}$N$_3$O.2HCl.2H$_2$O: C, 57.02, H, 6.61, N, 9.50. Found: C, 57.04, H, 6.51, N, 9.29.

EXAMPLE 77

6-[4-(2-Dimethylamino-ethoxy)-6,7,8,9-tetrahydro-5H-benzocyclohepten-1-yl]-pyridin-2-ylamine Prepared as in Example 37, using 4-hydroxy-6,7,8,9-tetrahydro-5H-benzocycloheptene as the starting material, which was prepared as follows: 8 g (71.4 mmol) 2-hydroxypyrone (Syn. Commun., 5, 461, (1975)) and 20 mL cycloheptene were reacted in a sealed tube at 150° C. for 24 h to give 1-oxo-3,4,6,7,8,9-hexahydro-5H-benzocycloheptene in 49.5% yield, followed by reaction with isopropenyl acetate to afford the enol acetate and treatment with 2,3-dichloro-5,6-dicyanobenzoquinone at 90° C. for 1.5 h (see J. Med. Chem., 37, 3803 (1994)) to afford 4-acetoxy-6,7,8,9-tetrahydro-5H-benzocycloheptene in 69% yield as an oil. Hydrolysis with 3.7 equivalents of powdered potassium hydroxide in ethanol at room temperature for 2 h gave a 44% yield of the desired 4-hydroxy-6,7,8,9-tetrahydro-5H-benzocycloheptene after purification by column chromatography as a white solid. The remaining steps in the sequence then followed Example 48. The final step proceeded in 89% yield to give the product as an amorphous solid as the hydrochloride salt from ether.

$^1$H-NMR (δ, CDCl$_3$): 1.58 (m, 4H), 1.79 (m, 2H), 2.34 (s, 6H), 2.75 (m, 4H), 2.93 (m, 2H), 4.06 (t, J=6, 2H), 4.48 (bs, 2H), 6.39 (d, J=8, 1H), 6.62 (d, J=8, 1H), 6.74 (d, J=8, 1H), 7.10 (d, J=8, 1H), 7.41 (d, J=8, 1H).

$^{13}$C-NMR (δ, CDCl$_3$): 25.51, 27.36, 27.75, 31.21, 32.46, 46.03, 58.35, 67.43, 105.94, 109.95, 114.72, 127.58, 132.85, 133.74, 137.54, 142.88, 155.43, 157.74, 159.32.

MS (%): 326 (parent+1, 100).

I claim:

1. A compound of the formula

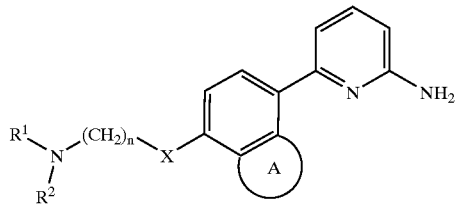

I wherein ring A is a fused 5–7 membered saturated or unsaturated ring wherein from zero to two of the ring members are heteroatoms selected, independently, from nitrogen, oxygen and sulfur, with the proviso that no two adjacent ring members can both be heteroatoms;

X is oxygen or a bond;

n is an integer from two to six; and $R^1$ and $R^2$ are selected, independently, from (C$_1$–C$_6$) alkyl, aryl, tetrahydronaphthalene and aralkyl, wherein said aryl and the aryl moiety of said aralkyl is phenyl or naphthyl and the alkyl moiety is straight or branched and contains from 1 to 6 carbon atoms, and wherein said (C$_1$–C$_6$) alkyl, said aryl, said tetrahydronaphthalene and the aryl moiety of said aralkyl may optionally be substituted with from one to three substituents that are selected, independently, from halo, nitro, hydroxy, cyano, amino, (C$_1$–C$_4$) alkoxy, and (C$_1$–C$_4$) alkylamino;

or $R^1$ and $R^2$ form, together with the nitrogen to which they are attached, a piperazine, azetidine, piperidine or pyrrolidine ring or an azabicyclic ring containing from 6 to 14 ring members, from 1 to 3 of which are nitrogen and the rest of which are carbon;

and wherein said piperazine, azetidine, piperidine and pyrrolidine rings may optionally be substituted with one or more substituents that are selected, independently, from (C$_1$–C$_6$)alkyl, amino, (C$_1$–C$_6$) alkylamino, [di-(C$_1$–C$_6$)alkyl]amino, phenyl, substituted 5 to 6 membered heterocyclic rings containing from 1 to 4 rings nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents that are selected; Independently, from halo, (C$_1$–C$_3$)alkyl, (C$_1$–C$_3$)alkoxy, nitro, amino, cyano, CF$_3$ and OCF$_3$;

wherein, provided when X is oxygen and $R^1$ or $R^2$ is alkyl, $R^1$ or $R^2$ together with the nitrogen may be connected onto the (CH2)$_n$ group to form a ring of from 4 to 7 members;

or the pharmaceutically acceptable salt of such compounds.

2. A compound according to claim 1, wherein NR$^1$R$^2$ is an optionally substituted piperidine, azetidine, piperazine or pyrrolidine ring or a 3-aza-bicyclo[3.1.0]hex-6-ylamine ring;

and wherein said piperazine, azetidine, piperidine and pyrrolidine rings may optionally be substituted with one or more substituents that are selected, independently, from (C$_1$–C$_6$)alkyl, amino, (C$_1$–C$_6$) alkylamino, [di-(C$_1$–C$_6$)alkyl]amino, phenyl, substituted 5 to 6 membered heterocyclic rings containing from 1 to 4 ring nitrogen atoms, benzoyl, benzoylmethyl, benzylcarbonyl, phenylaminocarbonyl, phenylethyl and phenoxycarbonyl, and wherein the phenyl moieties of any of the foregoing substituents may optionally be substituted with one or more substituents that are selected, independently, from halo, (C$_1$–C$_3$)alkyl, (C$_1$–C$_3$)alkoxy, nitro, amino, cyano, CF$_3$ and OCF$_3$.

3. A compound according to claim 1 wherein NR$^1$R$^2$ forms an azabicyclic ring having the formula

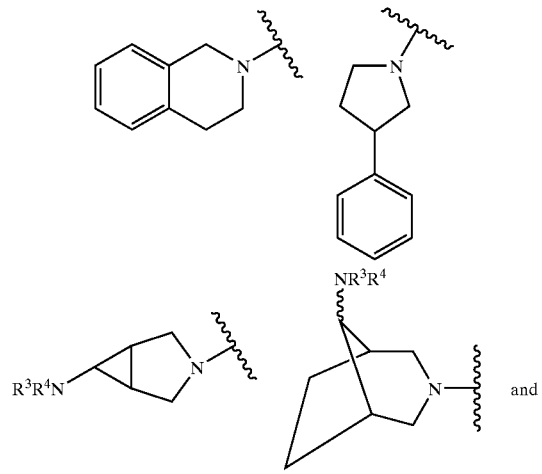

and

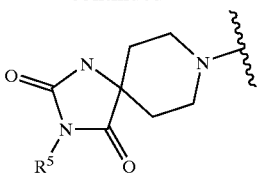

wherein R³ and R⁴ are selected from hydrogen, $(C_1-C_6)$ alkyl, phenyl, naphthyl, $(C_1-C_6)$alkyl-C(=O)—, HC(=O)—, $(C_1-C_6)$alkoxy-(C=O)—, phenyl-C(=O)—, naphthyl-C(=O)—, and $R^6R^7NC(=O)$— wherein R⁶ and R⁷ are selected, independently, from hydrogen and $(C_1-C_6)$alkyl; and R⁵ is selected from hydrogen, $(C_1-C_6)$alkyl, phenyl, naphthyl, phenyl-$(C_1-C_6)$alkyl- and naphthyl$(C_1-C_6)$alkyl-.

4. A compound according to claim 1 selected from the group consisting of:

6-[4-(2-Dimethylamino-ethoxy)-naphthalen-1-yl]-pyridin-2-ylamine;

6-[4-(2-Pyrrolidin-1-yl-ethoxy)-naphthalen-1-yl]-pyridin-2-ylamine;

6-(4-{2-[(Benzo[1,3]dioxol-5-ylmethyl)-amino]-ethoxy}-naphthalen-1-yl)-pyridin-2-ylamine;

6-{4-[2-(6,7-Dimethoxy-3,4-dihydro-1H-isoquinolin-2-yl)-ethoxy]-naphthalen-1-yl}-pyridin-2-ylamine;

3-{2-[4-(6-Amino-pyridin-2-yl)-naphthalen-1-yloxy]-ethyl}-3-aza-bicyclo[3.1.0]hex-6-ylamine;

6-{4-[2-(4-Phenethyl-piperazin-1-yl)-ethoxy]-naphthalen-1-yl}-pyridin-2-ylamine;

6-{4-[2-(3-Amino-pyrrolidin-1-yl)-ethoxy]-naphthalen-1-yl}-pyridin-2-ylamine;

6-[4-(1-Benzyl-piperidin-4-yloxy)-naphthalen-1-yl]-pyridin-2-ylamine;

6-[4-(1-Benzyl-pyrrolidin-3-yloxy)-naphthalen-1-yl]-pyridin-2-ylamine;

6-[4-(Piperidin-4-yloxy)-naphthalen-1-yl]-pyridin-2-ylamine;

6-[4-(Pyrrolidin-3-yloxy)-naphthalen-1-yl]-pyridin-2-ylamine;

6-[4-(1-Isobutyl-piperidin-4-yloxy)-naphthalen-1-yl]-pyridin-2-ylamine;

6-[4-(1-Furan-2-ylmethyl-piperidin-4-yloxy)-naphthalen-1-yl]-pyridin-2-ylamine;

6-[4-(1-Isobutyl-pyrrolidin-3-yloxy)-naphthalen-1-yl]-pyridin-2-ylamine;

6-[4-(1-Furan-2-ylmethyl-pyrrolidin-3-yloxy)-naphthalen-1-yl]-pyridin-2-ylamine;

6-[4-(2-Diisopropylamino-ethoxy)-naphthalen-1-yl]-pyridin-2-ylamine;

6-[4-(1-Methyl-piperidin-4-yloxy)-naphthalen-1-yl]-pyridin-2-ylamine;

6-[4-(1-Methyl-pyrrolidin-3-yloxy)-naphthalen-1-yl]-pyridin-2-ylamine;

6-[4-(3-Dimethylamino-propoxy)-naphthalen-1-yl]-pyridin-2-ylamine;

6-[4-(1-Aza-bicyclo[2.2.2]oct-3-yloxy)-naphthalen-1-yl]-pyridin-2-ylamine;

6-[4-(2-Piperidin-1-yl-ethoxy)-naphthalen-1-yl]-pyridin-2-ylamine

6-{4-[2-(3,4-Dihydro-1H-isoquinolin-2-yl)-ethoxy]-naphthalen-1-yl}-pyridin-2-ylamine;

6-{4-[2-(4-Dimethylamino-piperidin-1-yl)-ethoxy]-naphthalen-1-yl}-pyridin-2-ylamine;

6-{4-[2-(tert-Butyl-methyl-amino)-ethoxy]-naphthalen-1-yl}-pyridin-2-ylamine;

6-{4-[2-(4-Methyl-piperazin-1-yl)-ethoxy]-naphthalen-1-yl}-pyridin-2-ylamine;

6-{4-[2-(4-Phenyl-piperidin-1-yl)-ethoxy]-naphthalen-1-yl}-pyridin-2-ylamine;

6-{4-[2-(7,8-Dihydro-5H-[1,3]dioxolo[4,5-g]isoquinolin-6-yl)-ethoxy]-naphthalen-1-yl}-pyridin-2-ylamine;

6-[4-(Piperidin-2-ylmethoxy)-naphthalen-1-yl]-pyridin-2-ylamine;

6-[4-(1-Methyl-piperidin-2-ylmethoxy)-naphthalen-1-yl]-pyridin-2-ylamine;

6-[4-(1-Methyl-piperidin-3-ylmethoxy)-naphthalen-1-yl]-pyridin-2-ylamine;

6-[4-(2-Amino-cyclohexyloxy)-naphthalen-1-yl]-pyridin-2-ylamine;

6-[4-(Piperidin-3-ylmethoxy)-naphthalen-1-yl]-pyridin-2-ylamine;

6-[4-(1-Isobutyl-azetidin-3-yloxy)-naphthalen-1-yl]-pyridin-2-ylamine;

6-[4-(1-Furan-2-ylmethyl-azetidin-3-yloxy)-naphthalen-1-yl]-pyridin-2-ylamine;

6-[4-(8-Methyl-8-aza-bicyclo[3.2.1]oct-3-yloxy)-naphthalen-1-yl]-pyridin-2-ylamine;

6-[4-(Azetidin-3-yloxy)-naphthalen-1-yl]-pyridin-2-ylamine;

6-[4-(1-Methyl-pyrrolidin-2-ylmethoxy)-naphthalen-1-yl]-pyridin-2-ylamine;

6-[4-(Azetidin-2-ylmethoxy)-naphthalen-1-yl]-pyridin-2-ylamine;

6-[7-(2-Dimethylamino-ethoxy)-indan-4-yl]-pyridin-2-ylamine;

6-[7-(2-Pyrrolidin-1-yl-ethoxy)-indan-4-yl]-pyridin-2-ylamine;

6-{7-[2-(Benzyl-methyl-amino)-ethoxy]-indan-4-yl}-pyridin-2-ylamine;

6-{7-[2-(4-Phenethyl-piperazin-1-yl)-ethoxy]-indan-4-yl}-pyridin-2-ylamine;

6-{7-[2-(4-Isobutyl-piperazin-1-yl)-ethoxy]-indan-4-yl}-pyridin-2-ylamine;

6-[7-(2-Diisopropylamino-ethoxy)-indan-4-yl]-pyridin-2-ylamine;

6-{7-[2-(7,8-Dihydro-5H-[1,3]dioxolo[4,5-g]isoquinolin-6-yl)-ethoxy]-indan-4-yl}-pyridin-2-amine;

6-{7-[2-(4-Methyl-piperazin-1-yl)-ethoxy]-indan-4-yl}-pyridin-2-ylamine;

6-{7-[2-(tert-Butyl-methyl-amino)-ethoxy]-indan-4-yl}-pyridin-2-ylamine;

6-{7-[2-(4-Dimethylamino-piperidin-1-yl)-ethoxy]-indan-4-yl}-pyridin-2-ylamine;

6-[8-(2-Dimethylamino-ethoxy)-1,2,3,4-tetrahydro-1,4-methano-naphthalen-5-y]-pyridin-2-ylamine;

6-[8-(2-Pyrrolidin-1-yl-ethoxy)-1,2,3,4-tetrahydro-1,4-methano-naphthalen-5-yl]-pyridin-2-ylamine;

6-[4-(2-Dimethylamino-ethoxy)-5,6,7,8-tetrahydro-naphthalen-1-yl]-pyridin-2-ylamine;

6-[4-(2-Pyrrolidin-1-yl-ethoxy)-5,6,7,8-tetrahydro-naphthalen-1-yl]-pyridin-2-ylamine;

6-{4-[2-(tert-Butyl-methyl-amino)-ethoxy]-5,6,7,8-tetrahydro-naphthalen-1-yl}-pyridin-2-ylamine;

6-[4-(2-Diisopropylamino-ethoxy)-5,6,7,8-tetrahydro-naphthalen-1-yl]-pyridin-2-ylamine;

6-[4-(2-Diethylamino-ethoxy)-5,6,7,8-tetrahydro-naphthalen-1-yl]-pyridin-2-ylamine;

6-{4-[2-(3,4-Dihydro-1H-isoquinolin-2-yl)-ethoxy]-5,6,7,8-tetrahydro-naphthalen-1-yl}-pyridin-2-ylamine;

6-[4-(2-Piperidin-1-yl-ethoxy)-5,6,7,8-tetrahydro-naphthalen-1-yl]-pyridin-2-ylamine;

6-{4-[2-(7,8-Dihydro-5H-[1,3]dioxolo[4,5-g]isoquinolin-6-yl)-ethoxy]-5,6,7,8-tetrahydro-naphthalen-1-yl}-pyridin-2-ylamine;

6-{4-[2-(4-Methyl-piperazin-1-yl)-ethoxy]-5,6,7,8-tetrahydro-naphthalen-1-yl}-pyridin-2-ylamine;

6-{4-[2-(4-Dimethylamino-piperidin-1-yl)-ethoxy]-5,6,7,8-tetrahydro-naphthalen-1-yl}-pyridin-2-ylamine;

6-{4-[2-(7,8-Dihydro-5H-[1,3]dioxolo[4,5-g]isoquinolin-6-yl)-ethoxy]-5,6,7,8-tetrahydro-naphthalen-1-yl}-pyridin-2-ylamine;

6-[4-(1-Isobutyl-piperidin-3-ylmethoxy)-5,6,7,8-tetrahydro-naphthalen-1-yl]-pyridin-2-ylamine;

6-[4-(1-Methyl-piperidin-3-ylmethoxy)-5,6,7,8-tetrahydro-naphthalen-1-yl]-pyridin-2-ylamine;

6-{4-[2-(2-Diethylamino-ethoxy)-ethoxy]-5,6,7,8-tetrahydro-naphthalen-1-yl}-pyridin-2-ylamine;

6-[4-(Piperidin-3-ylmethoxy)-5,6,7,8-tetrahydro-naphthalen-1-yl]-pyridin-2-ylamine;

6-[4-(2-Amino-cyclohexyloxy)-5,6,7,8-tetrahydro-naphthalen-1-yl]-pyridin-2-ylamine;

6-[4-(Pyrrolidin-2-ylmethoxy)-5,6,7,8-tetrahydro-naphthalen-1-yl]-pyridin-2-ylamine; and 6-[4-(2-Dimethylamino-ethoxy)-6,7,8,9-tetrahydro-5H-benzocyclohepten-1-yl]-pyridin-2-ylamine;

6-[4-(2-Amino-cyclopentyloxy)-5,6,7,8-tetrahydro-naphthalen-1-yl]-pyridin-2-ylamine;

6-[4-(2-Amino-cyclobutyloxy)-5,6,7,8-tetrahydro-naphthalen-1-yl]-pyridin-2-ylamine;

6-[4-(2-Amino-cyclopropyloxy)-5,6,7,8-tetrahydro-naphthalen-1-yl]-pyridin-2-ylamine;

6-[4-(3-Amino-cyclohexyloxy)-5,6,7,8-tetrahydro-naphthalen-1-yl]-pyridin-2-ylamine;

6-[4-(3-Amino-cyclopentyloxy)-5,6,7,8-tetrahydro-naphthalen-1-yl]-pyridin-2-ylamine;

6-[4-(3-Amino-cyclobutyloxy)-5,6,7,8-tetrahydro-naphthalen-1-yl]-pyridin-2-ylamine;

6-[4-(4-Amino-cyclohexyloxy)-5,6,7,8-tetrahydro-naphthalen-1-yl]-pyridin-2-ylamine;

6-[4-(2-Amino-cyclopentyloxy)-naphthalen-1-yl]-pyridin-2-ylamine;

6-[4-(2-Amino-cyclobutyloxy)-naphthalen-1-yl]-pyridin-2-ylamine;

6-[4-(2-Amino-cyclopropyloxy)-naphthalen-1-yl]-pyridin-2-ylamine;

6-[4-(3-Amino-cyclohexyloxy)-naphthalen-1-yl]-pyridin-2-ylamine;

6-[4-(3-Amino-cyclopentyloxy)-naphthalen-1-yl]-pyridin-2-ylamine;

6-[4-(3-Amino-cyclobutyloxy)-naphthalen-1-yl]-pyridin-2-ylamine;

6-[4-(4-Amino-cyclohexyloxy)-naphthalen-1-yl]-pyridin-2-ylamine;

6-[4-(2-Amino-cyclopentyloxy)-indan-4-yl]-pyridin-2-ylamine;

6-[4-(2-Amino-cyclobutyloxy)-indan-4-yl]-pyridin-2-ylamine;

6-[4-(2-Amino-cyclopropyloxy)-indan-4-yl]-pyridin-2-ylamine;

6-[4-(3-Amino-cyclohexyloxy)-indan-4-yl]-pyridin-2-ylamine;

6-[4-(3-Amino-cyclopentyloxy)-indan-4-yl]-pyridin-2-ylamine;

6-[4-(3-Amino-cyclobutyloxy)-indan-4-yl]-pyridin-2-ylamine;

6-[4-(4-Amino-cyclohexyloxy)-indan-4-yl]-pyridin-2-ylamine;

6-[4-Piperidin-3-ylmethoxy)-6,7,8,9-tetrahydro-5H-benzocyclohepten-1-yl]-pyridin-2-ylamine;

6-[4-(2-Pyrrolidinyl-ethoxy)-6,7,8,9-tetrahydro-5H-benzocyclohepten-1-yl]-pyridin-2-ylamine;

6-[4-(2-Amino-cyclohexyloxy)-6,7,8,9-tetrahydro-5H-benzocyclohepten-1-yl]-pyridin-2-ylamine;

6-[4-(2-(4-Dimethylamino-piperidin-1-yl)-ethoxy))-6,7,8,9-tetrahydro-5H-benzocyclohepten-1-yl]-pyridin-2-ylamine; and 6-[4-(2-(4-Methyl-piperazin-1-yl)-ethoxy))-6,7,8,9-tetrahydro-5H-benzocyclohepten-1-yl]-pyridin-2-ylamine, and a pharmaceutically acceptable salts of the foregoing compounds.

\* \* \* \* \*